United States Patent
Terry et al.

(10) Patent No.: US 11,504,071 B2
(45) Date of Patent: Nov. 22, 2022

(54) PATIENT RISK ASSESSMENT BASED ON DATA FROM MULTIPLE SOURCES IN A HEALTHCARE FACILITY

(71) Applicant: Hill-Rom Services, Inc., Batesville, IN (US)

(72) Inventors: Ryan Terry, Hinsdale, IL (US); Brian L. Lawrence, Cincinnati, OH (US); Kirsten M. Emmons, Batesville, IN (US); Darren S. Hudgins, Cary, NC (US); Eric D. Agdeppa, Cincinnati, OH (US); Yongji Fu, Harrison, OH (US); Jared Prickel, Batesville, IN (US); Susan Kayser, Batesville, IN (US); Stacey A. Fitzgibbons, DeWitt, NY (US); Johannes de Bie, Monte San Pietro (IT); Craig M. Meyerson, Syracuse, NY (US); Lori Ann Zapfe, Milroy, IN (US); Jotpreet Chahal, Fayetteville, NY (US); Yuan Shi, Singapore (SG); Eugene Urrutia, Durham, NC (US); Chiew Yuan Chung, Singapore (SG); Matthew M. Riordan, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 504 days.

(21) Appl. No.: 16/374,820

(22) Filed: Apr. 4, 2019

(65) Prior Publication Data
US 2019/0307405 A1    Oct. 10, 2019

Related U.S. Application Data

(60) Provisional application No. 62/655,385, filed on Apr. 10, 2018.

(51) Int. Cl.
*G16H 50/30* (2018.01)
*A61B 5/00* (2006.01)
(Continued)

(52) U.S. Cl.
CPC .......... *A61B 5/7275* (2013.01); *A61B 5/0002* (2013.01); *A61B 5/02055* (2013.01);
(Continued)

(58) Field of Classification Search
CPC ........ G16H 40/20; G16H 10/60; G16H 50/30; A61B 5/7275; A61B 5/412; A61B 5/447; A61F 13/42
(Continued)

(56) References Cited

U.S. PATENT DOCUMENTS

| 5,561,412 A | 10/1996 | Novak et al. |
| 5,699,038 A | 12/1997 | Ulrich et al. |

(Continued)

FOREIGN PATENT DOCUMENTS

| WO | 2015023674 A1 | 2/2015 |
| WO | 2015/157573 A2 | 10/2015 |

(Continued)

OTHER PUBLICATIONS

"Hill-Rom® Pressure Ulcer/Injury Prevalence Survey Data Collection Form Instructions," © 2018 Hill-Rom Services, Inc.; Jan. 2, 2018; 4 pages.
(Continued)

*Primary Examiner* — Mark Holcomb
(74) *Attorney, Agent, or Firm* — Barnes & Thornburg LLP

(57) ABSTRACT

Apparatus for assessing medical risks of a patient includes an analytics engine and equipment that provides data to the analytics engine. The equipment includes a patient support apparatus such as a patient bed, a nurse call computer, a
(Continued)

physiological monitor, a patient lift, a locating computer of a locating system, and an incontinence detection pad. The analytics engine analyzes the data from the equipment to determine a sepsis risk score, a falls risk score, and a pressure injury score. The apparatus further include displays that are communicatively coupled to the analytics engine and that display the sepsis, falls, and pressure injury risk scores. The displays include a status board display located at a master nurse station, an in-room display provided by a room station of a nurse call system, an electronic medical records (EMR) display of an EMR computer, and a mobile device display of a mobile device of a caregiver assigned to the patient.

32 Claims, 12 Drawing Sheets

(51) Int. Cl.
| | |
|---|---|
| *G16H 40/20* | (2018.01) |
| *G16H 10/60* | (2018.01) |
| *A61B 5/0205* | (2006.01) |
| *A61F 13/42* | (2006.01) |
| *A61G 7/053* | (2006.01) |
| *A61G 7/057* | (2006.01) |
| *A61B 5/021* | (2006.01) |
| *A61B 5/024* | (2006.01) |
| *A61B 5/08* | (2006.01) |
| *A61B 5/11* | (2006.01) |
| *A61B 5/1455* | (2006.01) |
| *A61B 5/20* | (2006.01) |
| *A61B 5/318* | (2021.01) |

(52) U.S. Cl.
CPC ............. *A61B 5/412* (2013.01); *A61B 5/447* (2013.01); *A61B 5/6891* (2013.01); *A61B 5/6892* (2013.01); *A61B 5/7445* (2013.01); *A61F 13/42* (2013.01); *A61G 7/053* (2013.01); *A61G 7/057* (2013.01); *G16H 10/60* (2018.01); *G16H 40/20* (2018.01); *G16H 50/30* (2018.01); *A61B 5/021* (2013.01); *A61B 5/02438* (2013.01); *A61B 5/0816* (2013.01); *A61B 5/1115* (2013.01); *A61B 5/1117* (2013.01); *A61B 5/14551* (2013.01); *A61B 5/202* (2013.01); *A61B 5/318* (2021.01)

(58) Field of Classification Search
USPC ........................................................ 705/2–4
See application file for complete search history.

(56) References Cited

U.S. PATENT DOCUMENTS

| | | | |
|---|---|---|---|
| 5,820,858 | A | 10/1998 | Leturcq et al. |
| 5,830,679 | A | 11/1998 | Bianchi et al. |
| 5,838,223 | A | 11/1998 | Gallant et al. |
| 6,147,592 | A | 11/2000 | Ulrich et al. |
| 6,362,725 | B1 | 3/2002 | Ulrich et al. |
| 6,782,321 | B1 | 8/2004 | Burton |
| 6,897,780 | B2 | 5/2005 | Ulrich et al. |
| 7,242,308 | B2 | 7/2007 | Ulrich et al. |
| 7,253,366 | B2 | 8/2007 | Bhai |
| 7,282,031 | B2 | 10/2007 | Hendrich |
| 7,319,386 | B2 | 1/2008 | Collins, Jr. et al. |
| 7,340,431 | B1 | 3/2008 | McManus et al. |
| 7,538,659 | B2 | 5/2009 | Ulrich et al. |
| 7,612,681 | B2 | 11/2009 | Azzaro et al. |
| 7,682,308 | B2 | 3/2010 | Hendrich |
| 7,746,218 | B2 | 6/2010 | Collins, Jr. et al. |
| 7,939,282 | B2 | 5/2011 | Fast et al. |
| 7,994,900 | B1 | 8/2011 | Langstroth et al. |
| 8,069,471 | B2 | 11/2011 | Boren |
| 8,150,717 | B2 | 4/2012 | Whitmore |
| 8,336,239 | B2 | 12/2012 | McDermott et al. |
| 8,495,583 | B2 | 7/2013 | Bassin et al. |
| 8,510,126 | B2 | 8/2013 | Martin et al. |
| 8,525,680 | B2 | 9/2013 | Riley et al. |
| 8,645,921 | B2 | 2/2014 | Bassin et al. |
| 8,671,102 | B2 | 3/2014 | Reville et al. |
| 8,675,920 | B2 | 3/2014 | Hanson et al. |
| 8,725,539 | B2 | 5/2014 | Romano et al. |
| 8,736,453 | B2 | 5/2014 | Wilson et al. |
| 8,779,924 | B2 | 7/2014 | Pesot et al. |
| 8,805,641 | B2 | 8/2014 | Greene |
| 8,823,526 | B2 | 9/2014 | Kaiser et al. |
| 8,923,826 | B2 | 12/2014 | Kiddie et al. |
| 9,036,019 | B2 | 5/2015 | Hanson et al. |
| 9,041,810 | B2 | 5/2015 | Ecker et al. |
| 9,044,204 | B2 | 6/2015 | Riley et al. |
| 9,165,449 | B2 | 10/2015 | Ribble et al. |
| 9,213,956 | B2 | 12/2015 | Huster et al. |
| 9,311,540 | B2 | 4/2016 | Ecker et al. |
| 9,318,012 | B2 | 4/2016 | Johnson et al. |
| 9,320,444 | B2 | 4/2016 | Hayes et al. |
| 9,384,651 | B2 | 7/2016 | Hsu et al. |
| 9,408,561 | B2 | 8/2016 | Stone et al. |
| 9,427,178 | B2 | 8/2016 | Greene |
| 9,433,348 | B2 | 9/2016 | Eshelman et al. |
| 9,524,424 | B2 | 12/2016 | Greene |
| 9,538,158 | B1 | 1/2017 | Rush et al. |
| 9,552,460 | B2 | 1/2017 | Riley et al. |
| 9,619,997 | B2 | 4/2017 | Treacy et al. |
| 9,642,967 | B2 | 5/2017 | Ribble et al. |
| 9,711,029 | B2 | 7/2017 | Ribble et al. |
| 9,734,544 | B2 | 8/2017 | Kirkland et al. |
| 9,760,684 | B2 | 9/2017 | Humphrys et al. |
| 9,761,109 | B2 | 9/2017 | Ribble et al. |
| 9,763,629 | B2 | 9/2017 | King et al. |
| 9,833,194 | B2 | 12/2017 | Hayes et al. |
| 9,861,587 | B2 | 1/2018 | Rohrer et al. |
| 9,872,637 | B2 | 1/2018 | Kording et al. |
| 9,877,667 | B2 | 1/2018 | Doheny |
| 9,892,612 | B2 | 2/2018 | Smits et al. |
| 9,934,427 | B2 | 4/2018 | Derenne et al. |
| 9,937,090 | B2 | 4/2018 | Hayes et al. |
| 9,946,840 | B1 | 4/2018 | Kemp |
| 9,972,187 | B1 | 5/2018 | Srinivasan et al. |
| 9,978,244 | B2 | 5/2018 | Ribble et al. |
| 10,037,674 | B2 | 7/2018 | Ribble et al. |
| 10,052,062 | B2 | 8/2018 | De Sapio et al. |
| 10,055,961 | B1 | 8/2018 | Johnson et al. |
| 10,095,838 | B2 | 10/2018 | Hebler et al. |
| 10,121,070 | B2 | 11/2018 | Derenne et al. |
| 10,127,357 | B2 | 11/2018 | Whiting et al. |
| 10,140,833 | B1 | 11/2018 | Jacobson et al. |
| 10,157,536 | B2 | 12/2018 | Zuckerman et al. |
| 10,163,322 | B2 | 12/2018 | Ribble et al. |
| 10,206,630 | B2 | 2/2019 | Stone et al. |
| 10,210,470 | B2 | 2/2019 | Datta Ray |
| 10,226,187 | B2 | 3/2019 | Al-Ali et al. |
| 10,238,801 | B2* | 3/2019 | Wehba ................ G16H 40/20 |
| 2002/0049389 | A1* | 4/2002 | Abreu ..................... G02C 7/04 600/318 |
| 2002/0098947 | A1 | 7/2002 | Brown |
| 2003/0065020 | A1 | 4/2003 | Gale et al. |
| 2003/0139340 | A1 | 7/2003 | Creasey |
| 2003/0225664 | A1 | 12/2003 | Ohno et al. |
| 2005/0182305 | A1 | 8/2005 | Hendrich |
| 2005/0196817 | A1 | 9/2005 | Kingsmore et al. |
| 2005/0239150 | A1 | 10/2005 | Bergmann |
| 2006/0293265 | A1 | 12/2006 | Srivastava et al. |
| 2008/0009686 | A1 | 1/2008 | Hendrich |
| 2008/0161700 | A1 | 7/2008 | Sachanadani et al. |
| 2008/0186189 | A1 | 8/2008 | Azzaro et al. |
| 2008/0243787 | A1 | 10/2008 | Stading |
| 2008/0281638 | A1 | 11/2008 | Weatherly et al. |
| 2009/0069642 | A1 | 3/2009 | Gao et al. |
| 2009/0105550 | A1 | 4/2009 | Rothman et al. |
| 2009/0182593 | A1 | 7/2009 | Whitmore |

(56) References Cited

U.S. PATENT DOCUMENTS

| | | |
|---|---|---|
| 2009/0212925 A1 | 8/2009 | Schuman, Sr. et al. |
| 2009/0212956 A1 | 8/2009 | Schuman et al. |
| 2009/0214009 A1 | 8/2009 | Schuman, Sr. et al. |
| 2009/0216556 A1 | 8/2009 | Martin et al. |
| 2009/0217080 A1 | 8/2009 | Ferguson et al. |
| 2009/0278934 A1 | 11/2009 | Ecker et al. |
| 2010/0100962 A1 | 4/2010 | Boren |
| 2010/0131434 A1 | 5/2010 | Magent et al. |
| 2011/0067005 A1 | 3/2011 | Bassin et al. |
| 2011/0068935 A1 | 3/2011 | Riley et al. |
| 2011/0112442 A1 | 5/2011 | Meger et al. |
| 2011/0251520 A1 | 10/2011 | Shieh et al. |
| 2011/0288811 A1 | 11/2011 | Greene |
| 2011/0301432 A1 | 12/2011 | Riley et al. |
| 2011/0301440 A1 | 12/2011 | Riley et al. |
| 2012/0059672 A1 | 3/2012 | Romano et al. |
| 2012/0075464 A1 | 3/2012 | Derenne et al. |
| 2012/0092169 A1 | 4/2012 | Kaiser et al. |
| 2012/0095722 A1 | 4/2012 | Ten Kate |
| 2012/0102051 A1 | 4/2012 | Reville et al. |
| 2012/0149785 A1 | 6/2012 | Ryan et al. |
| 2012/0248395 A1 | 10/2012 | Stark et al. |
| 2012/0253233 A1 | 10/2012 | Greene et al. |
| 2012/0271654 A1 | 10/2012 | Croghan et al. |
| 2012/0314901 A1 | 12/2012 | Hanson et al. |
| 2012/0316892 A1 | 12/2012 | Huster et al. |
| 2013/0023798 A1 | 1/2013 | Greene et al. |
| 2013/0060512 A1 | 3/2013 | Greene |
| 2013/0064884 A1 | 3/2013 | Rohrer et al. |
| 2013/0110010 A1 | 5/2013 | Fuke et al. |
| 2013/0127620 A1 | 5/2013 | Siebers et al. |
| 2013/0152950 A1 | 6/2013 | Giap |
| 2013/0246088 A1 | 9/2013 | Huster et al. |
| 2013/0267791 A1 | 10/2013 | Halperin et al. |
| 2013/0283529 A1 | 10/2013 | Hayes et al. |
| 2013/0297350 A1 | 11/2013 | Gross et al. |
| 2013/0303860 A1 | 11/2013 | Bender et al. |
| 2013/0330745 A1 | 12/2013 | Komori |
| 2013/0338543 A1 | 12/2013 | Gegner et al. |
| 2013/0339921 A1 | 12/2013 | Bassin et al. |
| 2013/0342351 A1 | 12/2013 | Riley et al. |
| 2014/0004833 A1 | 1/2014 | Kiddie et al. |
| 2014/0022079 A1 | 1/2014 | Wilson et al. |
| 2014/0022081 A1 | 1/2014 | Ribble et al. |
| 2014/0024972 A1 | 1/2014 | Greene |
| 2014/0045758 A1 | 2/2014 | Goldberg et al. |
| 2014/0051073 A1 | 2/2014 | Ryan et al. |
| 2014/0066816 A1 | 3/2014 | McNames et al. |
| 2014/0074442 A1 | 3/2014 | Doheny |
| 2014/0142133 A1 | 5/2014 | Alverdy et al. |
| 2014/0244298 A1 | 8/2014 | Robinson et al. |
| 2014/0259414 A1 | 9/2014 | Hayes et al. |
| 2014/0266733 A1 | 9/2014 | Hayes et al. |
| 2014/0313340 A1 | 10/2014 | Ecker et al. |
| 2014/0324451 A1 | 10/2014 | Pesot et al. |
| 2014/0343889 A1 | 11/2014 | Ben Shalom et al. |
| 2014/0350884 A1 | 11/2014 | Greene |
| 2015/0005675 A1 | 1/2015 | Riley et al. |
| 2015/0032384 A1 | 1/2015 | Riley et al. |
| 2015/0109442 A1 | 4/2015 | Derenne et al. |
| 2015/0112151 A1 | 4/2015 | Muhsin et al. |
| 2015/0145691 A1 | 5/2015 | Eshelman et al. |
| 2015/0170494 A1 | 6/2015 | Hsu et al. |
| 2015/0173685 A1 | 6/2015 | Hughes et al. |
| 2015/0177260 A1 | 6/2015 | Anderberg et al. |
| 2015/0193583 A1 | 7/2015 | McNair et al. |
| 2015/0199892 A1 | 7/2015 | Johnson et al. |
| 2015/0201867 A1 | 7/2015 | Peindl et al. |
| 2015/0223761 A1 | 8/2015 | Meriheina et al. |
| 2015/0226764 A1 | 8/2015 | Ten Kate |
| 2015/0254412 A1 | 9/2015 | Humphrys et al. |
| 2015/0290060 A9 | 10/2015 | Hayes et al. |
| 2015/0293131 A1 | 10/2015 | Anderberg et al. |
| 2015/0305689 A1 | 10/2015 | Gourmelon et al. |
| 2015/0313552 A1 | 11/2015 | Zhang et al. |
| 2015/0332012 A1 | 11/2015 | Edelson et al. |
| 2015/0342538 A1 | 12/2015 | St. Pierre et al. |
| 2015/0363567 A1 | 12/2015 | Pettus |
| 2016/0045168 A1 | 2/2016 | Storer et al. |
| 2016/0055434 A1 | 2/2016 | Knipfer et al. |
| 2016/0085415 A1 | 3/2016 | Humphrys et al. |
| 2016/0100776 A1 | 4/2016 | Najaf et al. |
| 2016/0113551 A1 | 4/2016 | Annegarn et al. |
| 2016/0125716 A1 | 5/2016 | Ribble et al. |
| 2016/0136356 A1 | 5/2016 | Ribble et al. |
| 2016/0163187 A1 | 6/2016 | Treacy et al. |
| 2016/0174899 A1 | 6/2016 | Besnard et al. |
| 2016/0195544 A1 | 7/2016 | Kim |
| 2016/0213537 A1 | 7/2016 | Hayes et al. |
| 2016/0220153 A1 | 8/2016 | Annegarn et al. |
| 2016/0239611 A1 | 8/2016 | Heldt et al. |
| 2016/0282344 A1 | 9/2016 | Anderberg et al. |
| 2016/0321903 A1 | 11/2016 | Smits et al. |
| 2016/0357930 A1 | 12/2016 | Singh et al. |
| 2017/0000387 A1 | 1/2017 | Forth et al. |
| 2017/0039479 A1 | 2/2017 | Chen |
| 2017/0055851 A1 | 3/2017 | Al-Ali |
| 2017/0055917 A1 | 3/2017 | Stone et al. |
| 2017/0061089 A1 | 3/2017 | De Waele et al. |
| 2017/0065464 A1 | 3/2017 | Heil et al. |
| 2017/0073734 A1 | 3/2017 | Hancock et al. |
| 2017/0091355 A1 | 3/2017 | Hudson |
| 2017/0098359 A1 | 4/2017 | Sidhu et al. |
| 2017/0098360 A1 | 4/2017 | Ribble et al. |
| 2017/0155877 A1 | 6/2017 | Johnson et al. |
| 2017/0213145 A1 | 7/2017 | Pathak et al. |
| 2017/0220964 A1 | 8/2017 | Datta Ray |
| 2017/0235871 A1* | 8/2017 | Eden .................... G16B 20/00 703/2 |
| 2017/0237641 A1 | 8/2017 | Holeman et al. |
| 2017/0243459 A9 | 8/2017 | Sidhu et al. |
| 2017/0246063 A1 | 8/2017 | Monson et al. |
| 2017/0249821 A1 | 8/2017 | Coleman Boone et al. |
| 2017/0270766 A1 | 9/2017 | Ribble et al. |
| 2017/0277853 A1 | 9/2017 | Carlson et al. |
| 2017/0303849 A1 | 10/2017 | De Sapio et al. |
| 2017/0329920 A1 | 11/2017 | King et al. |
| 2017/0345275 A1 | 11/2017 | Ribble et al. |
| 2017/0360379 A1 | 12/2017 | Yang et al. |
| 2018/0021184 A1 | 1/2018 | Monson et al. |
| 2018/0061253 A1 | 3/2018 | Hyun |
| 2018/0064400 A1 | 3/2018 | Chbat et al. |
| 2018/0068179 A1 | 3/2018 | Derenne et al. |
| 2018/0082042 A1 | 3/2018 | Volyanskyy et al. |
| 2018/0082573 A1 | 3/2018 | Zuckerman et al. |
| 2018/0098739 A1 | 4/2018 | Freeman et al. |
| 2018/0110419 A1 | 4/2018 | Volpe et al. |
| 2018/0132756 A1 | 5/2018 | Kording et al. |
| 2018/0132794 A1 | 5/2018 | Lange |
| 2018/0137734 A1 | 5/2018 | Srinivasan et al. |
| 2018/0150606 A1 | 5/2018 | Arabi |
| 2018/0168516 A1 | 6/2018 | Pappada et al. |
| 2018/0177436 A1 | 6/2018 | Chang et al. |
| 2018/0182471 A1 | 6/2018 | Yelton et al. |
| 2018/0184984 A1 | 7/2018 | Zerhusen et al. |
| 2018/0228404 A1 | 8/2018 | Bhunia et al. |
| 2018/0228405 A1 | 8/2018 | Burwinkle et al. |
| 2018/0233018 A1 | 8/2018 | Burwinkel et al. |
| 2018/0264186 A1 | 9/2018 | Van Bruggen et al. |
| 2018/0277252 A1* | 9/2018 | Drenkard ............... G16H 50/20 |
| 2018/0308027 A1 | 10/2018 | Cline et al. |
| 2018/0310822 A1 | 11/2018 | Indorf et al. |
| 2018/0322760 A1 | 11/2018 | Ribble et al. |
| 2018/0325744 A1 | 11/2018 | Weidman et al. |
| 2018/0357879 A1 | 12/2018 | Negre et al. |
| 2019/0012893 A1 | 1/2019 | Johnson et al. |
| 2019/0029900 A1 | 1/2019 | Walton et al. |
| 2019/0034589 A1 | 1/2019 | Chen et al. |
| 2019/0051383 A1 | 2/2019 | Sherwin et al. |
| 2019/0060137 A1 | 2/2019 | Severns et al. |
| 2019/0099113 A1 | 4/2019 | Rder et al. |
| 2019/0108908 A1 | 4/2019 | Faulks et al. |
| 2019/0125241 A1 | 5/2019 | Patek |
| 2019/0307405 A1 | 10/2019 | Terry et al. |

(56) References Cited

U.S. PATENT DOCUMENTS

| | | |
|---|---|---|
| 2019/0336085 A1 | 11/2019 | Kayser et al. |
| 2020/0185074 A1* | 6/2020 | Czerska ................. G16H 10/60 |
| 2020/0253562 A1* | 8/2020 | Newberry ............ A61B 5/6838 |

FOREIGN PATENT DOCUMENTS

| | | |
|---|---|---|
| WO | 2017083353 A1 | 5/2017 |
| WO | 2017091726 A1 | 6/2017 |
| WO | 2017153120 A1 | 9/2017 |
| WO | 2017189957 A1 | 11/2017 |
| WO | 2018002769 A1 | 1/2018 |
| WO | 2018085563 A1 | 5/2018 |

OTHER PUBLICATIONS

International Search Report for PCT Patent Application No. PCT/US2019/026044 dated Aug. 2, 2019 (32 pages).

Extended European Search Report for European Patent Application No. 19168199.8 dated Sep. 10, 2019 (11 pages).

Australian Examination Report No. 1 for Standard Patent Application for Australian Patent Application No. 2019202495 dated Feb. 3, 2020 (5 pages).

Office Action issued by the Canadian Intellectual Property Office for Canadian Application No. 3,039,440, dated Jan. 18, 2021 (9 pages).

Examiner's Report issued in Canadian Patent Application No. 3,039,440 dated Oct. 14, 2021 (5 pages).

"Prediction of Sepsis in the Intensive Care Unit with Minimal Electronic Health Record Data: A Machine Learning Approach," by Thomas Desautels et al., JMIR Medical Informatics, Jul.-Sep. 2016, vol. 4, No. 3 (21 pages).

"VitalSync™ Early Warning Score (EWS) App," Medtronic, https://www.medtronic.com/covidien/en-us/products/health-informatics-and-monitoring/vital-sync-early-warning-score-app.html (5 pages).

"Philips IntelliVue Guardian Solution, Optimize your clinical workflow to improve patient care," Philips, https://www.philips.com.au/healthcare/clinical-solutions/automated-early-warning-scoring/intellivue-guardian-ews (11 pages).

* cited by examiner

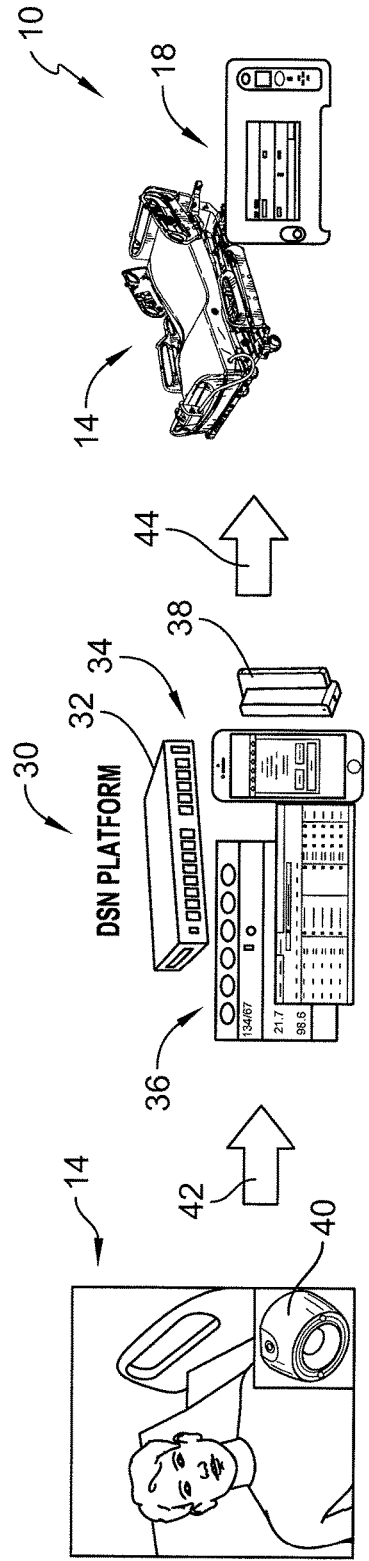
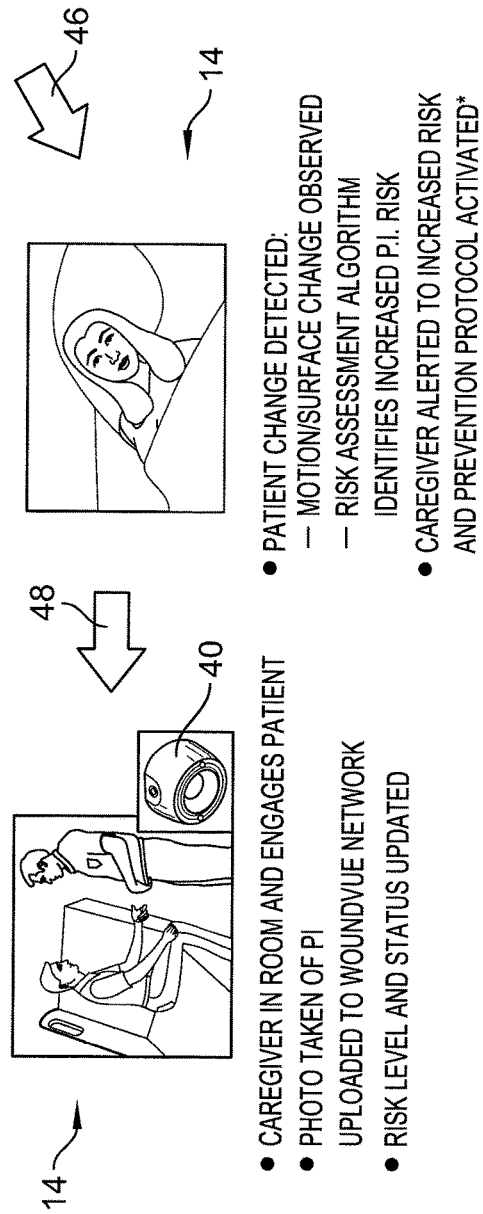
FIG. 2

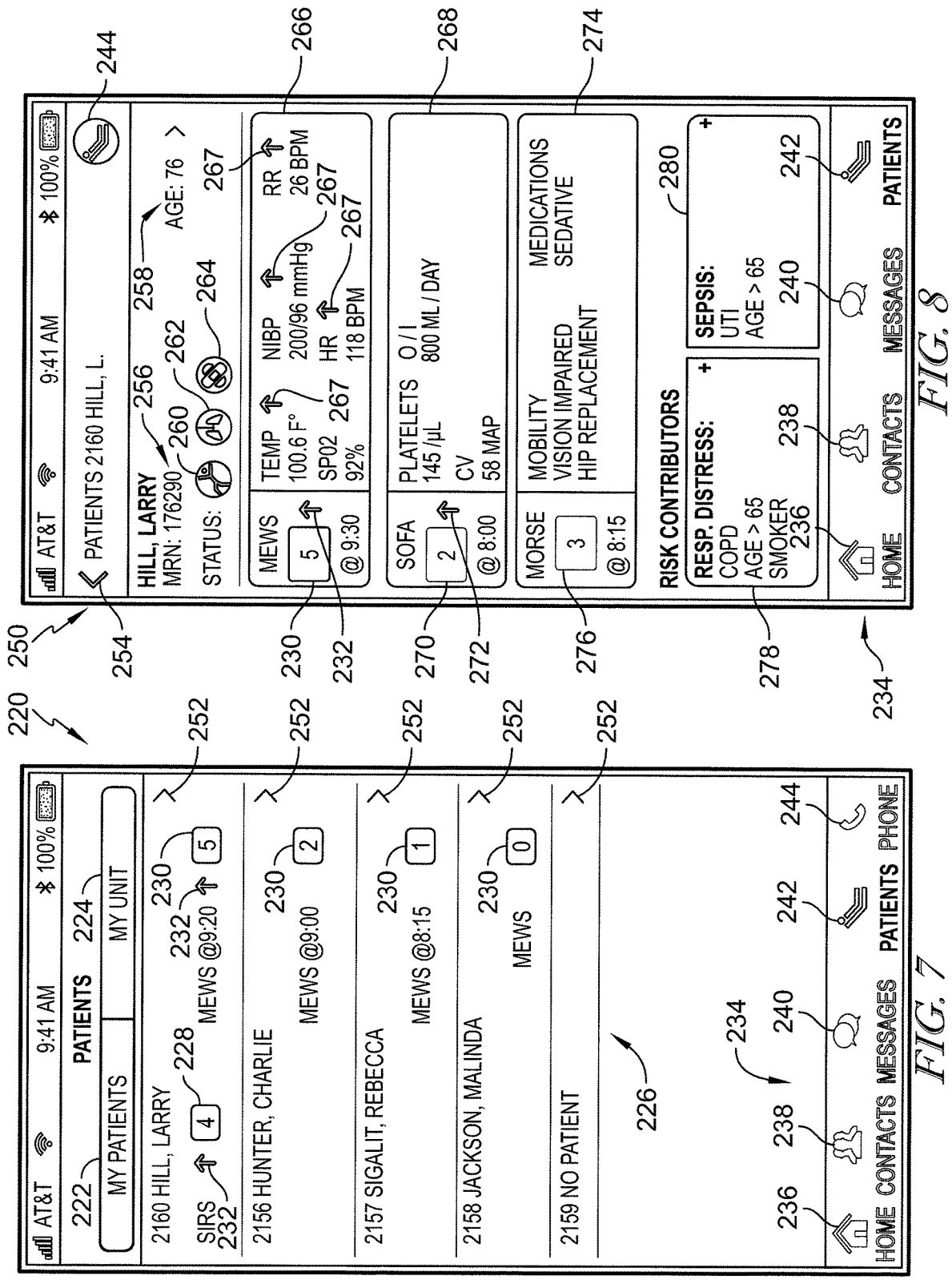

PATIENT RISK ASSESSMENT BASED ON DATA FROM MULTIPLE SOURCES IN A HEALTHCARE FACILITY

The present application claims the benefit, under 35 U.S.C. § 119(e), of U.S. Provisional Application No. 62/655,385, filed Apr. 10, 2018, which is hereby incorporated by reference herein in its entirety.

BACKGROUND

The present disclosure relates to assessing patient risk in a healthcare facility and particularly, to assessing patient risk based on data obtained from medical equipment. More particularly, the present disclosure relates to assessing multiple risks of a patient in a healthcare facility and notifying caregivers of the patient's multiple risks.

Patients in healthcare facilities are susceptible to multiple risks during their stays. For example, there is a risk of developing sepsis, a risk of developing pressure injuries such as pressure sores or decubitus ulcers, and a risk of falling while exiting a bed or after having exited the bed. Risk assessments of patients oftentimes take place on a sporadic basis with prolonged periods transpiring between the assessments. For example, vital signs may be charted into a patient's electronic medical record (EMR) once or twice per shift and so, four to eight hours or more may transpire between vitals charting. Furthermore, the results of risk assessments are sometimes only available at a limited number of locations in the healthcare facility such as at an EMR computer or at a computer of a master nurse station. Accordingly, there is a need in the healthcare field to have more timely information regarding risk assessments of patients and there is a need for the risk assessment information to be more readily available to caregivers.

SUMMARY

An apparatus, system, or method may comprise one or more of the features recited in the appended claims and/or the following features which, alone or in any combination, may comprise patentable subject matter:

According to a first aspect of the present disclosure, a system for use in a healthcare facility may be provided. The system may include an analytics engine and a plurality of equipment that may provide data to the analytics engine. The data may pertain to a patient in the healthcare facility. The plurality of equipment may include at least one of the following: a patient support apparatus, a nurse call computer, a physiological monitor, a patient lift, a locating computer of a locating system, and an incontinence detection pad. The analytics engine may analyze the data from the plurality of equipment to determine in substantially real time at least one of the following: a first score relating to a risk of the patient developing sepsis, a second score relating to a risk of the patient falling, and a third score relating to a risk of the patient developing a pressure injury. The system may further include a computer that may be coupled to the analytics engine and that may coordinate a caregiver rounding interval at which at least one caregiver assigned to the patient may be required to check in on the patient. The computer may automatically decrease the caregiver rounding interval in response to the at least one of the first, second, or third scores increasing from a first value to a second value and the computer may automatically increase the caregiver rounding interval in response to the at least one of the first, second, or third scores decreasing from the second value to the first value.

In some embodiments, the system of the first aspect may further include a plurality of displays that may be communicatively coupled to the analytics engine and that may be operable to display the at least two first, second, and third scores. For example, the plurality of displays may include at least two of the following: a status board display that may be located at a master nurse station, an in-room display that may be provided by a room station of a nurse call system, an electronic medical records (EMR) display of an EMR computer, and a mobile device display of a mobile device of a caregiver that may be assigned to the patient.

If desired, the plurality of equipment of the first aspect may include at least three of the following: the patient support apparatus, the nurse call computer, the physiological monitor, the patient lift, the locating computer, and the incontinence detection pad. Alternatively, the plurality of equipment of the first aspect may include at least four of the following: the patient support apparatus, the nurse call computer, the physiological monitor, the patient lift, the locating computer, and the incontinence detection pad. Further alternatively, the plurality of equipment of the first aspect may include at least five of the following: the patient support apparatus, the nurse call computer, the physiological monitor, the patient lift, the locating computer, and the incontinence detection pad. Still further alternatively, the plurality of equipment of the first aspect may include all six of the following: the patient support apparatus, the nurse call computer, the physiological monitor, the patient lift, the locating computer, and the incontinence detection pad.

Optionally, each of the first, second, and third scores of the first aspect may be normalized by the analytics engine so as to have a minimum value and a maximum value that may be common to each of the other first, second, and third scores. For example, the minimum value may be 0 for each of the first, second, and third scores. Alternatively, the minimum value may be 1 for each of the first, second, and third scores. Also, the maximum value may be 5 for each of the first, second, and third scores. It is within the scope of this disclosure for other minimum values, less than 0 (e.g., negative numbers), and greater than 5, to be used in connection with the first, second, and third scores.

In some embodiments of the first aspect, the analytics engine also may receive additional data from an international pressure ulcer prevalence (IPUP) survey for the patient and may analyze the additional data in connection with determining at least one of the first, second, and third scores. The analytics engine may communicate the at least two first, second, and third scores to at least one piece of equipment of the plurality of equipment. Optionally, the at least one piece of equipment of the plurality of equipment may include a device display and, if desired, steps for lowering at least one of the first, second, and third scores may be displayed on the device display.

According to the system of the first aspect, data from the patient support apparatus may include at least one patient vital sign that may be sensed by at least one vital sign sensor that may be integrated into the patient support apparatus. For example, the at least one patient vital sign that may be sensed by the at least one vital sign sensor may include heart rate or respiration rate. Data from the patient support apparatus further may include patient weight. Alternatively or additionally, data from the patient support apparatus may include patient weight and a position of the patient on the patient support apparatus. Further alternatively or additionally, data from the patient support apparatus may include data indicative of an amount of motion by the patient while supported on the patient support apparatus.

In some embodiments of the first aspect, data from the physiological monitor may include one or more of the following: heart rate data, electrocardiograph (EKG) data, respiration rate data, patient temperature data, pulse oximetry data, and blood pressure data. The system of the first aspect may be configured such that the first score may be at or near a maximum value if the following criteria exist: i) the patient's temperature is greater than about 38.3° Celsius (C) (about 101° Fahrenheit (F)) or less than about 35.6° C. (about 96° F.), ii) the patient's heart rate is greater than 90 beats per minute; and iii) the patient's respiration rate is greater than 20 respirations per minute.

If desired, the analytics engine of the first aspect may initiate a message to a mobile device of the at least one caregiver assigned to the patient if the first, second, or third score increases from a previous value. Alternatively or additionally, the analytics engine of the first aspect may initiate a message to a mobile device of the at least one caregiver assigned to the patient if the first, second, or third score reaches a threshold value. Optionally, the analytics engine also may receive additional data relating to at least one wound of the patient and may analyze the additional data in connection with determining at least one of the first, second, and third scores. For example, the additional data relating to the at least one wound may include an image of the at least one wound.

In some embodiments, the patient support apparatus of the first aspect may include a patient bed or a stretcher. The analytics engine also may receive additional data relating to at least one of the following: fluid input and output, cardiac output, comorbidities, and bloodwork, and wherein the analytics engine may analyze the additional data in connection with determining at least one of the first, second, and third scores. The physiological monitor of the first aspect may include at least one of the following: a wireless patch sensor that may be attached to the patient, an ambulatory cardiac monitor, an EKG, a respiration rate monitor, a blood pressure monitor, a pulse oximeter, and a thermometer. The plurality of equipment of the first aspect may further include a chair monitor to monitor patient movement while the patient is seated on a chair. Alternatively or additionally, the plurality of equipment of the first aspect may further include a toilet monitor to monitor patient movement while the patient is seated on a toilet.

According to a second aspect of the present disclosure, apparatus for assessing medical risks of a patient may include an analytics engine and a plurality of equipment that may provide data to the analytics engine. The plurality of equipment may include at least two of the following: a patient support apparatus, a nurse call computer, a physiological monitor, a patient lift, a locating computer of a locating system, and an incontinence detection pad. The analytics engine may analyze the data from the plurality of equipment to determine at least two of the following: a first score that may relate to a risk of the patient developing sepsis, a second score that may relate to a risk of the patient falling, and a third score that may relate to a risk of the patient developing a pressure injury. The apparatus may further include a plurality of displays that may be communicatively coupled to the analytics engine and that may be operable to display the at least two first, second, and third scores. The plurality of displays may include at least two of the following: a status board display that may be located at a master nurse station, an in-room display that may be provided by a room station of a nurse call system, an electronic medical records (EMR) display of an EMR computer, and a mobile device display of a mobile device of a caregiver that may be assigned to the patient.

In some embodiments, the plurality of equipment may include at least three of the patient support apparatus, the nurse call computer, the physiological monitor, the patient lift, the locating computer, and the incontinence detection pad. In further embodiments, the plurality of equipment may include at least four of the patient support apparatus, the nurse call computer, the physiological monitor, the patient lift, the locating computer, and the incontinence detection pad. In additional embodiments, the plurality of equipment may include at least five of the patient support apparatus, the nurse call computer, the physiological monitor, the patient lift, the locating computer, and the incontinence detection pad. In still other embodiments, the plurality of equipment includes all six of the patient support apparatus, the nurse call computer, the physiological monitor, the patient lift, the locating computer, and the incontinence detection pad.

Optionally, each of the first, second, and third scores may be normalized so as to have a minimum value and a maximum value that may be common to each of the other first, second, and third scores. For example, the minimum value may be 0 for each of the first, second, and third scores. Alternatively, the minimum value may be 1 for each of the first, second, and third scores. Similarly, the maximum value may be 5 for each of the first, second, and third scores. It is within the scope of this disclosure for other minimum values, less than 0 (e.g., negative numbers), and greater than 5, to be used in connection with the first, second, and third scores.

It is contemplated by this disclosure that a rounding protocol relating to caregiver rounds may be adjusted based on at least one of the first, second and third scores. For example, the rounding protocol that may be adjusted includes a rounding time interval relating to when the caregiver may be required to check on the patient.

If desired, the analytics engine also may receive additional data from an international pressure ulcer prevalence (IPUP) survey for the patient and may analyze the additional data in connection with determining at least one of the first, second, and third scores.

In some embodiments, the analytics engine may communicate the at least two first, second, and third scores to the plurality of equipment. At least one piece of equipment of the plurality of equipment may include a device display and steps for lowering at least one of the first, second, and third scores may be displayed on the device display.

Data from the patient support apparatus may include at least one patient vital sign that may be sensed by at least one vital sign sensor that may be integrated into the patient support apparatus. For example, the at least one patient vital sign that may be sensed by the at least one vital sign sensor may include heart rate or respiration rate. Alternatively or additionally, data from the patient support apparatus may include patient weight. Further alternatively or additionally, data from the patient support apparatus may include patient weight and a position of the patient on the patient support apparatus. Optionally, data from the patient support apparatus may include data indicative of an amount of motion by the patient while supported on the patient support apparatus.

The analytics engine may analyze the data from the plurality of equipment in substantially real time and may update the at least two first, second, and third scores in substantially real time. It is contemplated by this disclosure that data from the physiological monitor may include one or more of the following: heart rate data, electrocardiograph (EKG) data, respiration rate data, patient temperature data, pulse oximetry data, and blood pressure data.

In some embodiments, the first score may be at or near a maximum value if the following criteria exist: i) the patient's temperature is greater than about 38.3° Celsius (C) (about 101° Fahrenheit (F)) or less than about 35.6° C. (about 96° F.), ii) the patient's heart rate is greater than 90 beats per minute; and iii) the patient's respiration rate is greater than 20 respirations per minute.

Optionally, the analytics engine may initiate a message to the mobile device of the caregiver assigned to the patient if the first, second, or third score increases from a previous value. Alternatively or additionally, the analytics engine may initiate a message to the mobile device of the caregiver assigned to the patient if the first, second, or third score reaches a threshold value.

In some embodiments, the analytics engine also may receive additional data relating to at least one wound of the patient and may analyze the additional data in connection with determining at least one of the first, second, and third scores. The additional data relating to the at least one wound may include an image of the at least one wound, for example.

The patient support apparatus may include a patient bed or a stretcher, for example. If desired, the analytics engine also may receive additional data relating to at least one of the following: fluid input and output, cardiac output, comorbidities, and bloodwork. The analytics engine may analyze the additional data in connection with determining at least one of the first, second, and third scores.

In some embodiments, the physiological monitor may include at least one of the following: a wireless patch sensor that may be attached to the patient, an ambulatory cardiac monitor, an EKG, a respiration rate monitor, a blood pressure monitor, a pulse oximeter, and a thermometer. Alternatively or additionally, the plurality of equipment also may include a chair monitor to monitor patient movement while the patient is seated on a chair. Further alternatively or additionally, the plurality of equipment further may include a toilet monitor to monitor patient movement while the patient is seated on a toilet.

According to a third aspect of the present disclosure, apparatus for assessing medical risks of a patient may include an analytics engine and a plurality of equipment that may provide data to the analytics engine. The plurality of equipment may include at least two of the following: a patient support apparatus, a nurse call computer, a physiological monitor, a patient lift, a locating computer of a locating system, and an incontinence detection pad. The analytics engine may analyze the data from the plurality of equipment to determine each of the following: a first score that may relate to a risk of the patient developing sepsis, a second score that may relate to a risk of the patient falling, and a third score that may relate to a risk of the patient developing a pressure injury. The apparatus may further include a plurality of displays that may be communicatively coupled to the analytics engine. At least one display of the plurality of displays may be operable to display the first, second, and third scores.

In some embodiments, the at least one display may include at least one of the following: a status board display that may be located at a master nurse station, an in-room display that may be provided by a room station of a nurse call system, an electronic medical records (EMR) display of an EMR computer, and a mobile device display of a mobile device of a caregiver assigned to the patient. In additional embodiments, the at least one display may include at least two of the following: a status board display that may be located at a master nurse station, an in-room display that may be provided by a room station of a nurse call system, an electronic medical records (EMR) display of an EMR computer, and a mobile device display of a mobile device of a caregiver assigned to the patient. In further embodiments, the at least one display may include at least three of the following: a status board display that may be located at a master nurse station, an in-room display that may be provided by a room station of a nurse call system, an electronic medical records (EMR) display of an EMR computer, and a mobile device display of a mobile device of a caregiver assigned to the patient. In still other embodiments, the at least one display may include all four of the following: a status board display that may be located at a master nurse station, an in-room display that may be provided by a room station of a nurse call system, an electronic medical records (EMR) display of an EMR computer, and a mobile device display of a mobile device of a caregiver assigned to the patient.

In some embodiments, the apparatus of the third aspect set forth above in paragraph [0027] may be provided in combination with any one or more of the features set forth above in the various sentences of paragraphs [0015] through [0026].

According to a fourth aspect of the present disclosure, a method for assessing medical risks of a patient may include receiving at an analytics engine data from a plurality of equipment. The plurality of equipment may include at least two of the following: a patient support apparatus, a nurse call computer, a physiological monitor, a patient lift, a locating computer of a locating system, and an incontinence detection pad. The method may further include analyzing with the analytics engine the data from the plurality of equipment to determine at least two of the following: a first score that may relate to a risk of the patient developing sepsis, a second score that may relate to a risk of the patient falling, and a third score that may relate to a risk of the patient developing a pressure injury. The method also may include displaying at a plurality of displays that may be communicatively coupled to the analytics engine the at least two of the first, second, and third scores. The plurality of displays may include at least two of the following: a status board display that may be located at a master nurse station, an in-room display that may be provided by a room station of a nurse call system, an electronic medical records (EMR) display of an EMR computer, and a mobile device display of a mobile device of a caregiver assigned to the patient.

In some embodiments, the plurality of equipment may include at least three of the patient support apparatus, the nurse call computer, the physiological monitor, the patient lift, the locating computer, and the incontinence detection pad. In further embodiments, the plurality of equipment may include at least four of the patient support apparatus, the nurse call computer, the physiological monitor, the patient lift, the locating computer, and the incontinence detection pad. In additional embodiments, the plurality of equipment may include at least five of the patient support apparatus, the nurse call computer, the physiological monitor, the patient lift, the locating computer, and the incontinence detection pad. In still other embodiments, the plurality of equipment may include all six of the patient support apparatus, the nurse call computer, the physiological monitor, the patient lift, the locating computer, and the incontinence detection pad.

Optionally, the method may further include, with the analytics engine, normalizing each of the first, second, and third scores so as to have a minimum value and a maximum value that may be common to each of the other first, second, and third scores. For example, the minimum value may be 0 for each of the first, second, and third scores. Alternatively, the minimum value may be 1 for each of the first, second, and third scores. If desired, the maximum value may be 5 for each of the first, second, and third scores. It is within the scope of this disclosure for other minimum values, less than 0 (e.g., negative numbers), and greater than 5, to be used in connection with the first, second, and third scores.

In some embodiments, the method may further include adjusting a rounding protocol that may relate to caregiver rounds based on at least one of the first, second and third scores. For example, the rounding protocol that may be adjusted may include a rounding time interval that may relate to when the caregiver is required to check on the patient.

If desired, the method may further include receiving at the analytics engine additional data from an international pressure ulcer prevalence (IPUP) survey for the patient and analyzing with the analytics engine the additional data in connection with determining at least one of the first, second, and third scores. The method may also include communicating the at least two first, second, and third scores from the analytics engine to the plurality of equipment. At least one piece of equipment of the plurality of equipment may include a device display and the method may further include displaying on the device display steps for lowering at least one of the first, second, and third scores.

In some embodiments of the method, data from the patient support apparatus may include at least one patient vital sign that may be sensed by at least one vital sign sensor that may be integrated into the patient support apparatus. For example, the at least one patient vital sign that may be sensed by the at least one vital sign sensor may include heart rate or respiration rate. Alternatively or additionally, data from the patient support apparatus further may include patient weight. Further alternatively or additionally, data from the patient support apparatus may include patient weight and a position of the patient on the patient support apparatus. Still further alternatively or additionally, data from the patient support apparatus may include data indicative of an amount of motion by the patient while supported on the patient support apparatus.

In some embodiments, analyzing the data with the analytics engine may include analyzing the data in substantially real time and the method further may include updating the at least two first, second, and third scores in substantially real time. Data from the physiological monitor may include one or more of the following: heart rate data, electrocardiograph (EKG) data, respiration rate data, patient temperature data, pulse oximetry data, and blood pressure data. It is contemplated by this disclosure that the first score may be at or near a maximum value if the following criteria exist: i) the patient's temperature is greater than about 38.3° Celsius (C) (about 101° Fahrenheit (F)) or less than about 35.6° C. (about 96° F.), ii) the patient's heart rate is greater than 90 beats per minute; and iii) the patient's respiration rate is greater than 20 respirations per minute.

Optionally, the method further may include initiating with the analytics engine a message to the mobile device of the caregiver assigned to the patient if the first, second, or third score increases from a previous value. Alternatively or additionally, the method further may include initiating with the analytics engine a message to the mobile device of the caregiver assigned to the patient if the first, second, or third score reaches a threshold value.

If desired, the method further may include receiving at the analytics engine additional data that may relate to at least one wound of the patient and analyzing with the analytics engine the additional data in connection with determining at least one of the first, second, and third scores. For example, the additional data that may relate to the at least one wound may include an image of the at least one wound.

The patient support apparatus may include a patient bed or a stretcher. Optionally, the method further may include receiving at the analytics engine additional data relating to at least one of the following: fluid input and output, cardiac output, comorbidities, and bloodwork, and analyzing with the analytics engine the additional data in connection with determining at least one of the first, second, and third scores.

In some embodiments of the method, the physiological monitor may include at least one of the following: a wireless patch sensor that may be attached to the patient, an ambulatory cardiac monitor, an EKG, a respiration rate monitor, a blood pressure monitor, a pulse oximeter, and a thermometer. Alternatively or additionally, the plurality of equipment of the method further may include a chair monitor to monitor patient movement while the patient is seated on a chair. Further alternatively or additionally, the plurality of equipment of the method further may include a toilet monitor to monitor patient movement while the patient is seated on a toilet.

According to a fifth aspect of the present disclosure, a method for assessing medical risks of a patient may include receiving at an analytics engine data from a plurality of equipment. The plurality of equipment may include at least two of the following: a patient support apparatus, a nurse call computer, a physiological monitor, a patient lift, a locating computer of a locating system, and an incontinence detection pad. The method further may include analyzing with the analytics engine the data from the plurality of equipment to determine each of the following: a first score that may relate to a risk of the patient developing sepsis, a second score that may relate to a risk of the patient falling, and a third score that may relate to a risk of the patient developing a pressure injury. The method also may include displaying on at least one display of a plurality of displays communicatively coupled to the analytics engine the first, second, and third scores.

In some embodiments of the method, the at least one display may include at least one of the following: a status board display that may be located at a master nurse station, an in-room display that may be provided by a room station of a nurse call system, an electronic medical records (EMR) display of an EMR computer, and a mobile device display of a mobile device of a caregiver assigned to the patient. In further embodiments of the method, the at least one display may include at least two of the following: a status board display that may be located at a master nurse station, an in-room display that may be provided by a room station of a nurse call system, an electronic medical records (EMR) display of an EMR computer, and a mobile device display of a mobile device of a caregiver assigned to the patient. In additional embodiments of the method, the at least one display may include at least three of the following: a status board display that may be located at a master nurse station, an in-room display that may be provided by a room station of a nurse call system, an electronic medical records (EMR) display of an EMR computer, and a mobile device display of a mobile device of a caregiver assigned to the patient. In still other embodiments of the method, the at least one display may include all four of the following: a status board display that may be located at a master nurse station, an in-room display that may be provided by a room station of a nurse call system, an electronic medical records (EMR) display of an EMR computer, and a mobile device display of a mobile device of a caregiver assigned to the patient.

In some embodiments, the method of the fifth aspect set forth above in paragraph [0041] may be provided in combination with any one or more of the features set forth above in the various sentences of paragraphs [0031] through [0040].

According to a sixth aspect of the present disclosure, a method of assessing medical risks of a patient may include receiving at an analytics engine patient demographics data of the patient including at least one of age, race, and weight. The method of the sixth aspect may also include receiving at the analytics engine comorbidity data of the patient including data indicating that the patient has at least one of the following medical conditions: acquired immunodeficiency syndrome (AIDS), anemia, chronic congestive heart failure, asthma, cancer, chronic obstructive pulmonary disease (COPD), coronary artery disease, cystic fibrosis, dementia, emphysema, alcohol or drug abuse, stroke, pulmonary emboli, a history of sepsis, type 1 diabetes, morbid obesity, neuromuscular disease, prior intubation, scoliosis, smoker, delirium, asplenic, bone marrow transplant, cirrhosis, dialysis, diverticulosis, heart valve disorders, inflammatory bowel disease, joint replacement, leukopenia, malignancy, neoplasm, organ transplant, peripheral vascular disease, renal disease, pressure injury, recent abortion, recent childbirth, seizures, sickle cell anemia, or terminal illness. The method of the sixth aspect may further include receiving at the analytics engine physiological data that may be measured by a physiological monitor that may have at least one sensor coupled to, or in communication with, the patient. The physiological data may be dynamic and changing over time while the patient is being monitored by the physiological monitor. Still further, the method of the sixth aspect may include using the analytics engine to calculate a risk score of the patient in substantially real time based on the patient demographics data, the comorbidity data, and the physiological data.

In some embodiments, the method of the sixth aspect further may include receiving at the analytics engine laboratory data of the patient and using the laboratory data in connection with calculating the risk score. Optionally, the laboratory data may include data that may pertain to one or more of the following: albumin, arterial partial pressure of oxygen (arterial PaO2), arterial partial pressure of carbon dioxide (PCO2), arterial pH, acidosis, brain natriuretic peptide, blood urea nitrogen, cardiac ejection fraction, creatinine, hemoglobin, hematocrit, lactate, pulmonary function test, troponin, bilirubin, C-reactive protein, D-dimer, glucose, bicarbonate (HCO3), hyperlactatemia, international normalization ration ratio (INR) for blood clotting, normal white blood count (WBC) with greater than 10% neutrophils, arterial partial pressure of carbon dioxide (PaCO2), fluid overload, Ph, platelets, procalcitonin, protein in urine, partial thromboplastin time (PTT) or white blood cell count.

Alternatively or additionally, the method of the sixth aspect further may include receiving at the analytics engine patient symptoms data of the patient and using the patient symptoms data in connection with calculating the risk score. Optionally, the patient symptoms data may include data that may pertain to one or more of the following: accessory muscle use, altered mental status, confusion, anxiety, chest pain, cough, cyanosis, diaphoresis, dyspnea, hemoptysis, fatigue, restlessness, sputum production, tachycardia, tachypnea, or lethargy.

Further alternatively or additionally, the method of the sixth aspect further may include receiving at the analytics engine clinical examination data and using the clinical examination data in connection with calculating the risk score. Optionally, the clinical examination data may include data pertaining to one or more of the following: abdominal respirations, abnormal lung sounds, accessory muscle use, capillary refill, chest pressure or pain, abnormal electrocardiograph (ECG), cough, cyanosis, decreased level of consciousness (LOC), agitation, encephalopathy, mottling, need for assistance with activities of daily living (ADLS), orthopnea, peripheral edema, sputum production, delirium, fluid overload, cardiac output, early state warm red skin and late state cool and pale with mottling, fever, headache, stiff neck, hypothermia, ileus, jaundice, meningitis, oliguria, peripheral cyanosis, petechial rash, positive fluid balance, seizures, stupor, or volume depletion.

Still further alternatively or additionally, the method of the sixth aspect further may include receiving at the analytics engine charted doctor's orders data and using the charted doctor's order data in connection with calculating the risk score. Optionally, the charted doctor's orders data may include data that may pertain to one or more of the following: delivery of breathing air other than with a cannula including with a Venturi, a rebreather, a non-rebreather, a continuous positive airway pressure (CPAP) machine, and a bi-level positive airway pressure (bi-PAP) machine; testing of arterial blood gases; testing of brain natriuretic peptide; breathing treatments; chest x-ray; Doppler echocardiography; high fluid rates or volumes (input and output (I&O)); pulmonary consultation; pulmonary function testing; ventilation-perfusion (VQ) scan; or thoracic computerized tomography (CT) scan.

In some embodiments, the method of the sixth aspect may further include receiving at the analytics engine admission data for the patient and using the admission data in connection with calculating the risk score. Optionally, the admission data may include data that may pertain to one or more of the following: abdominal aortic aneurysm surgery, acute myocardial ischemia, acute pancreatitis, aspiration, asthma, bronchiectasis, atelectasis, bronchitis, burns, cancer, cardiac or thoracic surgery, cardiac valve disorder or valvular insufficiency, chemo therapy, congestive heart failure, COPD exacerbation, deep vein thrombosis, drug overdose, dyspnea at rest, emergency surgery, hemoptysis, interstitial lung disease, lung abscess, neck surgery, neuro surgery, upper abdomen surgery, peripheral vascular surgery, pneumonia, pneumothorax, pulmonary emboli, pulmonary hypertension, pulmonary-renal syndrome, renal failure, sepsis, shock, sleep apnea, smoke inhalation injury, surgery, thoracentesis, trauma, lethargy, delirium, abscess, abdominal pain, abdominal tenderness, acute lung injury, appendicitis, bacteremia, cellulitis, cholangitis, cholecystitis, colitis, cystitis, dehydration, diverticulitis, encephalitis, encephalopathy, endocarditis, fever of unknown origin, gastroenteritis, gastrointestinal bleed, gastrointestinal tract infection, hypotension, infectious process, malaise, osteomyelitis, ostomy, pelvic pain, renal disease, pyelonephritis, respiratory infection, septic arthritis, soft tissue infection, surgical admission, wound, or acute respiratory distress syndrome.

Alternatively or additionally, the method of the sixth aspect further may include receiving at the analytics engine medications data for the patient and using the medications data in connection with calculating the risk score. Optionally, the medications data may include data that may pertain to one or more of the following: anticoagulants including heparin or levenox that may be delivered intravenously (IV) or subcutaneously (SC), bronchodilators, corticosteroids, diuretic use, high fluid rates or volumes or hypertonic fluids, opioids, sedatives, hypnotics, muscle relaxants, fluid overload, antibiotics, or immunosuppressants.

In some embodiments, the method of the sixth aspect may further include determining with the analytics engine that the patient may be at risk of developing respiratory distress if the patient is 70 years of age or older and has COPD. Alternatively or additionally, the method of the sixth aspect further may include determining with the analytics engine that the patient may be at risk of developing respiratory distress if the patient has COPD and has been prescribed opioids. Further alternatively or additionally, the method of the sixth aspect further may include determining with the analytics engine that the patient may be at risk of developing respiratory distress if the patient is 70 years of age or older and has been prescribed opioids. Still further alternatively or additionally, the method of the sixth aspect further may include determining with the analytics engine that the patient may be at risk of developing respiratory distress if the patient is 70 years of age or older, has asthma, and has a blood urea nitrogen (BUN) of greater than or equal to 30 milligrams (mg) per 100 milliliters (ml) of blood.

If desired, the method of the sixth aspect further may include determining with the analytics engine that the patient may be at risk of developing sepsis if the patient is 65 years of age or older and has cancer. Alternatively or additionally, the method of the sixth aspect further may include determining with the analytics engine that the patient may be at risk of developing sepsis if the patient has a history of developing sepsis. Further alternatively or additionally, the physiological data of the sixth method may include one or more of the following: heartrate, respiration rate, temperature, mean arterial pressure, systolic blood pressure, or pulse oximetry data including peripheral capillary oxygen saturation (SpO2).

According to a seventh aspect of the present disclosure, a method implemented on at least one computer may include receiving dynamic clinical variables and vital signs information of a patient, using the vital signs information to develop prior vital signs patterns and current vital signs patterns, and comparing the prior vital signs patterns with the current vital signs patterns. The method of the seventh aspect further may include receiving one or more of the following: static variables of the patient, subjective complaints of the patient, prior healthcare utilization patterns of the patient, or social determinants of health data of the patient. The method of the seventh aspect also may include using the dynamic clinical variables, the vital signs information, the results of the comparison of the prior vital signs patterns with the current vital signs patterns, and the one or more of the static variables, the subjective complaints, the healthcare utilization patterns, or the social determinants of health data in an algorithm to detect or predict that the patient has sepsis or is likely to develop sepsis.

In some embodiments of the method of the seventh aspect, the dynamic clinical variables may include point-of-care lab data. Optionally, the static variables may include comorbidities. Alternatively or additionally, the static variables may include whether the care setting of the patient is a pre-acute care setting, an acute care setting, or a post-acute care setting. If desired, the method of the seventh aspect further may include receiving historical data of the patient.

It is within the scope of the present disclosure that the method of the seventh aspect further may include outputting one or more recommended actions to one or more clinicians of the patient. For example, the one or more recommended actions may include sending the patient to an emergency department (ED). Alternatively or additionally, the one or more recommended actions may include increasing monitoring of the patient by the one or more clinicians. Further alternatively or additionally, the one or more recommended actions may include ordering a set of labs for the patient.

In some embodiments, the method of the seventh aspect further may include ranking clinicians of a healthcare facility. For example, ranking the clinicians of the healthcare facility may include ranking the clinicians by experience. Alternatively or additionally, ranking the clinicians of the healthcare facility may include ranking the clinicians by actions previously taken. Further alternatively or additionally, ranking the clinicians of the healthcare facility may include ranking the clinicians by prior patient outcomes. If desired, therefore, ranking the clinicians of the healthcare facility may include ranking the clinicians by experience, by actions previously taken, and by prior patient outcomes. Optionally, the actions that may have greatest impact on outcomes may be used by the at least one computer to inform newer or less experienced clinicians how an experienced clinician may attend to the patient.

In some embodiments of the system of the first aspect, a risk determination may be made or one or more of the first, second, or third risk scores may be calculated based on one or more of the data elements listed below in Table 11.

In some embodiments of the apparatus of the second aspect or the third aspect, a risk determination may be made or one or more of the first, second, or third risk scores may be calculated based on one or more of the data elements listed below in Table 11.

In some embodiments of the method of the fourth aspect or the fifth aspect, the method may further include making a risk determination or calculating one or more of the first, second, or third risk scores based on one or more of the data elements listed below in Table 11.

In some embodiments of the method of the sixth aspect, the method may further include calculating the risk score or making a risk determination based on one or more of the data elements listed below in Table 11.

In some embodiments of the method of the seventh aspect, the method may further include calculating a risk score or making a risk determination based on one or more of the data elements listed below in Table 11.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which:

FIG. 2 is a diagrammatic view of a system, similar to FIG. 1, showing in a top row, from left to right, a patient supported on a patient bed, an analytics engine (labeled as "DSN platform" in FIG. 2) receiving data from the patient bed, the analytics engine communicating risk assessment messages back to the patient bed and to a vital signs monitor, and showing in a second row, from right to left, the patient bed monitoring patient position, and a caregiver taking a picture of a pressure injury of the patient;

FIG. 7 is a screen shot example of a Patient screen of a mobile application of the mobile devices of FIGS. 3 and 6, showing the Patient screen including a list of patient names assigned to a caregiver that carries the mobile device, a room number to the left of each patient name, and risk scores including, when applicable, a systemic inflammatory response syndrome (SIRS) value and a modified early warning score (MEWS) value, beneath each of the patient names;

FIG. 8 is a screen shot example of a Risk Details screen that, beneath the patient's name, includes a MEWS window having additional information pertaining to the MEWS value, a Sepsis-Related Organ Failure Assessment (SOFA) window having additional information pertaining to a SOFA score, and a MORSE window having additional information pertaining to a MORSE Fall Scale (MFS) value, and that also includes a pair of Risk Contributors windows including a respiratory distress window listing factors contributing to a risk that the patient will experience respiratory distress and a sepsis window listing factors contributing to the patient's risk of developing sepsis;

DETAILED DESCRIPTION

Figure 1:
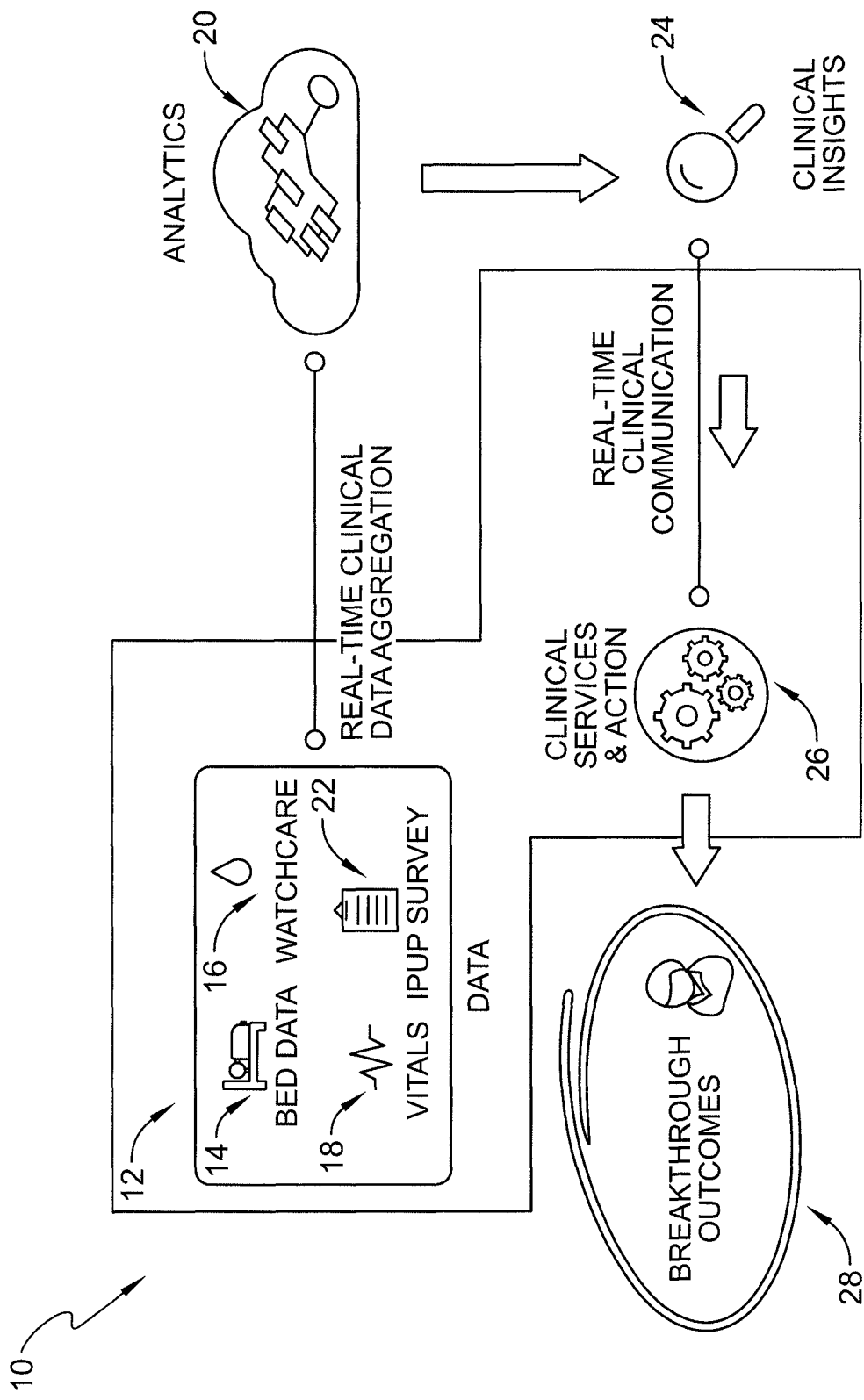
FIG. 1 is a diagrammatic view of a system showing bed data, incontinence detection system data, vital signs data, and data from an international pressure ulcer prevalence (IPUP) survey being provided to an analytics engine and showing the analytics engine initiating real-time clinical communication to caregivers based on an analysis of the received data.

An apparatus or system 10 includes sources 12 of patient data that communicate with an analytics engine 20 in substantially real time for real-time clinical data aggregation as shown diagrammatically in FIG. 1. In the illustrative example of FIG. 1, the sources 12 of patient data include a patient bed 14, an incontinence detection system 16, a vital signs monitor 18, and an international pressure ulcer prevalence (IPUP) survey 22. Bed data from patient bed 14 includes, for example, data indicating whether bed siderails are up or down, data indicating whether caster brakes are set, data indicating an angle at which a head section of a mattress support deck is elevated, data indicating whether or not an upper frame of the patient bed 14 is at its lowest height relative to a base frame of the bed 14, and other bed data as is known to those skilled in the art. See U.S. Patent Application Publication No. 2012/0316892 A1, which is hereby incorporated by reference herein, particularly with regard to Table 1, for additional examples of bed data.

Some embodiments of patient bed 14 have a weigh scale system that senses patient weight and that, in some embodiments, also monitors a position of a patient while supported on bed 14. See, for example, U.S. Pat. No. 7,253,366 which is hereby incorporated by reference herein in its entirety to the extent not inconsistent with the present disclosure which shall control as to any inconsistencies. Some embodiments of patient bed 14 also include integrated vital signs sensors to sense the patient's heart rate or respiration rate. See, for example, U.S. Patent Application Publication No. 2018/0184984 A1, which is hereby incorporated by reference herein in its entirety to the extent not inconsistent with the present disclosure which shall control as to any inconsistencies. Thus, patient weight data, patient position data, and vital signs data sensed by one or more on-bed sensors is also among the data that bed 14 transmits to analytics engine 20 in some embodiments.

In some embodiments, the incontinence detection system 16 is the WATCHCARE™ incontinence detection system available from Hill-Rom Company, Inc. Additional details of suitable incontinence detection systems 16 can be found in U.S. Patent Application Publication Nos. 2017/0065464 A1; 2017/0246063 A1; 2018/0021184 A1; 2018/0325744 A1 and 2019/0060137 A1, each of which is hereby incorporated herein by reference in its entirety to the extent not inconsistent with the present disclosure which shall control as to any inconsistencies. The incontinence detection system 16 communicates to analytics engine 20 data indicating whether an incontinence detection pad of system 16 that is placed underneath the patient is wet or dry.

In some embodiments, the incontinence detection pad of system 16 has a passive RFID tag that is activated by energy transmitted from one or more antennae that are situated beneath a mattress of patient bed 14 and on top of a mattress support deck of patient bed 14. Backscattered data from the passive RFID tag is read by one or more of these same antennae. A reader is provided to control which antenna of a plurality of antennae is the transmit antenna at any given instance, with the remaining antennae being receive antennae. The backscattered data received by the reader via the receive antennae is communicated to the analytics engine 20 via the reader, such as via a wireless transmission from the reader to a wireless access point of an Ethernet of the healthcare facility, or via the circuitry of bed 14 in those embodiments in which the reader is communicatively coupled to the bed circuitry such as via a wired connection.

Vital signs monitors 18 include, for example, electrocardiographs (ECG's or EKG's), electroencephalographs (EEG's), heart rate monitors, respiration rate monitors, temperature monitors, pulse oximeters, blood pressure monitors, and the like. Monitors 18 are standalone devices in some embodiments that are separate from bed 14. In some embodiments, at least one of the vital sign monitors 18 is the CONNEX® Spot Monitor available from Welch Allyn, Inc. of Skaneateles Falls, N.Y. As noted above, bed 14 includes its own integrated vital signs sensors in some embodiments. Thus, vital signs data provided to analytics engine 20 from vital signs monitors 18 or from bed 14 includes any one or more of the following: heart rate data, respiration rate data, temperature data, pulse oximetry data, blood pressure data, and the like.

The IPUP survey 22 includes information such as the following: 1) unit in which the patient is located, 2) patient age, 3) sex of the patient, 4) whether the patient is incontinent, 5) whether the patient has incontinence associated dermatitis, 6) whether an incontinence detection pad of system 16 is being used, 7) length of the patient's stay since admission to the healthcare facility, 8) the type of surface (e.g., mattress) on the patient's bed 14, 9) number of layers of linen (including diapers and briefs) between the patient and the support surface, 10) the type of linen used, 11) the patient's mobility status (e.g., completely immobile, makes small weight shifts but unable to turn to side, turns to side on own but requires help to stand, or independent), 12) observed position (e.g., on back, on side, prone, chair, or standing), 13) whether a patient lift has been used during the patient's stay, 14) whether the patient's heels are elevated when in bed, 15) patient's height (or length for infants), 16) patient's weight, 17) neonatal weight (in grams), 18) time spent in the emergency room (ER), 19) time spent in the operating room (OR), 20) whether the patient's skin was assessed within 24 hours of admission, 21) whether a pressure injury assessment was documented within 24 hours of admission, 22) the risk methodology used at admission, 23) the risk score(s) determined during admission, 24) the most recent or current risk methodology used, 25) the most recent or current risk score(s), 26) documentation of last risk assessment (e.g., time since last pressure ulcer/injury risk assessment prior to the current survey and whether the last risk assessment was documented), 27) whether the patient was determined to be at risk for pressure injuries, 28) whether pressure injury prevention protocols have been in effect for the last 24 hours for an at risk patient, 29) whether a skin assessment was documented within the past 24 hours, 30) whether a pressure redistribution surface was used within the past 24 hours, 31) whether patient repositioning as prescribed has occurred within the past 24 hours, 32) whether the patient has received nutritional support within the past 24 hours, 33) moisture management has been used for the patient in the past 24 hours (e.g., used of a low airloss feature or microclimate management feature of a surface), 34) whether patient restraints are in use, 35) the type of restraint being used, 36) the category of restraint being used, 37) the justification for use of the restraint, 38) whether Continuous Veno-Venous Hemofiltration (CVVH)/Continuous Venovenous Hemodiafiltration (CVHD)/Femoral Lines are being used with the patient, 39) whether the patient has diabetes, 40) whether Extracorporeal Membrane Oxygenation (ECMO) is being used with the patient, 41) whether the patient has sepsis, 42) whether the patient has vascular disease, 43) whether vasopressors are being used for the patient or whether the patient has low mean arterial pressure (MAP), 44) whether the patient is ventilated, 45) whether the patient has a pressure injury, 46) pressure injury detail (e.g., location of wound such as right or left heel, sacrum, scapula, etc.; the stage of each wound; whether each wound was present at admission; whether each wound was present on arrival at the unit; and wound documentation), 47) whether any pressure injury is device related, 48) the type of device (if answer to 47 was "yes"), and 49) number of days from admission until the pressure injury was documented (if pressure injury was facility-acquired). The data from the IPUP survey is among the data communicated to the analytics engine 20. It should be appreciated that the IPUP survey data is input by a caregiver using a PC or tablet computer or some other computer device.

According to the present disclosure, the analytics engine 20 processes the data received from sources 12 and performs risk assessments for the associated patient. As discussed in further detail below, the risk assessments include determining the risk of the patient developing sepsis, the risk of the patient developing a pressure injury (e.g., a pressure sore or decubitus ulcer), and the risk that the patient may fall. These are referred to herein as a sepsis risk assessment, a pressure injury risk assessment, and a falls risk assessment. This disclosure contemplates that the analytics engine 20 is able to make other risk assessments for the patient based on the data received from sources 12. Such risk assessments are dependent upon the type of sources 12 providing the data and the identification of a relatively close correlation between the data from the multiple sources 12 and a particular patient risk.

Still referring to FIG. 1, the risk assessments are provided to caregivers or clinicians who may adjust or override the risk assessments based on clinical insights 24. The terms "caregiver" and "clinician" are used interchangeably herein. The adjustments to or overriding of the risk assessments based on the clinical insights 24 are implemented using a computer (not shown) such as a personal computer at a work station, a master nurse computer at a master nurse station, a mobile device such as a smart phone or tablet computer carried by a caregiver, and so forth. In some embodiments, each of the risk assessments results in a numerical score within a range of values between, and including, an upper limit and a lower limit. Thus, a caregiver is able to change the risk assessment scores output from the analytics engine 20 if, based on the caregiver's information about the patient and the caregiver's experience, such adjustment is warranted or otherwise desirable.

Based on the risk assessments made by analytics engine 20 and the adjustments made by caregivers due to clinical insights 24, if any, the risk assessments are used to determine clinical services and actions 26 as indicated diagrammatically in FIG. 1. The ultimate goal of the risk assessments made by the analytics engine 20 and the implemented clinical services and actions 26 is to improve patient outcomes as indicated by the breakthrough outcomes block 28 of FIG. 1. For example, if the patient has sepsis or a high risk assessment for sepsis, clinicians may implement one or more of the following services and actions 26 (aka sepsis protocols): providing high-flow oxygen to the patient, drawing blood for laboratory testing such as testing the levels of lactates and hemoglobin, providing intravenous (IV) antibiotics, providing IV fluids, and performing an hourly urine output measurement.

If the patient has a pressure injury or a high risk assessment for a pressure injury, clinicians may implement one or more of the following services and actions 26 (aka pressure injury protocols): a patient support surface therapy such as continuous lateral rotation therapy (CLRT) or alternating pressure therapy, applying a vacuum wound bandage to any pressure ulcer or wound of the patient, capturing an image of the wound(s) for a separate wound assessment, and monitoring the patient movement to assure the patient is repositioning themselves in bed 14 on a suitably frequent basis.

If the patient is a falls risk or has a high risk assessment for falling clinicians may implement one or more of the following services and actions 26 (aka falls protocols): enabling a falls risk protocol on bed 14 which results in the bed circuitry and/or a remote computer (e.g., a bed status computer or nurse call computer) monitoring patient position on the bed 14, monitoring siderail position to confirm that designated siderails are in their raised positions, monitoring caster brake status to confirm that the casters are braked, and monitoring a position of an upper frame of the bed 14 to confirm that it is in a low position relative to a base frame of the bed 14; providing an incontinence detection pad of incontinence detection system 16 between the patient and a mattress of bed 14; providing a walker adjacent to the bed; and providing adequate food and/or water near the patient.

Referring now to FIG. 2, a diagrammatic view shows various activities occurring around the patient bed 14 and also discloses aspects of a digital safety net (DSN) platform 30 based on the activities, the DSN platform including the analytics engine 20. The DSN platform also includes a Power over Ethernet (PoE) switch, router or gateway 32 (these terms are used interchangeably herein) that receives data from a multitude of sources 12, including bed 14, and routes risk assessment information to a plurality of output devices 34 which include graphical displays 36 and an indicator 38 (aka a dome light) of a nurse call system which provides visual information regarding the risk assessments performed by the analytics engine 20.

Beneath the upper left image of FIG. 2, the bullet points indicate that there is an admitted patient in bed 14 and that an initial assessment of the patient has been conducted. In connection with initial assessment, the patient's medical history is taken, the patient's initial vital signs and weight are captured, a baseline pressure injury risk is assessed, and a photo of a suspected pressure injury is taken with a camera 40, illustratively a WOUNDVUE™ camera 40 available from LBT Innovations Ltd. of Adelaide, Australia, and uploaded to the analytics engine 20 for a wound assessment. An arrow 42 situated between the upper left image and the upper center image of FIG. 2 indicates that the data associated with the bullet points beneath the upper left image are communicated to the analytics engine of the DSN platform 30 of the upper center image.

Beneath the upper center image of FIG. 2, the bullet points indicate that the analytics engine 20 of the DSN platform 30 has engaged a sepsis protocol in connection with assessing the patient's risk of developing sepsis; the patient's sepsis risk has been stratified or normalized into a score range of 1 to 5; the patient's condition is being monitored including monitoring the patient's temperature, the patient's motion, and a surface status of a patient support surface (aka a mattress) of bed 14. According to this disclosure, DSN platform 30 also engages a falls protocol in connection with assessing the patient's falls risk and engages a pressure injury protocol in connection with assessing the patient's pressure injury risk. The falls risk and pressure injury risk are also stratified or normalized by the analytics engine 20 into a score range of 1 to 5 in the illustrative example. In other embodiments, the risk ranges for each of the sepsis, falls, and pressure injury risks is 0 to 5. Thus, each of the sepsis, falls, and pressure injury risks has the same maximum value (e.g., 5 in the illustrative examples) and the same minimum value (0 or 1 in the illustrative examples). In other embodiments, different risk ranges are used such as those having upper limits greater than 5 including 10, 20, 25, 30, etc.

Also beneath the upper center image of FIG. 2 are bullet points indicating that the risk levels or scores determined by the analytics engine 20 of the DSN platform 30 are displayed on the output devices 34 across the DSN platform 30 (i.e., at multiple locations throughout the healthcare facility) and that a rounding protocol is adjusted based on one or more of the determined risk scores for the patient's sepsis, falls, and pressure injury risks. With regard to graphical displays 36, the actual values of the scores are displayed in some embodiments, whereas with regard to the dome light 38, a portion of the dome light is illuminated in a particular manner based on the risk scores. For example, if any of the risk scores are 4 or 5, then a red light may be illuminated on the dome light 38 but if each of the risk scores is only 2 or 3, then a yellow or amber light may be illuminated on the dome light 38. If the risk scores are all at a lower level (e.g., 0 or 1 as the case may be), then the portion of the dome light relating to patient risk remains unlit. This lighting scheme for dome light 38 is given as one illustrative example and other lighting schemes are within the scope of the present disclosure, including having a portion or section of dome light 38 allocated to each risk score such that there are three risk light regions of dome light 38 corresponding to the sepsis, falls, and pressure injury risks, with each risk light region being illuminated red, yellow/amber, or unlit for different risk level scores of the associated risk. Other zones on the dome light indicate, for example, whether a caregiver is in the room, whether a patient in the room has placed a nurse call, or whether an equipment alarm in the room is active, including for semi-private rooms, which of two patients has placed the nurse call or which patient is associated with the equipment that is alarming. Dome lights that have portions that illuminate in colors other than red and yellow/amber, such as white, green, blue, purple, etc., are within the scope of the present disclosure.

With regard to adjusting a rounding protocol, the rounding interval or time between caregiver rounds (i.e., the time between when an assigned caregiver is required to check on the patient) is shortened in some embodiments if one or more of the risk scores is high (e.g., level 4 or 5) or if a risk score increases from one level to the next (e.g., increasing from level 2 to level 3). It is contemplated by this disclosure that the higher a risk score is, the shorter the rounding interval will be. The correlation between rounding interval times and risk score levels, including summing two or three of the risk scores together for determining a rounding interval, is at the discretion of the system programmer or administrator. An arrow 44 situated between the upper center image and the upper right image of FIG. 2 indicates that after the activities associated with the bullet points beneath the upper center image are performed by the DSN platform 30, the bed 14 and vital signs equipment 18 (and other equipment as disclosed herein) continue to provide data to the analytics engine 20 for dynamic, real-time risk assessment.

In some embodiments, adjustment of the rounding interval occurs dynamically, automatically, and substantially in real time as the risk scores increase and decrease. Thus, a rounding interval is decreased automatically from four hours to two hours if a risk score increases from, for example, a level 3 to level 4, and the rounding interval is increased from two hours to four hours, for example, if a risk score decreases from a level 4 to a level 3, just to give one arbitrary example to illustrate the concept. The rounding intervals are tracked and changed by an EMR computer or server or a nurse call computer or server in some embodiments. The rounding interval adjustments are made without human input or involvement at the computer or server that controls the rounding intervals in some embodiments. In other embodiments, a caregiver or clinician or other administrator at the rounding computer provides inputs to approve the rounding interval change. In either case, a rounding interval change notification is transmitted to the mobile device or devices of the affected caregiver(s) in some embodiments.

The phrase "substantially in real time" as used herein means the amount of time that data measurements or values which contribute to the risk scores are received and are processed for re-calculation of the risk scores. Some equipment 12 may provide readings only once every minute or once every second and other equipment may provide readings 100 time per second, just to give some arbitrary examples. The present disclosure contemplates that the analytics engine 20 re-calculates risk scores each time a new data point is received and such is considered to be "substantially in real time" according to the present disclosure. The present disclosure also contemplates that the analytics engine 20 re-calculates risk scores only if a received measurement or value changes from a previous measurement or value. Thus, if a constant value is transmitted over and over again, the analytics engine does not re-calculate the risk score until one of the contributing measurements or values changes and this is also considered to be "substantially in real time" according to the present disclosure.

Beneath the upper right image of FIG. 2, the bullet points indicate that the dynamic patient risk assessment by the analytics engine 20 includes monitoring, on an ongoing basis, whether patient support surface status is consistent with reduced pressure injury risk or whether the patient support surface status has changed in such a manner as to create an increased pressure injury risk. For example, if a bladder of the mattress of bed 14 has a leak and a sufficient amount of air is lost, the bladder pressure may decrease enough to permit a patient to bottom out through the mattress so as to be supported on the underlying mattress support deck rather than being supported by the bladder. Such a situation increases the risk that the patient may develop a pressure injury. According to this disclosure, the dynamic risk assessment by the analytics engine 20 also includes monitoring whether the patient's vital signs sensed by monitors 18 or by the on-bed vital sign sensors, are consistent and within desirable limits or whether the vital signs are changing in a manner indicative of declining health of the patient. If the latter scenario is detected, the patient's sepsis risk score is increased. Further according to this disclosure, the dynamic risk assessment by the analytics engine 20 also includes determining whether the patient is sleeping or not in the room, in which case the patient's falls risk score is decreased, or whether the patient is moving, agitated, or in pain, in which case the patient's falls risk score is increased. As the patient's risks scores increase or decrease, the clinical protocols for the patient are adjusted in a commensurate manner to match the changing risk level.

An arrow 46 situated between the upper right image and the lower right image of FIG. 2 indicates that after a period of time, other conditions of the patient on bed 14 may be detected. As indicated by the bullet points beneath the lower right image of FIG. 2, if a patient change is detected by bed 14, such as lack of patient motion or patient motion below a threshold, for a prolonged period of time, and/or if a problematic surface change is detected, then a pressure injury algorithm executed by the analytics engine 20 determines that there is an increased risk of a pressure injury and the patient's pressure injury score is increased. Furthermore, in response to the increased pressure injury score, the analytics engine 20 initiates one or more alerts to one or more caregivers of the increased pressure injury risk and, in some embodiments, automatically activates a pressure injury prevention protocol such as reducing the rounding time automatically and/or implementing a surface therapy protocol such as sending reminder messages to a caregiver to turn the patient, to activate a turn assist function of bed 14 at regular intervals (e.g., every hour or every two hours), to activate an alternating pressure therapy of the mattress of bed 14, or to activate a CLRT therapy of the mattress of bed 14.

If the analytics engine 20 receives data from bed 14 or vital signs monitors 18 resulting in an increased falls risk score or sepsis risk score, then the DSN platform 30 responds in a similar manner to alert caregivers of the increased score. For example, an increased patient heart rate coupled with increased patient movement may indicate that the patient is preparing to exit the bed 14 and the falls risk score may be increased accordingly. As another example, if the patient's heart rate or respiration increases but there is a lack of patient motion or patient movement below a threshold, thereby indicating a lethargic patient, then this may indicate an increased sepsis risk and the sepsis risk score may be increased accordingly.

In each of these cases of increasing risk score, the analytics engine 20 initiates an alert to one or more caregivers assigned to the patient in some embodiments. Such alerts may be sent to a mobile device (e.g., pager, personal digital assistant (PDA), smart phone, or tablet computer) carried by the respective one or more caregivers. Such alerts may also be displayed on graphical displays 36 and dome lights 38 of system 10. As was the case for the increasing pressure injury score, a falls risk protocol or a sepsis protocol may be initiated automatically by the analytics engine 20 in response to an increasing falls risk score or increasing sepsis risk score, respectively.

According to this disclosure, analytics engine 20 also provides risk score data or messages to sources 12, such as beds 14 and monitors 18 that are equipped with communications circuitry configured for bidirectional communication with analytics engine 20. Thus, in some embodiments, a message received by one or more of sources 12 from analytics engine 20 results in a risk reduction protocol or function of the source 12 being activated automatically (e.g., an alternating pressure function of a mattress being turned on automatically or an infusion pump for delivery of IV antibiotics being turned on automatically or a bed exit/patient position monitoring function of a bed being turned on automatically). In some embodiments, graphical displays of the sources 12, such as beds 14 and monitors 18, receiving such messages from analytics engine 20 display a message indicating that one or more of the pressure injury, falls, and sepsis risk scores have increased and, in appropriate circumstances, that a risk reduction protocol or function of the source 12 has been turned on or activated automatically.

An arrow 48 situated between the lower right image and the lower left image of FIG. 2 indicates that a caregiver has been dispatched to the patient room of the patient whose risk score has increased. Thus, as indicated by the bullet points beneath the lower left image of FIG. 2, in response to an increasing pressure injury score, falls risk score, or sepsis risk score, the analytics engine 20 initiates an alert or notification to one or more assigned caregivers to immediately go to the patient's room and engage the patient. When the caregiver reaches the patient room, some of the risk factors resulting in the increased risk score may be addressed at that time. For example, the caregiver may assist a patient in going to the bathroom in response to an increase falls risk score or the caregiver may turn on a mattress turn assist function or therapy function for a patient having an increased pressure injury risk score or the caregiver may initiate delivery of IV antibiotics for a patient having an increased sepsis risk score.

After the caregiver addresses the patients falls risk, pressure injury, and/or sepsis needs, the data provided to analytics engine 20, in some cases, will result in the respective risk score being decreased automatically. In some cases, however, the caregiver provides clinical insights 24 to the analytics engine 20 that result in a decreased risk score after the caregiver has addresses the patient's needs. In the case of an increased pressure injury score, the caregiver dispatched to the patient's room may be required, in some embodiments, to take a picture of any of the patient's pressure injuries using camera 40 for upload to analytics engine 20 so that the most recent pressure injury data is used in connection with determining the patient's pressure injury score.

Figure 3:
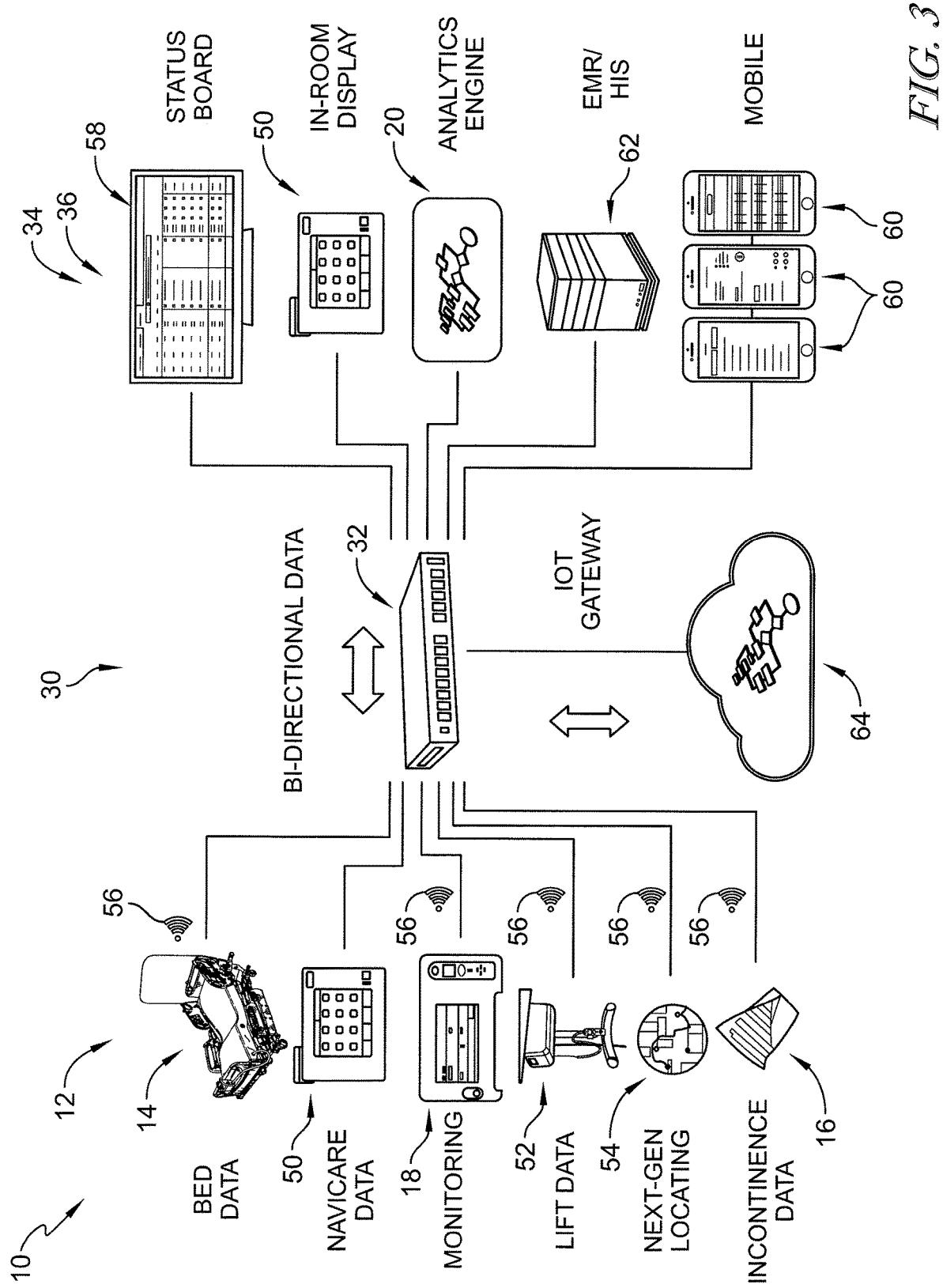
FIG. 3 is a diagrammatic view of a system, similar to FIGS. 1 and 2, showing a router located in a center of the view receiving data from a plurality of data source equipment situated to the left of the router and communicating to a plurality of data receiving equipment to the right of the router, the data source equipment including a patient bed, a graphical room station of a nurse call system, a vital signs monitor, a patient lift, a locating system, and an incontinence detection system, and the data receiving equipment including a status board, an in-room display, an analytics engine, an electronic medical records (EMR) or health information systems (HIS) server, and a set of mobile devices.

Referring now to FIG. 3, additional sources 12 of system 10 that provide data to analytics engine 20 via router or PoE switch 32 are shown. The additional sources 12 of FIG. 3 include a graphical room stations 50, patient lifts 52, and a locating system 54. Graphical room station 50 is included as part of a nurse call system such as the NAVICARE® Nurse Call system available from Hill-Rom Company, Inc. of Batesville, Ind. Additional details of suitable nurse call systems in which room stations 50 are included can be found in U.S. Pat. Nos. 7,746,218; 7,538,659; 7,319,386; 7,242,308; 6,897,780; 6,362,725; 6,147,592; 5,838,223; 5,699,038 and 5,561,412 and in U.S. Patent Application Publication Nos. 2009/0217080 A1; 2009/0214009 A1; 2009/0212956 A1; and 2009/0212925 A1, each of which is hereby incorporated by reference herein in its entirety for all that it teaches to the extent not inconsistent with the present disclosure which shall control as to any inconsistencies. Room stations 50 are among the sources 12 that caregivers use to provide clinical insights 24 into system 10 for analysis by analytics engine 20.

Patient lifts 52 provide data to analytics engine 20 via router 32 in response to being used to lift a patient out of bed 14 for transfer to a stretcher, chair, or wheelchair, for example. The fact that a patient lift 52 needs to be used to move a patient to or from bed 14 is indicative that the patient is a falls risk because the patient is not able to exit from bed 14 and walk on their own or to get back onto bed 14 on their own. Thus, the falls risk score is increased by the analytics engine 20 in response to the patient lift 52 being used to move the patient. Furthermore, use of the patient lift 52 to move a patient to or from bed 14 also may be indicative that the patient is at higher risk of developing a pressure injury than an ambulatory patient. For example, lifts 52 are oftentimes used to transfer paraplegic or quadriplegic patients and such patients, while in bed, have limited ability to shift their weight to reduce the chances of developing pressure injuries. Also, slings used with patient lifts sometimes produce high interface pressures on portions of the patient, such as the patient's hips or sacral region, which also may increase the risk of developing a pressure injury. Thus, in some embodiments, use of lift 52 not only results in an increase in the patient's falls risk score but also an increase in the patient's pressure injury score.

The illustrative image of patient lift 52 in FIG. 3 is an overhead lift 52 that is attached to a framework installed in the patient room. Other types of patient lifts 52 include mobile patient lifts which are wheeled into a patient room for use. A set of wireless communication icons 56 are included in FIG. 3 to indicate that some of sources 12 of network 10 communicate wirelessly with the gateway 32, such as via one or more wireless access points (not shown) for example. In particular, icons 56 of FIG. 3 indicate that beds 14, monitors 18, patient lifts 52, components of locating system 56, and components of incontinence detection system 16 communicate wirelessly with gateway 32. The lines extending from sources 12 to gateway 32 in FIG. 3 indicate that the sources may communicate via wired connections with gateway 32 in addition to, or in lieu of, the wireless communication.

In some embodiments, the sources 12 that are able to communicate wirelessly have dedicated circuitry for this purpose. Alternatively or additionally, locating tags of locating system 54 are attached to sources 12, such as beds 14, monitors 18, patient lifts 52, and components of incontinence detection system 16. Locating tags of system 54 are also attached to caregivers and/or patients in some embodiments. The locating tags include transmitters to transmit wireless signals to receivers or transceivers installed at various fixed locations throughout a healthcare facility. In some embodiments, the tags have receivers or transceivers that receive wireless signals from the fixed transceivers. For example, to conserver battery power, the locating tags may transmit information, including tag identification (ID) data, only in response to having received a wireless signal from one of the fixed transceivers. The fixed receivers or transceivers communicate a location ID (or a fixed receiver/transceiver ID that correlates to a location of a healthcare facility) to a locating server that is remote from the various fixed transceivers. Based on the tag ID and location ID received by the locating server, the locations of the various tagged equipment of sources 12, the tag wearing caregivers, and the tag wearing patients is determined by the locating server.

With the foregoing discussion in mind, if a mobile patient lift 52 is determined by the locating system 54 to be in the room of a patient, analytics engine increases the pressure injury risk score and/or the falls risk score for the patient in some embodiments. A similar increase in the sepsis risk score may be made by the analytics engine 20 if certain equipment is determined by locating system 54 to be in the patient room. For example, if a heart rate monitor, respiration rate monitor, and blood pressure monitor are all locating in the patient room for a threshold period of time, then the sepsis risk score is increased by the analytics engine 20 in some embodiments. If a bag or bottle of IV antibiotics in the patient room has a locating tag attached, then the sepsis risk score is increased by the analytics engine 20 in some embodiments.

If an incontinence detection pad of incontinence detection system 16 is determined to be in the patient room, either due to detection of a locating tag attached to the pad by locating system 54 or due to detection of the incontinence detection pad by the circuitry of bed 14 or due to a reader of incontinence detection system 16 providing data to analytics engine 20, possibly via the nurse call system in some embodiments, then the patient's falls risk score and/or the patient's pressure injury score is increased by the analytics engine in some embodiments. Use of an incontinence detection pad with the patient is indicative that the patient is not sufficiently ambulatory to get out of bed 14 and go to the bathroom on their own, and therefore, the patient is a falls risk patient. Furthermore, use of an incontinence detection pad with the patient is indicative that the patient may be confined to their bed 14 which increases the risk of developing a pressure injury. In some embodiments, in response to incontinence detection system 16 detecting that the patient has soiled the incontinence detection pad and that the pad has remained beneath the patient for a threshold amount of time thereafter before being replaced with an unsoiled pad, then the pressure injury risk score is increased by the analytics engine because prolonged exposure to moisture or wetness increases the chance that the patient will develop a pressure injury.

In some embodiments, locating system 54 operates as a high-accuracy locating system 54 which is able to determine the location of each locating tag in communication with at least three fixed transceivers within one foot (30.48 cm) or less of the tag's actual location. One example of a high-accuracy locating system 54 contemplated by this disclosure is an ultra-wideband (UWB) locating system. UWB locating systems operate within the 3.1 gigahertz (GHz) to 10.6 GHz frequency range. Suitable fixed transceivers in this regard include WISER Mesh Antenna Nodes and suitable locating tags in this regard include Mini tracker tags, all of which are available from Wiser Systems, Inc. of Raleigh, N.C. and marketed as the WISER LOCATOR™ system. UWB locating systems available from other manufacturers may be used just as well. In some embodiments, the high-accuracy locating system 54 uses 2-way ranging, clock synchronization, and time difference of arrival (TDoA) techniques to determine the locations of the locating tags. See, for example, International Publication No. WO 2017/083353 A1, which is hereby incorporated by reference herein in its entirety for all that it teaches to the extent not inconsistent with the present disclosure which shall control as to any inconsistencies, for a detailed discussion of the use of these techniques in a UWB locating system.

In those embodiments in which locating system 54 is a high-accuracy locating system 54, a more granular set of rules for determining whether to increment or decrement a particular risk score may be implemented by analytics engine 20. For example, rather than increasing the falls risk score and/or pressure injury score in response to detection of a patient lift 52 in the room or detection of an incontinence detection pad in the room, the particular risk score is only incremented if the relative position between the lift 52 or incontinence detection pad and the patient bed 14 meets certain criteria. For example, the falls risk and/or pressure injury risk score is not incremented until a motorized lift housing and/or sling bar of the overhead lift 52 are determined to be located over a footprint of the hospital bed 14. This prevents the risk score(s) from being increased or incremented if the overhead lift 52 is not in use with the particular patient but is simply stored off to the side of the bed 14 or in a corner of the room. In a similar way, the falls risk and/or pressure injury risk score is not incremented until a mobile lift 52 is determined to be within a threshold distance, such as 1 or 2 feet of the bed 14 or patient just to give a couple arbitrary examples. Further similarly, the falls risk and/or pressure injury risk score is not incremented until the incontinence detection pad is determined to be within a footprint of the hospital bed 14.

Still referring to FIG. 3, the graphical displays 36 of output devices 34 include status boards 58, graphical audio stations 50, and mobile devices 60 of caregivers. The illustrative mobile devices 60 of FIG. 3 are smart phones, but as indicated above, mobile devices 60 also include pagers, PDA's, tablet computers, and the like. Status boards 58 are oftentimes located at master nurse stations in healthcare facilities but these can be located elsewhere if desired, such as in staff breakrooms, hallways, and so forth. In some embodiments, the status boards 58 are included as part of the nurse call system. In this regard, see, for example, U.S. Pat. No. 8,779,924 which is hereby incorporated by reference herein in its entirety to the extent not inconsistent with the present disclosure which shall control as to any inconsistences. This disclosure contemplates that the status board has additional fields for displaying the falls risk, pressure injury risk, and sepsis risk scores for each of the listed patients on the status board.

As is apparent in FIG. 3, graphical room stations 50 serve as both sources 12 for providing data to the analytics engine 20 and as output devices 34 for displaying data from the analytics engine 20. Thus, graphical room stations 50 also have display screens with fields for displaying the falls risk, pressure injury risk, and sepsis risk scores for the patients located in the rooms having the room stations 50. In some embodiments, stations 50 are operable to obtain and display the risk scores of patients located in other rooms. Thus, a caregiver using the room station 50 in one room may be communicating with another caregiver, such as a nurse at a master nurse station, about a patient located in another room and can pull up information, including the risk scores, pertaining to the other patient being discussed.

Mobile devices 60 also have screens with fields to display the risk scores of patients. In some embodiments, a mobile software application is provided on the mobile devices 60 of caregivers and operates to limit the caregiver's ability access to information, such as only being able to see the risk scores for their assigned patients and not those of patients assigned other caregivers. Furthermore, it is contemplated by this disclosure that a pop-up window may appear on the caregiver's mobile device each time a risk score changes for any of the caregiver's assigned patients. Examples of screens that appear on mobile devices 60 in some embodiments are discussed below in connection with FIGS. 7-10.

An electronic medical records (EMR) or health information systems (HIS) server 62 is also communicatively coupled to the analytics engine 20 via PoE switch 32 as shown in the illustrative example of FIG. 3. Server 62 is coupled to one or more EMR or HIS computers (not shown) that have display screens for showing the risk scores of the various patients of the healthcare facility. In some embodiments, server 62 is also a source 12 of data for analytics engine 20 to use in connection with determining the risk scores of the various patients. Analytics engine 20 is also communicatively coupled to an Internet of Things (IoT) network or platform 64 via gateway 32 as shown in FIG. 3. Platform 64 receives information from multiple healthcare facilities and operates to analyze the incoming information to identify best practices for risk reduction protocols that, in turn, may be shared with other healthcare facilities that may subscribe to receive such best practice information. The best practice information may include relevant thresholds to use in risk assessment algorithms, steps to implement in a standard of care to keep patient risks to a minimum, and corrective actions to take in response to elevated patient risk scores, for example. Platform 64 also may implement analytics for predicting patient outcomes and communicate the predictions to subscribing healthcare facilities, for example.

As indicated in FIG. 3, analytics engine 20 communicates bidirectionally with some or all of sources 12, output devices 34, server 62, and platform 64. Analytics engine 20 comprises one or more servers or other computers that implement analytics software that is configured in accordance with the various algorithms and rules discussed above. It should be appreciated that FIGS. 1-3 are diagrammatic in nature and that other network infrastructure communicatively interconnects each of the devices of system 10 discussed above in each healthcare facility in which system or apparatus 10 is implemented. Another diagrammatic example of network infrastructure is discussed below in connection with FIG. 6.

Figure 4A:
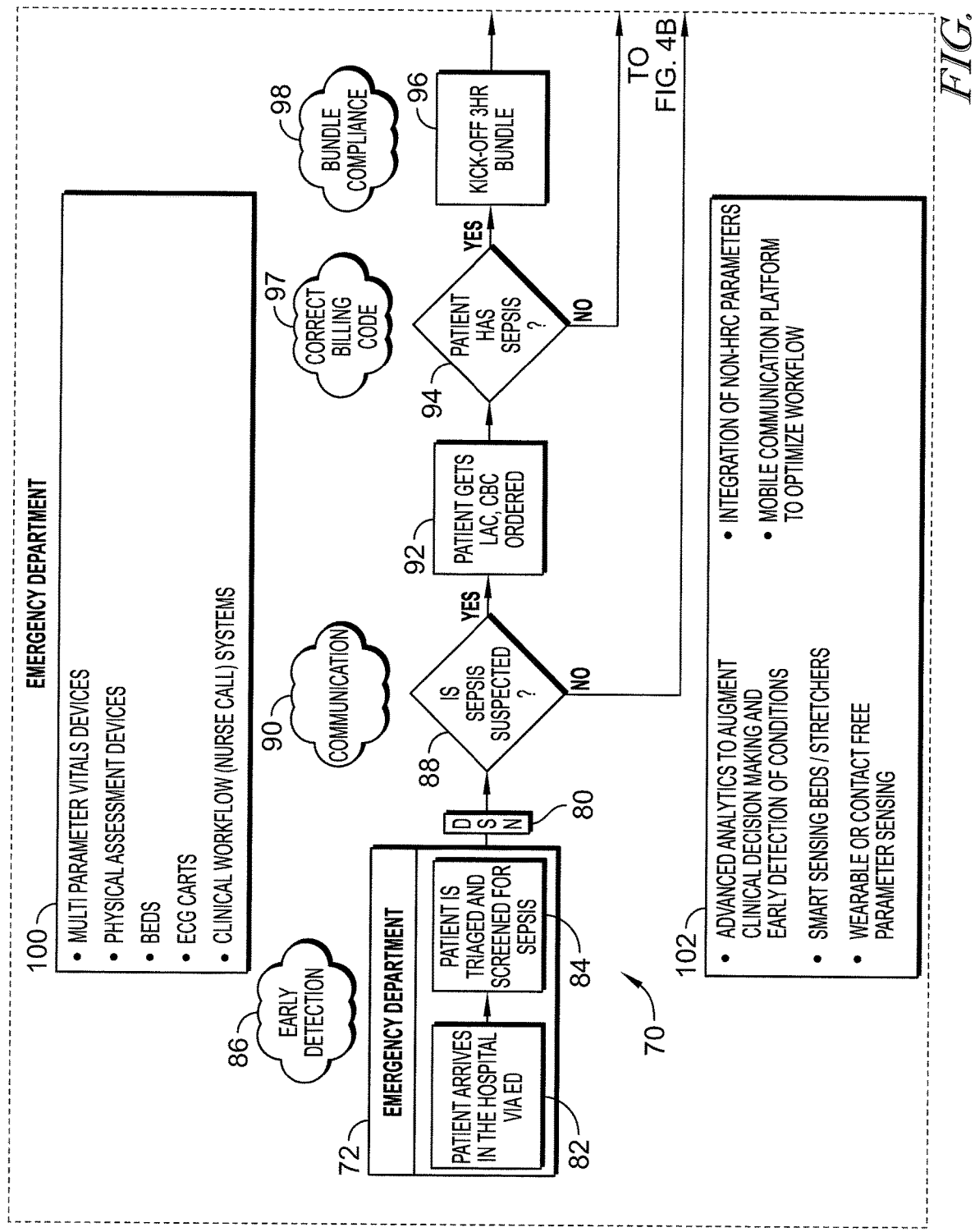
FIGS. 4A-4C form a flow chart showing an example of a patient's journey through an emergency department (ED), an intensive care unit (ICU) and a medical/surgical (MED/SURG) unit, and then home or to a long term care (LTC) facility and showing locations within the patient flow at which the analytics engine operates to determine the patient's risk of having or developing sepsis.
Figure 4B:
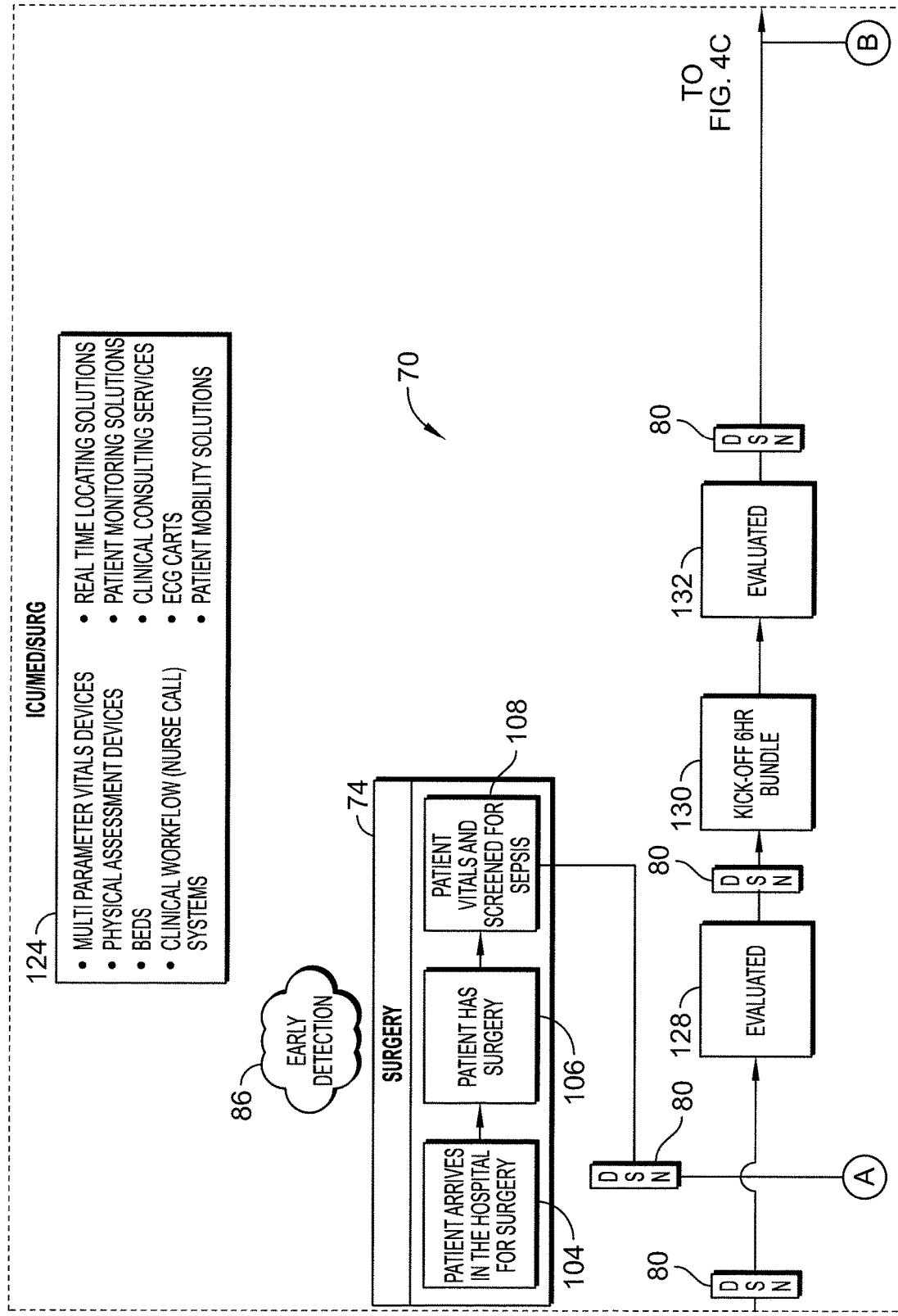
Figure 4B:
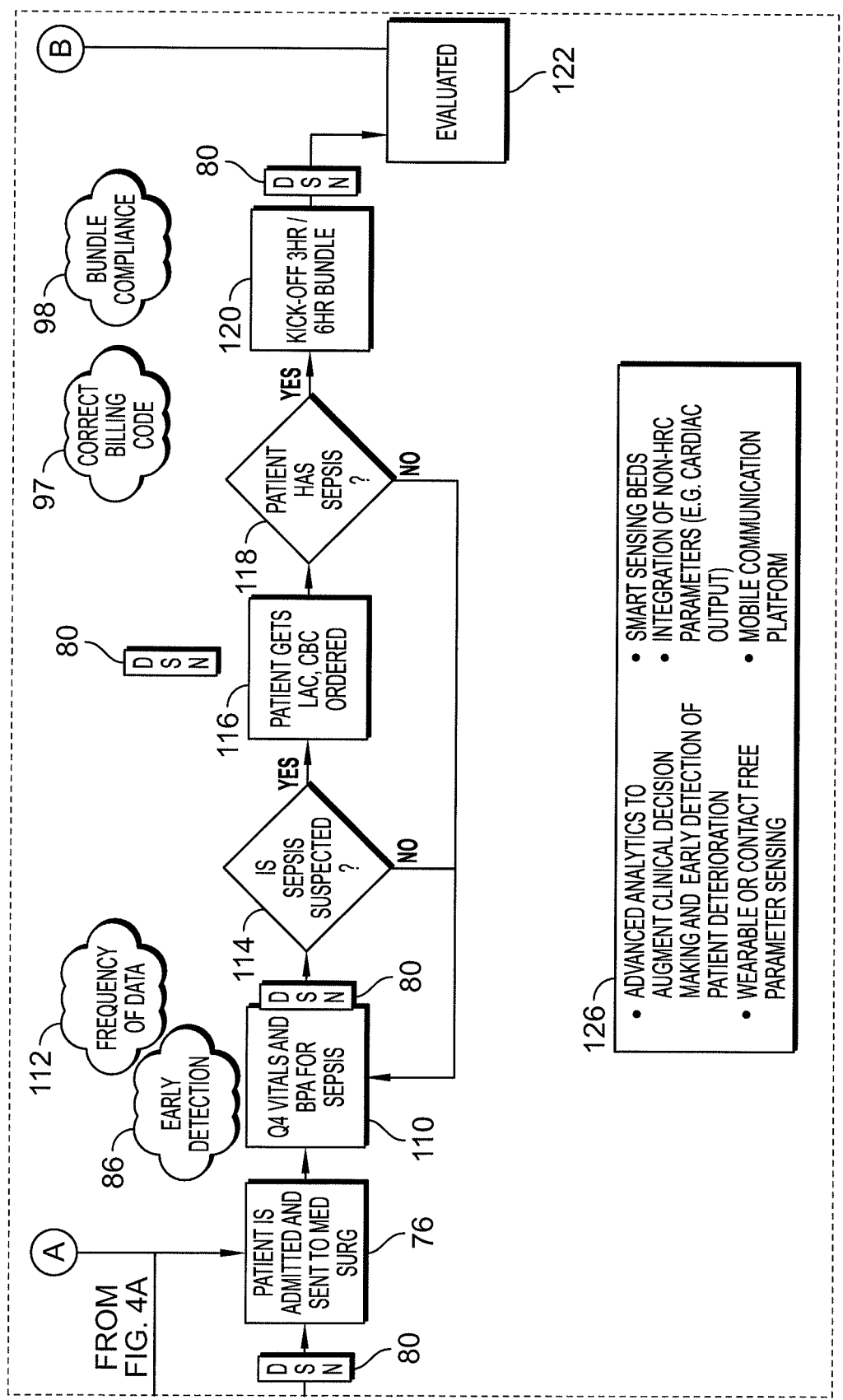
Figure 4C:
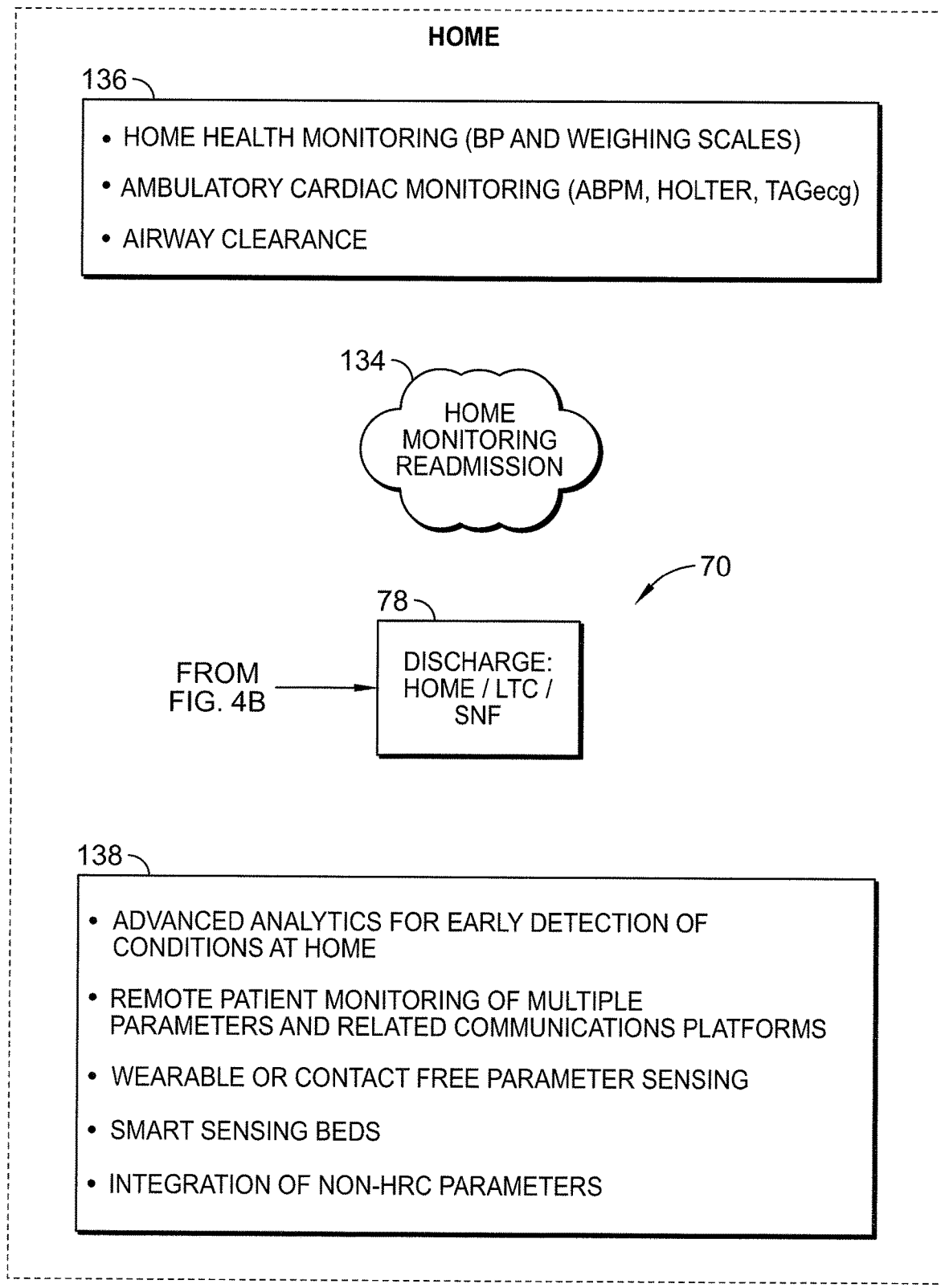

Referring now to FIGS. 4A-4C, a flow chart 70 shows an example of a patient's journey beginning at an emergency department (ED) indicated by block 72 or Surgical unit indicated by block 74, then moving on to an intensive care unit (ICU) or a medical/surgical (MED/SURG) unit indicated by block 76, and then home or to a long term care (LTC) facility or a skilled nursing facility (SNF) as indicated by block 78. Flow chart 70 shows locations within the patient flow at which the analytics engine 20 of DSN platform 30 operates to determine the patient's risk of having or developing sepsis. Wherever in flow chart 70 the DSN platform 30 is invoked for patient risk assessment of sepsis, a DSN platform block 80 is shown.

Referring now to FIG. 4A, a patient arrives in a hospital at the ED 72 as indicated at block 82 and is triaged and screened for sepsis as indicated at block 84. This initial screening is for the purpose of early detection of sepsis as indicated by Early Detection cloud 86 above ED 72. The information from the screening at block 84 is provided to DSN platform 30 as indicated by the associated block 80 and then a determination is made as to whether it is suspected that the patient has sepsis as indicated at block 88. The determination at block 88 is made by analytics engine 20 based on information communicated from DSN 30 as indicated by Communication cloud 90 above block 88.

If it is determined at block 88 that sepsis is suspected, then the patient gets Lactic Acid Culture (LAC) and Complete Blood Count (CBC) tests ordered as indicated at block 92. Lactic acid (aka lactate) in the blood greater than 2 millimoles per liter (mmol/L) is one of the indicators that the patient has sepsis. According to some sepsis determination protocols, this level of lactate in the blood is considered in combination with other sepsis risk factors including one or more of the following: i) systolic blood pressure being less than 90 millimeters of Mercury (mmHg) or a mean arterial blood pressure being less than 65 mmHg; ii) heart rate being greater than 130 beats per minute, iii) respiratory rate being greater than 25 breaths per minute, iv) oxygen saturation (e.g., SpO2) being less than 91%, v) the patient being unresponsive or responds only to voice or pain, and/or vi) the presence of a purpuric rash. According to other sepsis determination protocols, sepsis is determined to be likely if the following criteria are met: i) the patient's temperature is greater than about 38.3° Celsius (C) (about 101° Fahrenheit (F)) or less than about 35.6° C. (about 96° F.), ii) the patient's heart rate is greater than 90 beats per minute; and iii) the patient's respiration rate is greater than 20 respirations per minute. Thus, different healthcare facility have different sepsis determination protocols and all such protocols are within the scope of the present disclosure.

After the blood test of block 92, a determination is made as to whether or not the patient has sepsis as indicated at block 94. If the patient has sepsis, as determined at block 94, then a 3 hour (Hr) bundle is kicked-off as indicated at block 96. A 3 Hr bundle includes, for example, administration of broad spectrum antibiotics and administering 30 milliliters per kilogram (mL/kg) of Crystalloid for Hypotension or Lactate greater than or equal to 4 mmol/L. The 3 Hr bundle also may include measuring Lactate level and obtaining blood cultures at some healthcare facilities, but in FIG. 4A, these were done at block 92 prior to kicking off the 3 Hr bundle at block 96. Above block 96 are a Correct Billing Code cloud 97 and a Bundle Compliance Cloud 98 which, in some embodiments, may invoke monitoring and feedback to caregivers by the DSN platform 30 or the HIS server 62.

A box 100 at the top of FIG. 4A includes bullet points indicative of equipment and systems used in connection with the portion of flow chart 70 shown in FIG. 4A. In particular, box 100 lists multi-parameter vitals devices, physical assessment devices, beds, ECG carts, and clinical workflow (nurse call) systems. These systems and equipment are sources 12 to analytics engine 20 of DSN platform 30 in some embodiments. A box 102 at the bottom of FIG. 4A includes bullet points indicative of aspects of the DSN platform 30 used in connection with the portion of flow chart 70 shown in FIG. 4A. In particular, box 102 lists advanced analytics to augment clinical decision making and early detection of conditions (e.g., analytics engine 20), smart sensing beds or stretchers (e.g., beds 14 having vital signs sensors or integrated incontinence detection system 16), wearable or contact free parameter sensing (e.g., some embodiments of monitors 18), integration of parameters from sources of multiple companies (e.g., vitals monitors 18 of various companies), and mobile communication platform to optimize workflow (e.g., caregiver mobile devices 60).

If at block 88 of FIG. 4A sepsis is not suspected, or if at block 94 of FIG. 4A it is determined that the patient does not have sepsis, then the patient is admitted to the healthcare facility and is sent to a Med/Surg unit as indicated at block 76 of FIG. 4B (Cont.). The information regarding a negative sepsis suspicion or determination at blocks 88, 94 may be communicated to the analytics engine 20 of DSN platform 30 in connection with the patient being sent to the Med/Surg unit in some embodiments. Thus, two out of the three flow paths exiting from the right hand side of FIG. 4A, lead to the patient being admitted and sent to the Med/Surg unit as indicated at block 76 of FIG. 4B (Cont.). As shown in FIG. 4B, instead of arriving at the emergency department, it is contemplated that a patient arrives at the Surgical unit 74 of the hospital for surgery as indicated at block 104 within surgical unit 74. Thereafter, the patient has surgery as indicated at block 106. During or after surgery, the patient's vitals (i.e., vital signs) are measured and the patient is screened for sepsis while in the Surgical unit 74 as indicated at block 108 of FIG. 4B. In this regard, Early detection cloud 86 is also shown in FIG. 4B above the Surgical unit 74.

After surgery, the patient's vitals information and sepsis screening information from block 108 is provided to the analytics engine 20 of the DSN platform 80 and then the patient is admitted to the healthcare facility and is sent to the Med/Surg unit as indicated at block 76 of FIG. 4B (Cont.). After the patient is admitted to the Med/Surg unit at block 76, Q4 vitals and Best Practice Alerts (BPA) for sepsis are implemented as indicated at block 110 and the associated data is provided to the analytics engine 20 of the DSN platform as indicated by block 80 adjacent to block 110. Q4 vitals are vitals that are taken 4 hours apart, such as 8 am, noon, 4 pm, 8 pm, midnight, 4 am, etc. Early Detection cloud 86 is shown above block 110 in FIG. 4B as is a Frequency of Data cloud 112. Thus, cloud 112 above block 110, indicates that caregivers may change the frequency of taking the patient's vital signs to Q1, Q2, or Q8 (i.e., one, two or eight hours apart, respectively, instead of four hours apart) based on clinical insights 24.

Based on the data obtained in connection with block 110, a determination is made as to whether it is suspected that the patient has sepsis as indicated at block 114. If it is determined at block 114 that sepsis is not suspected, the work flow 70 returns back to block 110 and proceeds from block 110. If it is determined at block 114 that sepsis is suspected, then the patient gets LAC and CBC tests ordered as indicated at block 116. The LAC and CBC tests were discussed above in connection block 92 of FIG. 4A and the same discussion is applicable to block 116 of FIG. 4B (Cont.). The results of the LAC and CBC are communicated to the analytics engine 20 of the DSN platform 30 as indicated by the block 80 that is situated above block 116 in FIG. 4B (Cont.).

Based on the results of the LAC and CBS tests at block 116, a determination is made as to whether the patient has sepsis as indicated at block 118. If at block 118 it is determined that the patient does not have sepsis, the workflow 70 returns back to block 110 and proceeds from block 110. If the patient has sepsis, as determined at block 118, then a 3 Hr bundle is kicked-off as indicated at block 120. The 3 Hr bundle was discussed above in connection with block 96 of FIG. 4A and the same description is applicable to block 120 of FIG. 4B (Cont.). Above block 120 are Correct Billing Code cloud 97 and Bundle Compliance cloud 98 which, in some embodiments, may invoke monitoring and feedback to caregivers by the DSN platform 30, as indicated by block 80 to the right of block 120, or by the HIS server 62. After the 3 Hr bundle is kicked-off at block 120 of FIG. 4B, the patient is evaluated as indicated at block 122 of FIG. 4B (Cont.).

A box 124 at the top of FIG. 4B includes bullet points indicative of equipment and systems used in connection with the portion of flow chart 70 shown in FIGS. 4B and 4B (Cont.). In particular, box 124 lists multi-parameter vitals devices, physical assessment devices, beds, clinical workflow (nurse call) systems, real time locating solutions (RTLS's), patient monitoring solutions, clinical consulting services, ECG carts, and patient mobility solutions. These systems (or solutions) and equipment of block 124 are sources 12 to analytics engine 20 of DSN platform 30 in some embodiments. A box 126 at the bottom of FIG. 4B (Cont.) includes bullet points indicative of aspects of the DSN platform 30 used in connection with the portion of flow chart 70 shown in FIGS. 4B and 4B (Cont.). In particular, box 126 lists advanced analytics to augment clinical decision making and early detection of patient deterioration (e.g., analytics engine 20), wearable or contact free parameter sensing (e.g., some embodiments of monitors 18), smart sensing beds (e.g., beds 14 having vital signs sensors or integrated incontinence detection system 16), integration of parameters from sources of multiple companies (e.g., vitals monitors 18 of various companies that output vital signs, including cardiac output), and mobile communication platforms (e.g., caregiver mobile devices 60).

After the 3 Hr bundle of block 96 of FIG. 4A is kicked off, the patient is evaluated as indicated at block 128 of FIG. 4B and data regarding the 3 Hr bundle is provided to the analytics engine 20 of the DSN platform 30 as indicated by the block 80 in FIG. 4B which is situated to the left of block 128. The data obtained during the evaluation of the patient at block 128 is provided to the analytics engine 20 of the DSN platform as indicated by the block 80 to the right of block 128. In the illustrative example, a 6 Hr bundle is kicked off as indicated at block 130 after the data from the patient evaluation of block 128 has been analyzed by the analytics engine 20 of the DSN platform. The 6 Hr bundle, in some embodiments, includes applying vasopressors to maintain MAP greater than or equal to 65 mmHg, measuring central venous pressure (CVP), measuring central venous oxygen saturation ($S_{CVO2}$), and re-measuring lactate if initial lactate level was elevated. The 6 Hr bundle may vary from healthcare facility to healthcare facility. After the 6 Hr bundle of block 130, the patient is evaluated once more as indicated at block 132 and the data from the evaluation, including information regarding the steps of the 6 Hr bundle of block 130, is provided to the analytics engine 20 of the DSN platform 30 as indicated by the block 80 to the right of block 132 in FIG. 4B.

If the patient evaluation at block 122 or at block 132, as the case may be, indicates that the patient no longer has sepsis, as is the case in the illustrative example of flow chart 70, then the patient is discharged to return home or to an LTC facility or to an SNF as indicated at block 78 of FIG. 4C. A Home Monitoring Readmission cloud 134 is situated above block 78 to indicate that continued monitoring of the patient's condition while at home is contemplated. In this regard, a box 136 at the top of FIG. 4C includes bullet points indicative of equipment and systems used in connection with the portion of flow chart 70 shown in FIG. 4C. In particular, box 136 lists home health monitoring (BP and weighing scales), ambulatory cardiac monitoring (including vitals monitoring equipment 18 such as an ambulatory blood pressure monitor (ABPM), a Holter monitor, and/or a TAGecg device), and an airway clearance device. These at-home devices and equipment of block 136 are also sources 12 to analytics engine 20 of DSN platform 30 in some embodiments. Thus, such at-home sources 12 communicate with analytics engine 20 via the Internet in some embodiments.

A box 138 at the bottom of FIG. 4C includes bullet points indicative of aspects of the DSN platform 30 used in connection with the portion of flow chart 70 shown in FIG. 4C. In particular, box 138 lists advanced analytics for early detection of patient conditions at home (e.g., analytics engine 20), remote patient monitoring of multiple parameters and related communication platforms, wearable or contact free parameter sensing (e.g., some embodiments of monitors 18), smart sensing beds (e.g., beds 14 having vital signs sensors or integrated incontinence detection system 16), and integration of parameters from sources of multiple companies (e.g., vitals monitors 18 of various companies that output vital signs).

Figure 5A:
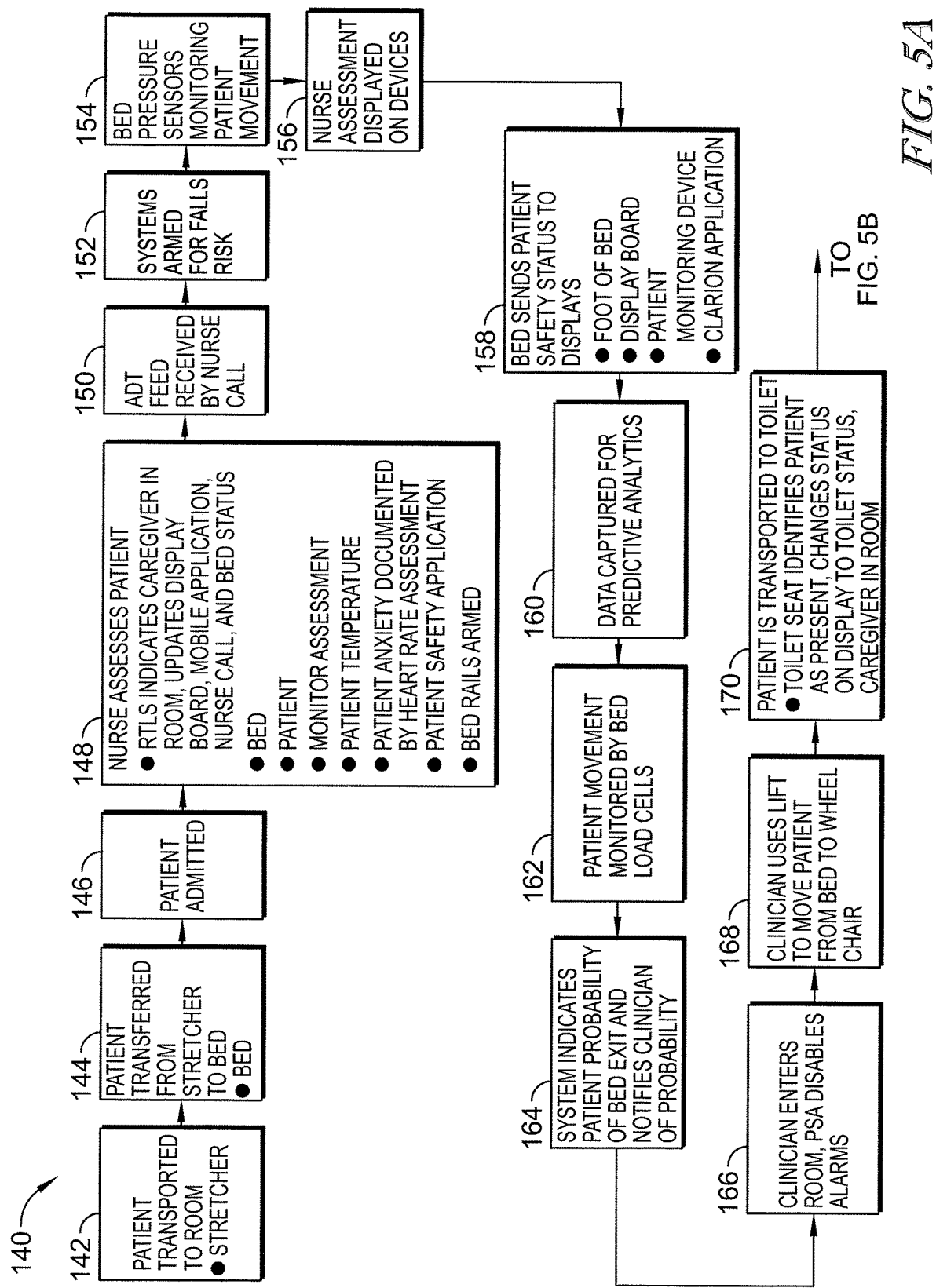
FIGS. 5A and 5B form a flow chart showing an example of a patient's admission and stay at a healthcare facility including use of equipment in the patient's room to move the patient to a chair or into a bathroom, and showing locations within the patient flow at which the analytics engine operates to make a risk assessment for the patient.
Figure 5B:
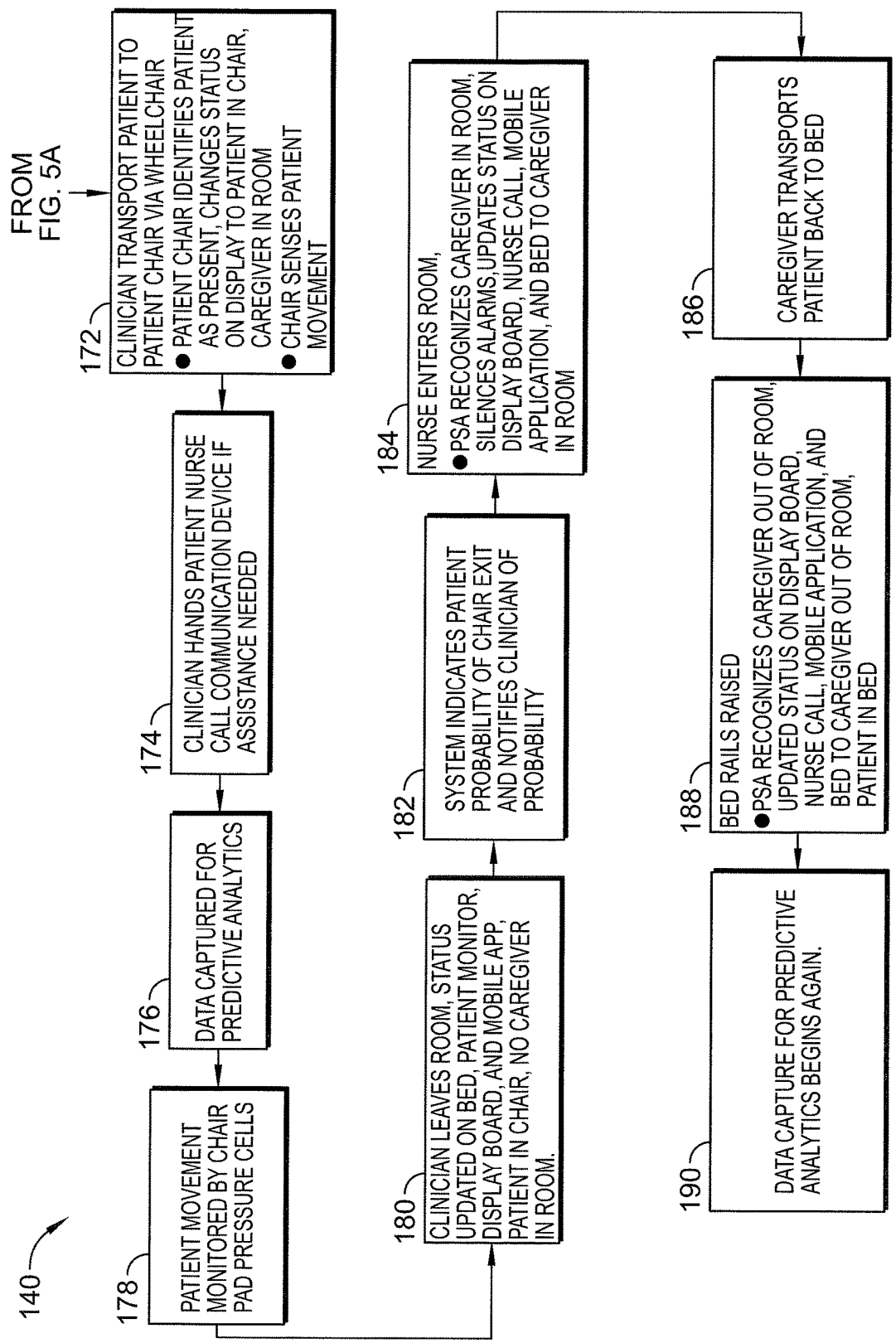

Referring now to FIGS. 5A and 5B, a flow chart 140 is provided showing an example of a patient's admission and stay at a healthcare facility including use of equipment in the patient's room to move the patient and showing locations within the patient flow at which the analytics engine 20 operates to make a risk assessment for the patient. At block 142 of FIG. 5A of flow chart 140, a patient is transported to a patient room on a stretcher. Thereafter, the patient is transferred from the stretcher to the patient bed 14 in the room as indicated at block 144. At this point, the patient is admitted to the healthcare facility as indicated at block 146. In some embodiments, the patient is admitted prior to being transported to the patient room.

Once in the room, a nurse assesses the patient as indicated at block 148 of FIG. 5A. As shown in block 148, if a real time locating system (RTLS) determines that a caregiver is located in the patient room, then information on a display board, displays of mobile devices 60, displays 50 of the nurse call system, and status board 58 are updated to indicate the caregiver's presence in the room. Block 148 also indicates that the nurse assesses the bed condition (e.g., siderails in proper position, caster brakes are set, etc.), assesses the patient, conducts an assessment of monitors 18, checks patient temperature, documents patient anxiety level in connection with a heart rate assessment, activates a Patient Safety Application (PSA) (e.g., enables or arms a bed exit/patient position monitoring (PPM) system), and arms bed rails (e.g., indicates which siderails should be in the raised position in connection with the bed exit/PPM system).

As indicated at block 150 to the right of block 148, a feed from an admission/discharge/transfer (ADT) system is received by the nurse call system of the healthcare facility and, if the ADT feed indicates the patient is a falls risk, the nurse call system sends a message to the bed 14 associated with the patient to arm systems on bed 14 (e.g., arm the bed exit/PPM system and monitor bed siderail position, caster brake status, etc.) as indicated at block 152. In the illustrative example of FIG. 5A, bed pressure sensors are used to monitor patient movement as indicated at block 154 to the right of block 152. Alternatively or additionally, load cells of a weigh scale system of the bed 14 monitors patient movement.

As indicated at block 156 of FIG. 5A beneath block 154, some or all of the information obtained in the nurse assessment of block 148 is displayed on one or more display devices such as output devices 34 discussed above. Furthermore, as indicated in block 158 down and to the left of block 156, bed 14 sends patient safety status information for displays such as a display at a foot end of the bed, a display board (e.g., status board 58), one or more patient monitoring devices 18, and mobile devices 60 (the "Clarion application" listed in block 158 is software used by mobile devices 60 for caregiver-to-caregiver communication and for communication of alerts (aka alarms) and device data). In some embodiments, the "Clarion application" is the LINQ™ mobile application available from Hill-Rom Company, Inc.

The data associated with blocks 148, 150, 152, 154, 156, 158 is also captured for predictive analysis by analytics engine 20 of the DSN platform as indicated by block 160 to the left of block 158. In this regard, the analytics engine 20 receives patient movement data as monitored by load cells of bed 14 as indicated at block 162 to the left of block 160, and then communicates messages indicative of patient probability of bed exit and notifies one or more clinicians of the probability as indicated at block 164. As indicated at block 166 below block 164 in FIG. 5A, if a clinician enters the patient room, the PSA disables any alarms associated with features monitored by the PSA.

In the illustrative example of flow chart 140 of FIG. 5A, the clinician uses a patient lift to move the patient from the bed 14 to a wheelchair as indicated at block 168. Thereafter, as indicated at block 170, the clinician transports the patient to a toilet, such as a toilet in a bathroom included as part of the patient room, for example. Block 170 also indicates that a toilet seat identifies the patient as being present (e.g., sitting on the toilet seat) which results in a change of status on one or more of the displays of output devices 34 to toilet status for the patient and also indicates on the displays that the caregiver is in the room.

After the patient is finished using the bathroom, the clinician transports the patient to a chair in the room using the wheelchair as indicated at block 172 of FIG. 5B. Block 172 also indicates that the chair identifies the patient as being present (e.g., sitting on the chair) which results in a change of status on one or more of the displays of output devices 34 to Patient-in-Chair status for the patient and one or more of these displays also continue to indicate that the caregiver is in the room. Block 172 further indicates that the chair senses patient movement. Thus, this disclosure contemplate that the chair has load cells, pressure sensors, force sensitive resistors (FSR's), or the like, along with associated circuitry, to sense patient position in the chair and to communicate the patient position in the chair to the analytics engine 20. As indicated in block 174 to the left of block 172, in the illustrative example of flow chart 140, the clinician hands the patient a nurse call communication device (e.g., a pillow speaker unit) that the patient can use to place a nurse call if assistance is needed after the caregiver leaves the patient room while the patient is sitting in the chair.

While the patient is sitting in the chair, the analytics engine 20 of the DSN platform 30 captures data from the chair for predicative analysis of chair exit as indicated at block 176 to the left of block 174 in FIG. 5B. In the given example, patient movement is monitored by chair pad pressure cells as indicated at block 178 to the left of block 176. As indicated by block 180 below blocks 176, 178 in the illustrative flow chart 140, the clinician leaves the room, the caregiver's status of no longer being present in the room is updated on the displays of bed 14, monitors 18, display boards 50, 58 of output devices 34, and the displays of mobile devices 60 but the patient's status as Patient-in-Chair remains on these displays.

As indicated in block 182 which is situated to the right of block 180 and beneath block 174 in FIG. 5B, system 10 indicates patient probability of chair exit by the patient and notifies one or more clinicians of the probability. Thereafter, a nurse enters the room as indicated at block 184. In response to the caregiver entering the room, the PSA receives information from the locating system that the caregiver is in the room, silences alarms on the bed 14, and sends a message resulting in one or more of displays of bed 14, monitors 18, display boards 50, 58 of output devices 34, and the displays of mobile devices 60 being updated to indicate that the caregiver is in the room.

In the illustrative example of flow chart 140, after the caregiver enters the room at block 184, the caregiver transports the patient back to bed 14 as indicated at block 186. Thereafter, the bed siderails are raised as indicated at block 188 and the caregiver leaves the room. As also indicated in block 188, the PSA receives information from the locating system that the caregiver has left the room and sends a message resulting in one or more of displays of bed 14, monitors 18, display boards 50, 58 of output devices 34, and the displays of mobile devices 60 being updated to indicate that the caregiver is out of the room and that the patient is in bed. Thereafter, data is captured from bed 14 relating to patient movement and the predictive analysis of bed exit at analytics engine 20 of the DSN platform 30 begins again as indicated at block 190 of FIG. 5B.

Based on the foregoing, it is apparent that data is generated by a number of devices 14, 16, 18 and other sources 12 as described above and sent to the analytics engine 20 of DSN platform 30. The algorithms of analytics engine establish a risk profile (e.g., risk scores) for each patient based on protocols established by a given healthcare facility. Some or all of the devices 14, 16, 18 and other sources 12 are updated with the risk profile information. In some embodiments, the sources 12 have displays that provide guided steps to caregivers that can be taken by the caregivers at the point of care to reduce or mitigate the risk profiles. The risk profiles for each patient are updated in substantially real time by the analytics engine as the incoming data changes. In some embodiments, the analytics engine 20 also sends data to other systems, such as IoT platform 64, for further analysis.

Figure 6:
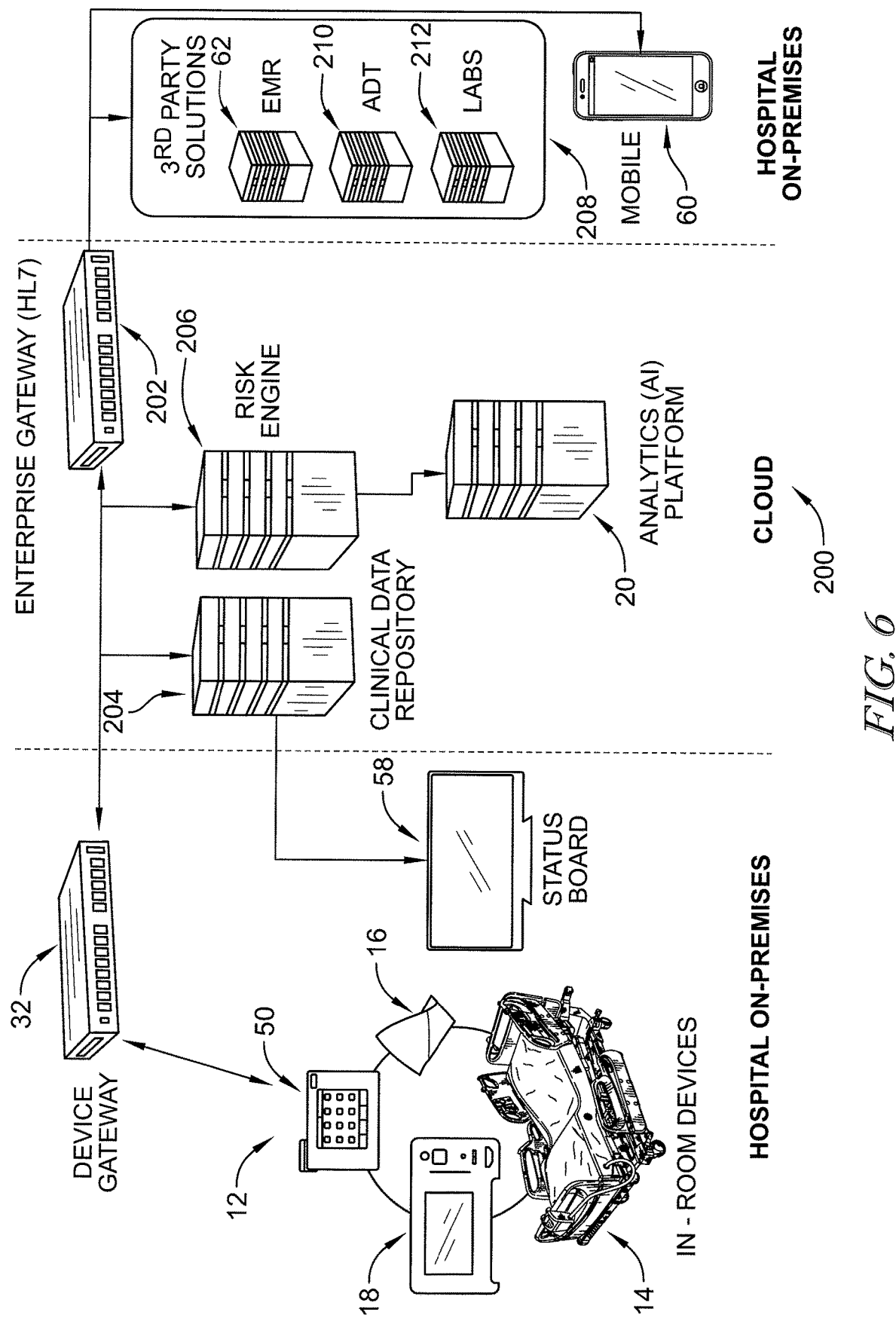
FIG. 6 is a diagrammatic view of an alternative system, similar to FIG. 3, showing hospital on-premises equipment at the left side of the page including in-room devices, a device gateway, and a status board; cloud devices at a center of the page including an enterprise gateway (HL7), a clinical data repository, a risk engine, and an analytics artificial intelligence (AI) platform; and additional on-premises equipment at the right side of the page including a mobile device and $3^{rd}$ party solutions including EMR, ADT, and Labs servers.

Referring now to FIG. 6, a diagrammatic view of another system 10, similar to FIG. 3, is provided and shows hospital on-premises equipment at the left side of the page including in-room devices 12, device gateway 32, and a status board 58. The illustrative in-room devices 12 of FIG. 6 include hospital bed 14, incontinence detection system 16, vital signs monitor 18, and room station 50. However, devices 12 of system 10 of FIG. 6 can include any other type of device 12 discussed herein. System 10 of FIG. 6 further includes cloud devices 200 at a center of the page including an enterprise gateway (HL7) 202, a clinical data repository 204, a risk engine 206, and analytics platform 20 that implements artificial intelligence (AI) to process data in some embodiments. Additional on-premises equipment of system 10 of FIG. 6 is shown at the right side of the page includes one or more mobile devices 60 and 3$^{rd}$ party solutions 208 including EMR server 62, an ADT server 210, and a Labs server 212.

As indicated in FIG. 6, messages and/or data transmitted to 3$^{rd}$ party solutions 208 from devices 12 via gateway 32 and from clinical data repository 204, risk engine 206, and analytics platform 20 pass through enterprise gateway (HL7) 202. Thus, gateway 202 converts the various messages and data into the health level 7 (HL7) format for subsequent delivery to the 3$^{rd}$ party devices 208 such as EMR, ADT, and Labs servers 62, 210, 212. In the embodiment of system 10 in FIG. 6, risk engine 206 manages the risk levels of the pressure injury risk score, falls risk score, and sepsis risk score based on the incoming data from devices 12 and the analytics platform (aka analytics engine) 20 analyzes the incoming data from devices 12 to determine correlations to the various patient risk scores.

According to the present disclosure, a multitude of devices 12 provide a multitude of types of data (e.g., patient data, vital signs data, physiological data, device data, etc.) to the analytics engine 20 which processes the data and determines one or more risk scores based on the data. The risk scores are adjusted substantially in real time as new data is received by the analytics engine 20. In the discussion above, risk scores relating to pressure injuries, falls, and sepsis were given as risk score examples. However, the present disclosure contemplates that other risk scores pertaining to other patient risks can be established at the discretion of a designer or programmer of system 10. In this regard, the following table is a list of the types of data (referred to as "risk factors" that may contribute to risk scores according to the present disclosure, including contributing to the risk scores relating to pressure injuries, falls, and sepsis:

TABLE 1

| Risk factor | rfid | rfid_type | Description | Type |
| --- | --- | --- | --- | --- |
| Abdominal Aortic Aneurysm Surgery | 1 | 0 | | Associated admission DX |
| Abdominal Respirations | 2 | 0 | | Clinical exam |
| Abnormal Lung Sounds | 3 | 0 | Diminished, wheezes, Crackles | Clinical exam |
| Accessory Muscle Use | 4 | 1 | | Patient symptoms |
| Accessory Muscle Use | 4 | 2 | intracostals and Sub-clavicular retractions | Clinical exam |
| Acute Myocardial Ischemia | 5 | 0 | | Associated admission DX |
| Acute Pancreatitis | 6 | 0 | | Associated admission DX |
| Age | 7 | 0 | | Demographics |
| Autoimmune disease, acquired autoimmune disease, acquired immune deficiency syndrome (AIDS), Immune Suppression or HIV | 8 | 0 | | Comorbidities |
| Albumin | 9 | 0 | | Labs |
| Altered mental status or Confusion | 10 | 0 | | Patient symptoms |
| Anemia | 11 | 0 | | Comorbidities |
| Anticoagulants (IV or SC) ex. heparin, lovenox | 12 | 0 | | Medications |
| Anxiety | 13 | 0 | | Patient symptoms |
| Any delivery other than cannula (venturi, rebreather, Non-Rebreather, CPAP, BiPAP) | 14 | 0 | | Charted MD orders |
| Any New Complaint in last 24 hrs | 15 | 0 | | Patient symptoms |

TABLE 1-continued

| Risk factor | rfid | rfid_type | Description | Type |
|---|---|---|---|---|
| Arterial Blood Gases | 16 | 0 | | Charted MD orders |
| Arterial PaO2 | 17 | 0 | (Decreased) | Labs |
| Arterial PCO2 | 18 | 0 | (abnormal) | Labs |
| Arterial Ph (Acidosis) | 19 | 0 | | Labs |
| Aspiration | 20 | 0 | | Associated admission DX |
| Asthma | 21 | 1 | | Associated admission DX |
| Asthma | 21 | 2 | | Comorbidities |
| Blood Transfusion | 22 | 0 | | Procedures |
| Brain Natriuretic Peptide | 23 | 0 | (lab order) | Charted MD orders |
| Brain Natriuretic Peptide | 24 | 0 | (Elevated) | Labs |
| Breathing treatments | 25 | 0 | | Charted MD orders |
| Bronchodilators | 26 | 0 | | Medications |
| Bronchiectasis or atelectasis | 27 | 0 | | Associated admission DX |
| Bronchitis | 28 | 0 | | Associated admission DX |
| Blood Urea Nitrogen | 29 | 0 | BUN | Labs |
| Burns | 30 | 0 | | Associated admission DX |
| Cancer | 31 | 1 | | Associated admission DX |
| Cancer | 31 | 2 | | Comorbidities |
| Capillary refill time | 32 | 0 | >3 seconds | Clinical exam |
| Cardiac Ejection Fraction | 33 | 0 | (decreased) | Labs |
| Cardiac or Thoracic Surgery | 34 | 0 | | Associated admission DX |
| Cardiac Valve Disorder or Valvular Insufficiency | 35 | 0 | | Associated admission DX |
| Chemotherapy (aka Chemo) | 36 | 0 | | Associated admission DX |
| Chest pain | 37 | 0 | | Patient symptoms |
| Chest pressure or pain or Abnormal ECG | 38 | 0 | | Clinical exam |
| Chest x-ray | 39 | 0 | | Charted MD orders |
| Chronic Congestive Heart Failure or Congestive Heart Disease | 40 | 0 | | Comorbidities |
| Chronic Obstructive Pulmonary Disease | 41 | 0 | | Comorbidities |
| Congestive Heart Failure | 42 | 0 | | Associated admission DX |
| COPD Exacerbation | 43 | 0 | | Associated admission DX |
| Corticosteriods | 44 | 0 | | Medications |
| Cost of Prior care | 45 | 0 | | Demographics |
| Cough | 46 | 1 | | Clinical exam |
| Cough | 46 | 2 | | Patient symptoms |
| Creatinine | 47 | 0 | (Increased) | Labs |
| Cyanosis | 48 | 1 | | Clinical exam |
| Cyanosis | 48 | 2 | | Patient symptoms |
| Cystic Fibrosis | 49 | 0 | | Comorbidities |
| Decreased level of consciousness (LOC)(from AVPU of modified early warning score (MEWS) or Glasgow Coma Scale (GCS) or Facility specific or agitation or encephalopathy) | 50 | 0 | | Clinical exam |
| Deep Vein Thrombosis | 51 | 0 | | Associated admission DX |
| Dementia | 52 | 0 | | Comorbidities |
| Diaphoresis (sweating) | 53 | 0 | | Patient symptoms |

TABLE 1-continued

| Risk factor | rfid | rfid_type | Description | Type |
|---|---|---|---|---|
| Diuretic Use | 54 | 0 | | Medications |
| Doppler Echocardiography (imaging) | 55 | 0 | | Charted MD orders |
| Drug Overdose | 56 | 0 | | Associated admission DX |
| Dyspnea | 57 | 0 | | Patient symptoms |
| Dyspnea at rest | 58 | 0 | | Associated admission DX |
| Emergency Surgery | 59 | 0 | | Associated admission DX |
| Emphysema | 60 | 0 | | Comorbidities |
| Alcohol (EtOH) Abuse or Drug Abuse including intravenous (IV) drug abuse | 61 | 0 | | Comorbidities |
| Hemoglobin | 62 | 0 | Low | Labs |
| Hematocrit | 63 | 0 | Low | Labs |
| Hemoptysis | 64 | 1 | | Associated admission DX |
| Hemoptysis | 64 | 2 | | Patient symptoms |
| High Emergency Department Use | 65 | 0 | | Demographics |
| High Fluid Rates or Volumes (I&O) | 66 | 0 | | Charted MD orders |
| High Fluid Rates or Volumes or Hypertonic Fluids | 67 | 0 | | Medications |
| Hx Coronary Artery Disease (CAD) | 68 | 0 | | Comorbidities |
| Hx Cerebral Vascular Accident (CVA) (Stroke) | 69 | 0 | | Comorbidities |
| Hx Pulmonary Emboli | 70 | 0 | | Comorbidities |
| Hx Sepsis | 71 | 0 | | Comorbidities |
| Insulin-Dependent Diabetes Mellitus (IDDM) (aka type 1 diabetes) | 72 | 0 | | Comorbidities |
| Interstitial Lung Disease | 73 | 0 | | Associated admission DX |
| Lactate (elevated) | 74 | 0 | | Labs |
| Long Term Care (LTC) Resident or Nursing Home Resident | 75 | 0 | | Demographics |
| Lung abscess | 76 | 0 | | Associated admission DX |
| Male | 77 | 0 | | Demographics |
| Morbid Obesity | 78 | 0 | | Comorbidities |
| Mottling of skin | 79 | 0 | | Clinical exam |
| Neck Surgery | 80 | 0 | | Associated admission DX |
| Neuro surgery, upper abd. or Peripheral Vascular Surgery | 81 | 0 | | Associated admission DX |
| Neuromuscular Disease | 82 | 0 | ALS, MS, Stroke, Spinal Cord Injury, Guillain-Barre, myasthenia Gravis | Comorbidities |
| New need or greater need for assist with ADLS | 83 | 0 | | Clinical exam |
| Non-White | 84 | 0 | | Demographics |
| Opioids | 85 | 0 | | Medications |
| Orthopnea | 86 | 0 | | Clinical exam |
| Peripheral edema | 87 | 0 | Ankles and legs | Clinical exam |
| Pneumonia | 88 | 0 | | Associated admission DX |
| Pneumothorax | 89 | 0 | | Associated admission DX |
| Polypharmacy | 90 | 0 | | Demographics |
| Prior Functional Status | 91 | 0 | | Demographics |

TABLE 1-continued

| Risk factor | rfid | rfid_type | Description | Type |
|---|---|---|---|---|
| Prior Intubation | 92 | 0 | | Comorbidities |
| Fatigue (acute or profound) | 93 | 0 | | Patient symptoms |
| Pulmonary Consult | 94 | 0 | | Charted MD orders |
| Pulmonary Emboli | 95 | 0 | | Associated admission DX |
| Pulmonary Function Test | 96 | 0 | (One or more Abnormals) | Labs |
| Pulmonary Hypertension | 97 | 0 | | Associated admission DX |
| Pulmonary-Renal Syndrome | 98 | 0 | | Associated admission DX |
| Pulmonary Function Testing | 99 | 0 | | Charted MD orders |
| Recent hospitalization | 100 | 0 | hospitalization within 90 days | Demographics |
| Renal Failure | 101 | 0 | | Associated admission DX |
| Respiratory rate | 102 | 0 | | Vitals |
| Restlessness | 103 | 0 | | Patient symptoms |
| Scoliosis | 104 | 0 | | Comorbidities |
| Sedatives or hypnotics or muscle relaxants | 105 | 0 | | Medications |
| Sepsis | 106 | 0 | | Associated admission DX |
| Shock | 107 | 0 | cardiogenic, Septic, etc | Associated admission DX |
| Sleep Apnea | 108 | 1 | | Associated admission DX |
| Sleep Apnea | 108 | 2 | | Comorbidities |
| Smoke Inhalation Injury | 109 | 0 | | Associated admission DX |
| Smoker | 110 | 0 | | Comorbidities |
| SpO2 | 111 | 0 | On Room Air or decreasing | Vitals |
| Sputum production | 112 | 1 | | Clinical exam |
| Sputum production | 112 | 2 | | Patient symptoms |
| Supplemental O2 or anything other than nasal cannula | 113 | 0 | | Vitals |
| Surgery including elective surgery | 114 | 1 | Any recent surgery | Associated admission DX |
| Surgery including elective surgery | 114 | 2 | Any surgery during admission | Procedures |
| Tachycardia | 115 | 1 | Heartrate (HR) > 90 beats per minute | Vitals |
| Tachycardia | 115 | 2 | Heartrate (HR) > 90 beats per minute | Patient symptoms |
| Tachypnea | 116 | 0 | Respiration rate (RR) > 20 or 22 breaths per minute | Patient symptoms |
| Thoracentesis | 117 | 0 | | Procedures |
| Transfer from Outside ED | 118 | 0 | | Demographics |
| Transfer from Higher level of Care | 119 | 0 | | Demographics |
| Trauma | 120 | 0 | | Associated admission DX |
| Troponin | 121 | 0 | (elevated) | Labs |
| VQ Scan or Thoracic CT Scan | 122 | 0 | (imaging) | Charted MD orders |
| Weight loss | 123 | 0 | >10% (six months) | Demographics |
| Chronic infectious disease | 124 | 0 | | Other |
| Lethargy | 125 | | | Patient symptoms or Associated admission DX |
| Delirium | 126 | 0 | | Associated admission DX or Clinical exam or Comorbidities |
| Fluid overload | 127 | 0 | | Clinical exam or Medications or Labs |
| Abscess | 128 | 0 | | Associated admission DX |

TABLE 1-continued

| Risk factor | rfid | rfid_type | Description | Type |
|---|---|---|---|---|
| Abdominal pain | 129 | 0 | | Associated admission DX |
| Abdominal tenderness | 130 | 0 | | Associated admission DX |
| Acute Lung Injury | 131 | 0 | | Associated admission DX |
| Transfer from ICU | 132 | 0 | | Demographics |
| Recent, Prior, or Acute Antibiotics | 133 | 0 | | Medications |
| Appendicitis | 134 | 0 | | Associated admission DX |
| Asplenic | 135 | 0 | | Comorbidities |
| Bacteremia | 136 | 0 | | Associated admission DX |
| Bilirubin | 137 | 0 | >/=1.2 mg/dL (or 20 mmol), ALT and AST also elevated | Labs |
| Bone marrow transplant | 138 | 0 | | Comorbidities |
| C-reactive protein | 139 | 0 | >2 sd over normal | Labs |
| Cardiac Output | 140 | 0 | Increased (early) decreased later as CO drops from volume depletion | Clinical Exam |
| Cellulitis | 141 | 0 | | Associated admission DX |
| Cholangitis | 142 | 0 | | Associated admission DX |
| Cholecystitis | 143 | 0 | | Associated admission DX |
| Cirrhosis | 144 | 0 | | Comorbidities |
| Colitis | 145 | 0 | | Associated admission DX |
| Cystitis | 146 | 0 | | Associated admission DX |
| D-dimer | 147 | 0 | | Labs |
| Decrease in daily functions | 148 | 0 | | Demographics |
| Dehydration | 149 | 0 | | Associated admission DX |
| Dialysis | 150 | 0 | | Comorbidities |
| Diverticulitis | 151 | 0 | | Associated admission DX |
| Diverticulosis | 152 | 0 | | Comorbidities |
| Early state warm and red skin, late state cool and pale w/mottling | 153 | 0 | | Clinical exam |
| Encephalitis | 154 | 0 | | Associated admission DX |
| Encephalopathy | 155 | 0 | | Associated admission DX |
| Endocarditis | 156 | 0 | | Associated admission DX |
| Fever | 157 | 0 | | Clinical exam |
| Fever of unknown origin | 158 | 0 | | Associated admission DX |
| Gastroenteritis | 159 | 0 | | Associated admission DX |
| Gastrointestinal bleed | 160 | 0 | | Associated admission DX |
| Gastrointestinal tract infection | 161 | 0 | | Associated admission DX |
| Glucose | 162 | 0 | Increased (early in diabetic or elevated in non-diabetic) >140 mg/dL | Labs |
| Bicarbonate (HCO3) | 163 | 0 | Low (early) | Labs |
| Headache, Stiff neck | 164 | 0 | | Clinical exam |
| Heart valve disorders | 165 | 0 | (including artificial valves) | Comorbidities |
| Hyperlactatemia | 166 | 0 | >1 mmol/L | Labs |
| Hypothermia | 167 | 0 | | Clinical exam |
| Hypotension | 168 | 0 | Symptom based admission | Associated admission DX |

TABLE 1-continued

| Risk factor | rfid | rfid_type | Description | Type |
|---|---|---|---|---|
| Ileus | 169 | 0 | | Clinical exam |
| Immunosuppressants | 170 | 0 | | Medications |
| Infectious process | 171 | 0 | | Associated admission DX |
| Inflammatory bowel disease | 172 | 0 | | Comorbidities |
| International normalized ratio (INR) for blood clotting | 173 | 0 | >1.5 | Labs |
| Jaundice | 174 | 0 | | Clinical exam |
| Joint Replacement | 175 | 0 | | Comorbidities |
| Leukopenia | 176 | 0 | | Comorbidities |
| Malaise | 177 | 0 | Symptom based admission | Associated admission DX |
| Malignancy | 178 | 0 | | Comorbidities |
| Mean arterial pressure | 179 | 0 | <70 | Vitals |
| Meningitis | 180 | 0 | | Clinical exam |
| Neoplasm | 181 | 0 | | Comorbidities |
| Normal white blood count (WBC) with >10% neutrophils (bands) | 182 | 0 | | Labs |
| Oliguria (decreased or low urine output) | 183 | 0 | (<0.5 ml/kg/hr) × 2 hrs or (500 ml/day) | Clinical exam |
| Organ transplant | 184 | 0 | | Comorbidities |
| Osteomyelitis | 185 | 0 | | Associated admission DX |
| Ostomy | 186 | 0 | | Associated admission DX |
| PaCO2 | 187 | 0 | <32 | Labs |
| PaO2 | 188 | 0 | <400 | Labs |
| PaO2/FiO2 | 189 | 0 | <300 | Vitals |
| Pelvic pain | 190 | 0 | | Associated admission DX |
| Peripheral vascular disease | 191 | 0 | | Comorbidities |
| Peripheral cyanosis | 192 | 0 | | Clinical exam |
| Petechial rash | 193 | 0 | | Clinical exam |
| Ph | 194 | 0 | Increase early d/t resp alkalosis then decrease later d/t metabolic acidosis | Labs |
| Platelets | 195 | 0 | <150 | Labs |
| Positive fluid balance | 196 | 0 | >20 ml/kf ocwe 24 hours | Clinical exam |
| Pre-existing or current renal disease | 197 | 0 | | Associated admission DX or Comorbidities |
| Pressure injury | 198 | 0 | | Comorbidities |
| Procalcitonin | 199 | 0 | Elevated >2 sd over normal | Labs |
| Protein in urine | 200 | 0 | Azotemia | Labs |
| Partial thromboplastin time (PTT) | 201 | 0 | >60 s | Labs |
| Pyelonephritis | 202 | 0 | | Associated admission DX |
| Recent abortion | 203 | 0 | | Comorbidities |
| Recent childbirth | 204 | 0 | | Comorbidities |
| Recent surgery (including dental) | 205 | 0 | | Demographic |
| Respiratory infection | 206 | 0 | | Associated admission DX |
| Seizures | 207 | 0 | | Clinical exam or comorbidities |
| Septic arthritis | 208 | 0 | | Associated admission DX |
| Sickle cell anemia | 209 | 0 | | Comorbidities |
| Soft tissue infection | 210 | 0 | | Associated admission DX |
| Stupor | 211 | 0 | | Clinical exam |
| Surgical admission | 212 | 0 | | Associated admission DX |

TABLE 1-continued

| Risk factor | rfid | rfid_type | Description | Type |
|---|---|---|---|---|
| Syncope (fainting) | 213 | 0 | | Other |
| Systolic blood pressure (SBP) | 214 | 0 | <100 or change from baseline SBP drop 40 pt from baseline | Vitals |
| Temperature | 215 | 0 | >38° Celsius (C.) or <36° C. | Vitals |
| Terminal illness | 216 | 0 | Any | Comorbidities |
| Volume depletion | 217 | 0 | Nausea, vomiting, diarrhea | Clinical exam |
| White blood cell count | 218 | 0 | <4000 or >12000 | Labs |
| Wound | 219 | 0 | | Associated admission DX |
| Acute respiratory distress syndrome | 220 | 0 | | Associated admission DX |

It should be noted that some risk factors in Table 1 appear twice but are designated in a separate column as either risk factor identification (rfid) type (rfid_type) 1 or rfid_type 2, with the others having rfid_type 0. The two different types of risk factors mean, for example, that there are multiple sources from which the risk factor may be obtained or, in some instances, that the risk factor is based on gender (e.g., male or female). One or more of the risk factors in Table 1 are selectable in a spread sheet to set up a risk rule that is implemented by the analytics engine 20 in system 10. An example of such risk rules that may be established include determining with the analytics engine 20 that the patient may be at risk of developing respiratory distress if any of the following conditions are met: (1) the patient is 70 years of age or older and has COPD; (2) the patient has COPD and has been prescribed opioids; (3) the patient is 70 years of age or older and has been prescribed opioids; (4) the patient is 70 years of age or older, has asthma, and has a blood urea nitrogen (BUN) of greater than or equal to 30 milligrams (mg) per 100 milliliters (ml) of blood; or (5) any four of the patient conditions listed in Table 1 are present. Further examples of such risk rules that may be established include determining with the analytics engine 20 that the patient may be at risk of developing sepsis if any of the following conditions are met: (1) the patient is 65 years of age or older and has cancer; or (2) the patient has a history of developing sepsis.

It is within the scope of the present disclosure for risk rules to be established based on any number of the risk factors set forth in Table 1 and, with regard to those risk factors that pertain to dynamically measurable parameters such as patient physiological parameters (e.g., those indicated at Vitals in the Type column of Table 1), the risk rules can be based on the particular measurable parameter being above or below a threshold criteria. Thus, the present disclosure contemplates that assessing medical risks of a patient includes receiving at the analytics engine 20 patient demographics data of the patient including, for example, at least one of age, race, and weight as shown in Table 1. The analytics engine 20 also receives comorbidity data of the patient in some embodiments including data indicating that the patient has at least one of the following medical conditions or characteristics: acquired immunodeficiency syndrome (AIDS), anemia, chronic congestive heart failure, asthma, cancer, chronic obstructive pulmonary disease (COPD), coronary artery disease, cystic fibrosis, dementia, emphysema, alcohol or drug abuse, stroke, pulmonary emboli, a history of sepsis, type 1 diabetes, morbid obesity, neuromuscular disease, prior intubation, scoliosis, smoker, delirium, asplenic, bone marrow transplant, cirrhosis, dialysis, diverticulosis, heart valve disorders, inflammatory bowel disease, joint replacement, leukopenia, malignancy, neoplasm, organ transplant, peripheral vascular disease, renal disease, pressure injury, recent abortion, recent childbirth, seizures, sickle cell anemia, or terminal illness.

In some embodiments, the analytics engine 20 also receives physiological data that may be measured by a physiological monitor that may have at least one sensor coupled to, or in communication with, the patient. The physiological data includes data that is dynamic and changing over time while the patient is being monitored by the physiological monitor. For example, the physiological data includes one or more of the following: heartrate, respiration rate, temperature, mean arterial pressure, systolic blood pressure, or pulse oximetry data including peripheral capillary oxygen saturation (SpO2). In some embodiments, the analytics engine 20 calculates a risk score or performs a risk assessment of the patient in substantially real time based on one or more of the patient demographics data, the comorbidity data, and the physiological data.

The analytics engine 20 also receives laboratory data of the patient in some embodiments and uses the laboratory data in connection with calculating the risk score. As shown in Table 1, examples of the laboratory data includes data that pertains to one or more of the following: albumin, arterial partial pressure of oxygen (arterial PaO2), arterial partial pressure of carbon dioxide (PCO2), arterial pH, acidosis, brain natriuretic peptide, blood urea nitrogen, cardiac ejection fraction, creatinine, hemoglobin, hematocrit, lactate, pulmonary function test, troponin, bilirubin, C-reactive protein, D-dimer, glucose, bicarbonate (HCO3), hyperlactatemia, international normalization ratio (INR) for blood clotting, normal white blood count (WBC) with greater than 10% neutrophils, arterial partial pressure of carbon dioxide (PaCO2), fluid overload, Ph, platelets, procalcitonin, protein in urine, partial thromboplastin time (PTT) or white blood cell count. Alternatively or additionally, the analytics engine 20 receives patient symptoms data of the patient and uses the patient symptoms data in connection with calculating the risk score. As shown in Table 1, examples of the patient symptoms data includes data that pertains to one or more of the following: accessory muscle use, altered mental status, confusion, anxiety, chest pain, cough, cyanosis, diaphoresis, dyspnea, hemoptysis, fatigue, restlessness, sputum production, tachycardia, tachypnea, or lethargy.

Further alternatively or additionally, the analytics engine 20 receives clinical examination data and uses the clinical examination data in connection with calculating the risk score. As shown in Table 1, examples of the clinical examination data includes data pertaining to one or more of the following: abdominal respirations, abnormal lung sounds, accessory muscle use, capillary refill, chest pressure or pain, abnormal electrocardiograph (ECG or EKG), cough, cyanosis, decreased level of consciousness (LOC), agitation, encephalopathy, mottling, need for assistance with activities of daily living (ADLS), orthopnea, peripheral edema, sputum production, delirium, fluid overload, cardiac output, early state warm red skin and late state cool and pale with mottling, fever, headache, stiff neck, hypothermia, ileus, jaundice, meningitis, oliguria, peripheral cyanosis, petechial rash, positive fluid balance, seizures, stupor, or volume depletion.

Still further alternatively or additionally, the analytics engine 20 receives charted doctor's orders data and uses the charted doctor's order data in connection with calculating the risk score. As shown in Table 1, examples of the charted doctor's orders data includes data that pertains to one or more of the following: delivery of breathing air other than with a cannula including with a Venturi, a rebreather, a non-rebreather, a continuous positive airway pressure (CPAP) machine, and a bi-level positive airway pressure (bi-PAP) machine; testing of arterial blood gases; testing of brain natriuretic peptide; breathing treatments; chest x-ray; Doppler echocardiography; high fluid rates or volumes (input and output (I&O)); pulmonary consultation; pulmonary function testing; ventilation-perfusion (VQ) scan; or thoracic computerized tomography (CT) scan.

In some embodiments, the analytics engine 20 also receives admission data for the patient and uses the admission data in connection with calculating the risk score. As shown in Table 1, examples of the admission data includes data that pertains to one or more of the following: abdominal aortic aneurysm surgery, acute myocardial ischemia, acute pancreatitis, aspiration, asthma, bronchiectasis, atelectasis, bronchitis, burns, cancer, cardiac or thoracic surgery, cardiac valve disorder or valvular insufficiency, chemo therapy, congestive heart failure, COPD exacerbation, deep vein thrombosis, drug overdose, dyspnea at rest, emergency surgery, hemoptysis, interstitial lung disease, lung abscess, neck surgery, neuro surgery, upper abdomen surgery, peripheral vascular surgery, pneumonia, pneumothorax, pulmonary emboli, pulmonary hypertension, pulmonary-renal syndrome, renal failure, sepsis, shock, sleep apnea, smoke inhalation injury, surgery, thoracentesis, trauma, lethargy, delirium, abscess, abdominal pain, abdominal tenderness, acute lung injury, appendicitis, bacteremia, cellulitis, cholangitis, cholecystitis, colitis, cystitis, dehydration, diverticulitis, encephalitis, encephalopathy, endocarditis, fever of unknown origin, gastroenteritis, gastrointestinal bleed, gastrointestinal tract infection, hypotension, infectious process, malaise, osteomyelitis, ostomy, pelvic pain, renal disease, pyelonephritis, respiratory infection, septic arthritis, soft tissue infection, surgical admission, wound, or acute respiratory distress syndrome.

Alternatively or additionally, the analytics engine 20 receives medications data for the patient and uses the medications data in connection with calculating the risk score. As shown in Table 1, examples of the medications data includes data that pertains to one or more of the following: anticoagulants including heparin or levenox that may be delivered intravenously (IV) or subcutaneously (SC), bronchodilators, corticosteroids, diuretic use, high fluid rates or volumes or hypertonic fluids, opioids, sedatives, hypnotics, muscle relaxants, fluid overload, antibiotics, or immunosuppressants.

Based on the forgoing, it should be appreciated that the present disclosure contemplates a method implemented on at least one computer such one or more of analytics engine 20 and other servers such as servers 62, 210, 212, 206. In the discussion that follows, it will be assumed that analytics engine 20 implements the various algorithms and functions. According to the method, the analytics engine 20 receives dynamic clinical variables and vital signs information of a patient. The analytics engine 20 uses the vital signs information to develop prior vital signs patterns and current vital signs patterns and then compares the prior vital signs patterns with the current vital signs patterns. The analytics engine 20 also receives one or more of the following: static variables of the patient, subjective complaints of the patient, prior healthcare utilization patterns of the patient, or social determinants of health data of the patient. The analytics engine 20 uses the dynamic clinical variables, the vital signs information, the results of the comparison of the prior vital signs patterns with the current vital signs patterns, and the one or more of the static variables, the subjective complaints, the healthcare utilization patterns, or the social determinants of health data in an algorithm to detect or predict that the patient has sepsis or is likely to develop sepsis.

In some embodiments, the dynamic clinical variables received by the analytics engine 20 includes point-of-care lab data. Optionally, the static variables received by the analytics engine 20 includes comorbidities. Alternatively or additionally, the static variables received by the analytics engine 20 includes whether the care setting of the patient is a pre-acute care setting, an acute care setting, or a post-acute care setting. If desired, the analytics engine 20 also receives historical data of the patient.

It is within the scope of the present disclosure for the analytics engine 20 to output one or more recommended actions to one or more clinicians of each of the patients being monitored. Examples of the one or more recommended actions include, for example, sending the patient to an emergency department (ED), increasing monitoring of the patient by the one or more clinicians, or ordering a set of labs for the patient.

In some embodiments, the analytics engine 20 ranks the clinicians of a healthcare facility. For example, the analytics engine 20 ranks the clinicians of the healthcare facility by one or more of experience, actions previously taken, and prior patient outcomes. Optionally, the actions that have greatest impact on outcomes may be used by the analytics engine 20 to inform newer or less experienced clinicians how an experienced clinician may attend to the patient.

It is contemplated by the present disclosure that artificial intelligence (AI) and machine learning is used by the analytics engine 20 to analyze risk factor data of the type listed in Table 1 and to determine correlations between one or more of the risk factors and particular risks such as pressure injuries, falls, and sepsis, as well as other risks for patients. Risk factors that are highly correlated to particular risks are then used to established risk rules based on two or more of the highly-correlative risk factors.

As discussed above in connection with FIGS. 3 and 6, mobile devices 60 of caregivers are among the output devices 34 on which risk scores and risk data are displayed. FIGS. 7-10 show screen shot examples of the type of information displayed on mobile devices 60 of caregivers. The examples of FIGS. 7-10, in some embodiments, are contemplated as being provided by additional software functionality of the LINQ™ mobile application available from Hill-Rom Company, Inc. Additional details of the LINQ™ mobile application can be found in U.S. application Ser. No. 16/143,971, filed Sep. 27, 2018, titled "Caregiver and Staff Information System," published as U.S. Patent Application Publication No. 2019/0108908 A1, and which is hereby incorporated by reference herein.

Referring now to FIG. 7, an example of a Patient screen 220 of a mobile application displayed on a touch screen display of mobile devices 60 of FIGS. 3 and 6 includes a My Patients button or icon 222 and a My Unit 224 button or icon near the top of screen 220. In the illustrative example, the My Patients icon 222 has been selected and, as a result, screen 220 includes a list 226 of the patients assigned to the caregiver of the mobile device 60 on which screen 220 is shown. Each of the caregiver's assigned patient's is shown in a separate row of the list 226 and includes the patient's name and the room in the healthcare facility to which the patient has been assigned. Beneath each of the patient's room number and name, one or more risk scores and associated information is shown, when applicable. If the My Unit button 224 is selected, then similar information is shown on the display screen of the mobile device 60 for all patients in the unit of the healthcare facility to which the caregiver is assigned, including patients assigned to other caregivers of the unit.

In the illustrative example of screen 220 in FIG. 7, beneath the text "2160 HILL, LARRY" in the first line of list 226, a first risk score box 228 shows a systemic inflammatory response syndrome (SIRS) score having a value of 4 and a second risk score box 230 shows a modified early warning score (MEWS) scored having a value of 5. Also in the illustrative example, an up arrow icon 232 is shown to the left of each of boxes 228, 230 in the first row of list 226 to indicate that the SIRS and MEWS scores have both increased as compared to their prior readings. In the illustrative example, "@ 9:20" appears to the right of the text "MEWS" in the first row of list to indicate the time that the MEWS score was most recently updated. In rows two through four of the illustrative example of list 226, only box 230 is shown with the MEWS score for the respective patient. The fifth row of list 226 has the text "2159 NO PATIENT" to indicate that room 2159 does not currently have any patient assigned to it, but if there was a patient assigned to room 2159, then that patient would be among the patients assigned to the caregiver of the mobile device 60 on which screen 220 is shown. Screen 220 also has a menu 234 of icons or buttons (these terms are used interchangeable herein) which is beneath list 226 and which includes a Home icon 236, a Contacts icon 238, a Messages icon 240, a Patients icon 242 and a Phone icon 244. Additional details of the screens and functions associated with icons 236, 238, 240, 242, 244 can be found in U.S. application Ser. No. 16/143,971, filed Sep. 27, 2018, published as U.S. Patent Application Publication No. 2019/0108908 A1, and which is already incorporated by reference herein.

Referring now to FIG. 8, an example is shown of a Risk Details screen 250 that appears on the touchscreen display of the caregiver's mobile device 60 in response to selection of one of the right arrow icons 252 of screen 220 at the right side of each row of list 226. In the illustrative example of FIG. 8, screen 250 shows risk details for patient Larry Hill as indicated at the top of screen 250. A left arrow icon 254 is provided to the left of the text "PATIENTS 2160 HILL, L." at the top of screen 250 and is selectable to return the caregiver back to screen 220. In the illustrative example of screen 250, phone icon 244 no longer appears in menu 234 but rather appears at the top right of screen 250. The other icons 236, 238, 240, 242 remain in menu 234 at the bottom of screen 250.

Still near the top of screen 250, the patient's medical record number (MRN) is shown in field 256 and the patient's age is shown in field 258. In the illustrative example, the patient's MRN is 176290 and the patient is 76 years old. Beneath field 256 of screen 250, three status icons are shown. In particular, a falls risk icon 260, a pulmonary risk icon 262, and a pressure injury icon 264 is shown. If the patient is determined to be at risk of falling, then icon 260 is highlighted. If the patient is determined to be at risk for respiratory distress, then icon 262 is highlighted. If the patient is determined to be at risk of developing a pressure injury, then icon 264 is highlighted. Icons 260, 262, 264 are grayed out or are absent if the corresponding patient is determined not to have the associated risk.

With continued reference to FIG. 8, a MEWS window 266 is shown beneath icons 260, 262, 264 and has additional information pertaining to the MEWS score appearing in box 230. Box 230 and up arrow icon 232 appear at the left side of window 266. To the right of box 230 and icon 232 in window 266, various vital signs information that relate to or contribute to the MEWS score are shown. In the illustrative example of screen 250, the patient, Larry Hill, has a temperature of 100.6° Fahrenheit (F), an SPO2 of 92%, a non-invasive blood pressure (NIBP) of 200/96 mmHg, a heart rate (HR) of 118 beats per minute (BPM), and a respiration rate (RR) of 26 breaths per minute (BPM). Up arrow icons 267 appear in window 266 to the right of any of the vital signs that have increased since the prior reading.

According to this disclosure, the data needed to calculate the MEWS is obtained from sensors included as part of medical devices 12 such as patient beds 14 and vital signs monitors 18, and/or is received as manual user inputs based on clinical insights 24 of caregivers, and/or obtained from the person's EMR of EMR server 62. The MEWS is a known score calculated based on the following table:

TABLE 2

| Score | 3 | 2 | 1 | 0 | 1 | 2 | 3 |
|---|---|---|---|---|---|---|---|
| Systolic BP | <70 | 71-80 | 81-100 | 101-199 | — | >200 | — |
| Heart rate (BPM) | — | <40 | 41-50 | 51-100 | 101-110 | 111-129 | >130 |
| Respiratory rate (RPM) | — | <9 | — | 9-14 | 15-20 | 21-29 | >30 |
| Temperature (° C.) | — | <35 | — | 35.0-38.4 | — | >38.5 | — |
| AVPU | — | — | — | A | V | P | U |

In Table 2, the various integers in the column headings are added together based on the various readings for the person of the data corresponding to the rows of the table. A score of 5 or greater indicates a likelihood of death. With regard to the systolic blood pressure, heart rate, respiratory rate, and temperature portions of the MEWS, those pieces of information are obtained using sensors of patient beds 14 and/or using the other manners of obtaining a person's physiological data as discussed above. The AVPU portion of the MEWS indicates whether a person is alert (A), responsive to voice (V), responsive to pain (P), or unresponsive (U). A caregiver selects the appropriate AVPU letter for each patient and enters it into a computer such as room station 50, their mobile device 60, or another computer of system 10 such as a nurse call computer, an EMR computer, an ADT computer, or the like.

Still referring to screen 250 of FIG. 8, a Sepsis-Related Organ Failure Assessment (SOFA) window 268 is shown beneath window 266 and has information pertaining to a SOFA score. At the left side of window 268 a risk score box 270 shows the SOFA score value, 2 in the illustrative example, and an up arrow icon 272 indicates that the SOFA score has increased as compared to the previous score. To the right of box 270 and icon 272 in window 268, the patient's physiological parameters that contribute or relate to the SOFA score are shown. In the illustrative example, the patient has platelets of 145 per microliter (μL), an output/input of 800 milliliters per day, and a cardiovascular (CV) of 58 mean arterial pressure (MAP).

A MORSE window 274 having information pertaining to a MORSE Fall Scale (MFS) score or value is shown on screen 250 of FIG. 8 beneath window 268. At the left side of window 274 a risk score box 276 shows the MORSE or MFS score value, 3 in the illustrative example. There is no up arrow icon or down arrow icon shown next to box 276 thereby indicating that the MORSE score has not changed since the previous reading. To the right of box 276 are risk factors that contribute or relate to the MORSE score. In the illustrative example, the patient's mobility risk factors include the patient being vision impaired and having a hip replacement and the patient's medications risk factors include that the patient is prescribed a sedative. In each of windows 266, 268, 274, the time at which the score in the respective risk score box 230, 270, 276 was most recently updated is indicated beneath the respective box 230, 270, 276.

As shown in FIG. 8, screen 250 includes a pair of Risk Contributors windows including a respiratory distress window 278 listing factors contributing or relating to a risk that the patient will experience respiratory distress and a sepsis window 280 listing factors contributing or relating to the patient's risk of developing sepsis. In the illustrative example, the risk factors in respiratory distress window 278 include the patient having chronic obstructive pulmonary disease (COPD), the patient being over 65 years of age, and the patient being a smoker, and the risk factors in the sepsis window 280 include the patient having a urinary tract infection (UTI) and the patient being over 65 years of age. The example of FIG. 8 demonstrates that patient risk factors can be used in connection with multiple risk scores or risk contributors to the risk scores or risk determinations.

With regard to windows 266, 268, 274, some or all of these are color coded in some embodiments to indicate the severity level of the particular risk score or the particular risk factors relating to the risk scores or determinations. For example, the area around box 230 of window 266 and the border of window 266 is color coded red if the risk value in box 230 is 5 or greater to indicate that the patient is at a high amount of risk. Similarly, the area around boxes 270, 276 of windows 268, 274, respectively, is color coded yellow if the risk values in boxes 270, 276 indicate a medium amount of risk, as is the case in the illustrative example. The arrows 232, 267, 272 are also color coded in some embodiments, typically with a darker shade of red or yellow, as the case may be. If the risk score for any particular risk factor indicates a low level of risk, then the associated window on screen 250 is color coded green or some other color such as blue or black. Risk contributors windows 278, 280 are similarly color coded (e.g., red, yellow, green) in some embodiments, depending upon the number or severity of risk factors that are present for the particular patient. The individual numerical data or risk factors in windows 266, 268, 274 are also color coded in some embodiments.

Figures 9, 10:
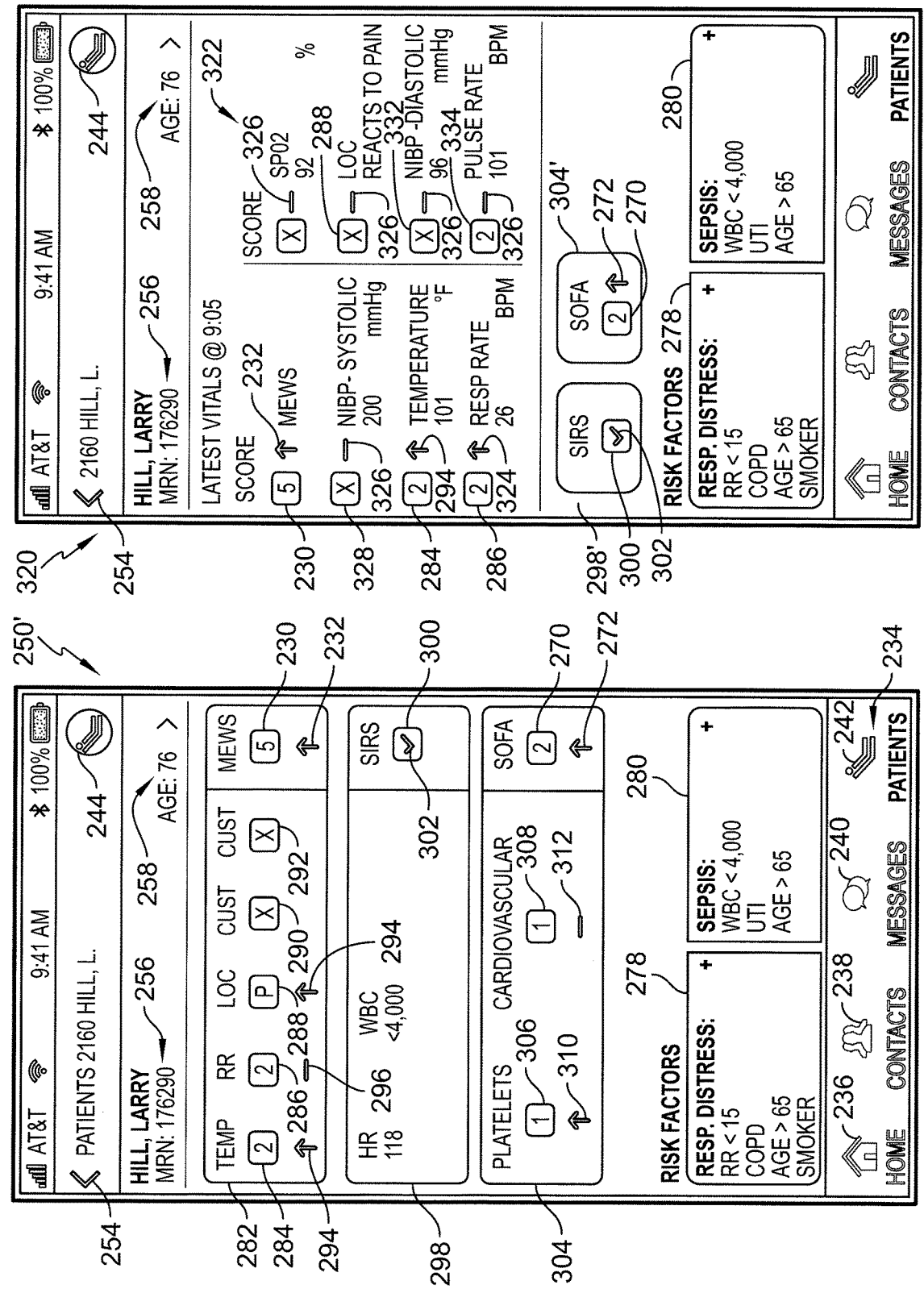
FIG. 9 is a screen shot example of an alternative Risk Details screen that, beneath the patient's name, includes MEWS, SIRS, and SOFA windows having sub-scores information, where applicable, that contribute to the overall score, and that also includes the pair of Risk Contributors windows similar to those of FIG. 8.
FIG. 10 is a screen shot example of a MEWS Details screen that provides greater details relating to the MEWS value including showing which vital signs or other information corresponds with each of the sub-score values that contribute to the overall MEWS value, the MEWS Details screen appearing on the caregiver's mobile device in response to selection of the MEWS window on the Risk Details screen of FIG. 8 or 9.

Referring now to FIG. 9, an example is shown of an alternative Risk Details screen 250' that appears on the touchscreen display of the caregiver's mobile device 60 in response to selection of one of the right arrow icons 252 of screen 220 at the right side of each row of list 226 of FIG. 7. Portions of screen 250' that are substantially the same as like portions of screen 250 are indicated with like references and the description above of these portions of screen 250 is equally applicable to screen 250'. In the illustrative example of FIG. 9, screen 250' shows risk details for patient Larry Hill as indicated at the top of screen 250' Beneath the MRN data 256 and age data 258 of screen 250' is a MEWS window 282. At the right side of window 282, the MEWS score box 230 and up arrow icon 232 is shown.

Window 282 includes a temperature score box 284, a respiration rate (RR) score box 286, a level of consciousness (LOC) score box 288, a first custom score box 290, and a second custom score box 292 as shown in FIG. 9. In the illustrative example, boxes 284, 286 each have a score of 2 and box 288 has the letter P from the AVPU score shown above in Table 2. Illustrative MEWS box 230 has a score of 5 in the illustrative example of screen 250' in FIG. 9, but really, the score should be shown as 6 assuming that the P in box 288 corresponds to a score of 2 as shown in Table 2. In the illustrative example of screen 250' up arrow icons 294 are shown beneath boxes 284, 288 to indicate that the temperature portion and the LOC portion, respectively, of the MEWS have each increased since the previous values used to calculate the previous MEWS. A dash icon 296 is shown in window 282 beneath box 286 to indicate that the patient's RR portion of the MEWS has not changed since the previous MEWS calculation.

The custom score boxes 290, 292 of window 282 indicate that a revised MEWS or amended MEWS is within the scope of the present disclosure. Thus, designers or programmers of system 10 for any given healthcare facility are able to pick other risk factors, such as those shown above in Table 1, that contribute to such a revised or amended MEWS. Just to give one example, age could be the risk factor chosen as corresponding to one of the boxes 290, 292. The score values based on age ranges are also at the discretion of the system designer or programmer. Thus, integers between 0 and 3 could be assigned to different age ranges just to give one arbitrary example (e.g., 20 year of age or younger=0; 21-40 years of age=1; 41-60 years of age=2; 61 years of age or older=3). Optionally, negative numbers for certain age ranges could be used. For example, 20 years of age or younger could be assigned an age score of −1 which would result in the illustrative score of 5 for such an amended MEWS score assuming the patient associated with window 282 is 20 years of age or younger (i.e., boxes 284, 286, 288 would add up to 6 and then with the −1 age score, the overall amended MEWS would be 5). Again, this is just an arbitrary example and it should be appreciated that there are practically limitless possibilities of risk factors from Table 1 and numerical score scenarios that could be chosen in connection with custom boxes 290, 292 of window 282 to create a revised or amended MEWS.

Still referring to screen 250' of FIG. 9, a systemic inflammatory response syndrome (SIRS) window 298 is shown beneath window 282. A SIRS score box 300 is shown at the right side of window 298 and a check mark 302 appears in box 300 to indicate that the patient is positive for SIRS. If the patient is negative for SIRS, then box 300 is blank. In the left side of window 298, the risk factors and associated data that have contributed or that relate to the positive SIRS determination for the patient are shown. In the illustrative example of screen 250', window 298 includes heart rate (HR) data of 118 beats per minute and a white blood count (WBC) less than 4,000. In some embodiments, the determination as whether or not the patient is positive for SIRS is based on the following table:

TABLE 3

| Systemic inflammatory response syndrome (SIRS) | |
| --- | --- |
| Finding | Value |
| Temperature | <36° C. (98.6° F.) or >38° C. (100.4° F.) |
| Heart rate | >90/min |
| Respiratory rate | >20/min or PaCO2 < 32 mmHg (4.3 kPa) |
| WBC | <4 × $10^9$/L (<4000/$mm^3$), >12 × $10^9$/L (>12,000/$mm^3$), or 10% bands |

In typical embodiments, if any two or more conditions indicated in the rows of table 3 is met, then the patient is considered to be positive for SIRS. In other embodiments, at the discretion of the system designer or programmer, two, three, or all four of the conditions indicate in table 3 need to be met before a patient is considered to be positive for SIRS. The present disclosure also contemplates that additional patient risk factors, such as those listed above in table 1, are used in connection with assessing patients for SIRS. It should be appreciated that there are practically limitless possibilities of risk factors from Table 1 and numerical score scenarios that could be chosen in connection with adding additional rows to table 3 or replacing one or more of the current rows of table 3 to create the criteria for the revised or amended SIRS assessment.

Some other factors that are commonly used in connection with a SIRS determination include suspected or present source of infection (SIRS+source of infection), severe sepsis criteria (organ dysfunction, hypotension, or hypoperfusion) indicated by lactic acidosis or SBP<90 or SBP drop ≥40 mmHg of normal, and evidence of ≥2 organs failing (multiple organ dysfunction syndrome criteria), just to name a few. In any event the SIRS value is sometimes displayed on mobile devices 60 as a numerical score indicating the number of SIRS risk factors that are met, and sometimes is displayed as a check mark that indicates that patient is considered to be positive for SIRS.

With continued reference to screen 250' of FIG. 9, a Sepsis-Related Organ Failure Assessment (SOFA) window 304 is shown beneath window 298. At the right side of window 304, the SOFA score box 270 and up arrow icon 272 is shown. These are basically the same as shown in window 268 of FIG. 8 and so the same reference numbers are used. However, unlike window 268 of screen 250 which shows numerical data for the risk factors that contribute to the SOFA score, window 304 of screen 250' has risk score boxes for each of the contributing risk factors. In the illustrative example, a platelets risk score box 306 and a cardiovascular risk score box 308 is shown in window 304 and each box 306, 308 has a score of 1 which, when added together, results in the overall SOFA risk score of 2 shown in box 270 of window 304.

In some embodiments of system 10, a quick SOFA (qSOFA) score is also determined and shown on the mobile devices 60 of caregivers. The qSOFA score may be shown in lieu of or in addition to the SOFA score. The following table 4 is used in connection with calculating the qSOFA score in some embodiments:

TABLE 4

| Assessment | qSOFA score |
| --- | --- |
| Low blood pressure (SBP ≤ 100 mmHg) | 1 |
| High respiratory rate (≥22 breaths/min) | 1 |
| Altered mentation (GCS ≤ 14) | 1 |

In some embodiments, one or more of the following tables are used in connection with calculating the SOFA score:

TABLE 5

| Respiratory system | |
| --- | --- |
| $PaO_2/FiO_2$ (mmHg) | SOFA score |
| ≥400 | 0 |
| <400 | +1 |
| <300 | +2 |
| <200 and mechanically ventilated | +3 |
| <100 and mechanically ventilated | +4 |

TABLE 6

| Nervous system | |
| --- | --- |
| Glasgow coma scale | SOFA score |
| 15 | 0 |
| 13-14 | +1 |
| 10-12 | +2 |
| 6-9 | +3 |
| <6 | +4 |

TABLE 7

| Cardiovascular system | |
| --- | --- |
| Mean arterial pressure OR administration of vasopressors required | SOFA score |
| MAP ≥ 70 mmHg | 0 |
| MAP < 70 mmHg | +1 |
| dopamine ≤ 5 μg/kg/min or dobutamine (any dose) | +2 |
| dopamine > 5 μg/kg/min OR epinephrine ≤ 0.1 μg/kg/min OR norepinephrine ≤ 0.1 μg/kg/min | +3 |
| dopamine > 15 μg/kg/min OR epinephrine > 0.1 μg/kg/min OR norepinephrine > 0.1 μg/kg/min | +4 |

TABLE 8

| Liver | |
| --- | --- |
| Bilirubin (mg/db) [μmol/L] | SOFA score |
| <1.2 [<20] | 0 |
| 1.2-1.9 [20-32] | +1 |
| 2.0-5.9 [33-101] | +2 |

TABLE 8-continued

Liver

| Bilirubin (mg/db) [μmol/L] | SOFA score |
|---|---|
| 6.0-11.9 [102-204] | +3 |
| >12.0 [>204] | +4 |

TABLE 9

Coagulation

| Platelets×10³/μl | SOFA score |
|---|---|
| ≥150 | 0 |
| <150 | +1 |
| <100 | +2 |
| <50 | +3 |
| <20 | +4 |

TABLE 10

Kidneys

| Creatinine (mg/dl) [μmol/L] (or urine output) | SOFA score |
|---|---|
| <1.2 [<110] | 0 |
| 1.2-1.9 [110-170] | +1 |
| 2.0-3.4 [171-299] | +2 |
| 3.5-4.9 [300-440] (or <500 ml/d) | +3 |
| >5.0 [>440] (or <200 ml/d) | +4 |

To calculate the overall qSOFA score, the score values in the right hand column of table 4 or, with regard to the SOFA score, the right hand column of whichever of tables 5-10 are being used in connection with the SOFA score, are added together. In the illustrative example of window 304, an up arrow icon 310 is shown beneath box 306 to indicate that the patient's platelets have increased since the previous platelets reading and a dash icon 312 is shown beneath box 308 to indicate that the patient's cardiovascular reading has not changed since the prior cardiovascular reading.

Screen 250' of FIG. 9 also has respiratory distress window 278 and sepsis window 280 which are basically the same as windows 278, 280 of screen 250 of FIG. 8 and so the same reference numbers are used. However, in addition to text indicating that the patient has COPD, is older than 65 years of age, and is a smoker, window 278 of FIG. 9 also indicates that the patient has a respiration rate less than 15 breaths per minute. Also, in addition to text indicating that the patient has a UTI and is older than 65 years of age, window 280 of FIG. 9 also indicates that the patient has a WBC less than 4,000. Similar to the color coding discussed above in connection with windows 266, 268, 274, 278, 280 of screen 250 of FIG. 8 and the information therein, windows 278, 280, 282, 298, 304 of screen 250' of FIG. 9 can be similarly color coded in some embodiments.

Referring now to FIG. 10, an example is shown of a MEWS Details screen 320 that provides greater details relating to the MEWS of screens 250, 250' of FIGS. 8 and 9. Thus, if the caregiver touches, taps, or swipes MEWS window 230 of screen 250 or MEWS window 282 of screen 250', then screen 320 appears on the touchscreen display of the caregiver's mobile device 60. Portions of screen 320 that are substantially the same as like portions of screens 220, 250, 250' of FIGS. 7-9, respectively, are indicated with like reference numbers and the description above is equally applicable to screen 320 with regard to the like portions.

Screen 320 has an expanded MEWS data window 322 beneath the MRN data 256 and age data 258. In the illustrative example, the SIRS and SOFA windows 298, 304 of screen 250' of FIG. 9 are minimized into smaller windows 298',304', respectively, beneath expanded MEWS data window 322. Windows 298',304' omit the risk factor data shown, for example, in windows 298, 304. However, windows 298',304' still show boxes 272, 300 with the respective SOFA score and SIRS check mark icon 302. The up arrow icon 272 is also still shown in window 304'. The expanded MEWS data window 322 includes the boxes 230, 284, 286, 288 that were shown in window 282, but the positions of these boxes has been rearranged and several other boxes, along with numerical data, are also shown in window 322. Up arrow icons 232, 294 are also shown in window 322 to the right of boxes 230, 284, respectively. In the illustrative example of screen 320, an up arrow icon 324 is shown to the right of box 286 and a dash icon 326 is shown to the right of box 288 in window 322.

Window 322 also includes a noninvasive blood pressure (NIBP)—systolic risk score box 328, an SPO2 risk score box 330, an NIBP—diastolic risk score box 332, and a pulse rate risk box 334. In the illustrative example, each of boxes 328, 330, 332 has an "X" to indicate that the numerical values of the associated patient physiological parameters do not contribute to the overall MEWS for the patient. In other embodiments, "0" appears in the respective boxes when the associated risk factor does not contribute to the MEWS of the patient. In the illustrative example, a risk score value of 2 appears in box 334. Dash icons 326 are shown to the right of each of boxes 328, 339, 332, 334 to indicate that the respective readings have not changed since the prior readings. The values in boxes 284, 286, 288, 328, 330, 332, 334 of window 322 are sub-scores that, when added together, provide the overall MEWS score for the patient. As noted above, risk factors from table 1 can be used to create a revised or amended MEWS (aka a customized MEWS) and in such instances, the selected risk factors from table 1 have associated risk score boxes and risk data in window 322. Similarly, relevant risk score boxes and data are also shown if windows 268, 264 of screen 250 of FIG. 8 or if windows 298, 304 of screen 250' of FIG. 9 are selected on the caregiver's mobile device 60 rather than window 266 of screen 250 or window 282 of screen 250'.

According to the present disclosure, an EMR plug-in in the form of a software module is provided in system 10 in some embodiments. The EMR plug-in is used by hospital administrators and caregivers to view a patient's deterioration (e.g., development of sepsis, respiratory distress, pressure injury, etc.) and falls risks giving users dynamic risk monitoring allowing earlier and more consistent identification of patient risk. The plug-in provides viewing of the risk scoring with additional context beyond conventional early warning scores (EWS's) and builds caregiver trust by providing criteria and reasoning behind the risk scoring. The EMR plug-in also indicates if there are missing parameters in a patient's deterioration risk score(s) on an ongoing basis so caregivers are informed of which risk parameters still need to be assessed and entered.

In some embodiments, the EMR plug-in is accessed via navigation in an EMR computer that is in communication with EMR server 62. The EMR computer launches a webpage provided by the EMR plug-in. The EMR plug-in is configured to assist in reducing/eliminating delays and communication shortcomings between care personnel/teams during an escalation event or handoff. A Situation, Background, Assessment, Recommendation (SBAR) feature is provided in the EMR plug-in and ensures that a patient's deterioration risk is promptly communicated to the appropriate caregivers upon a hand-off or escalation event to facilitate an efficient transfer of knowledge of the patient's deterioration risk.

With regard to calculating a falls risk score according to the present disclosure, additional details can be found in U.S. Provisional Patent Application No. 62/818,828, which was filed Mar. 15, 2019, and which is titled "Patient Fall Likelihood," and in U.S. Provisional Patent Application No. 62/818,836, which was also filed on Mar. 15, 2019, which is titled "Patient Fall Likelihood and Severity," and both of which are hereby incorporated by reference herein in their entirety to the extent not inconsistent with the present disclosure which shall control as to any inconsistencies. According to these two provisional patent applications, a falls risk score (or just, fall score) is determined based on the following formula:

fall score=immediate risk model score+attribute risk model score

The immediate risk model score is based on the following formula:

immediate risk model score=data1×weight1+data2× weight2+. . . data$N$×weight$N$ where the data can include activity at a given period of time (e.g., toileting during sleeping hours), a medication change, acute motion detected for the patient, etc. Thus, the immediate risk model score is a numerical quantification of the likelihood of an immediate fall with each relevant piece of data weighted and added to create the score. For example, the acute movement of the patient can be weighted more highly than change in medication.

The attribute risk model score is based on the following formula:

attribute risk model score=data1×weight1+data2× weight2+ . . . data$N$×weight$N$ where the data can include bibliographic/demographic information associated with the patient, such as history of falling, age, frequency or urgency of urination, type of medication taken, procedures under which the patient has gone, a gait analysis, etc. Thus, the attribute risk model score is a numerical quantification of the likelihood of a fall based on attributes of the patient collected over time with each relevant piece of data weighted and added to create the score. For example, the poor gait of the patient can be weighted more highly than motion of the patient in bed over time.

With regard to specific devices for detecting and monitoring sepsis according to the present disclosure, additional details can be found in U.S. Provisional Patent Application No. 62/825,844 ("the '844 application), filed Mar. 29, 2019, titled "Sepsis Detection and Monitoring," and which is hereby incorporated by reference herein in its entirety to the extent not inconsistent with the present disclosure which shall control as to any inconsistencies. The devices disclosed in the '844 application provide further examples of the type of medical devices 14 of system 10 that provide data to analytics engine 20. For example, the '844 application contemplates that an ECG or photoplethysmogram (PPG) or radar transmitter/receiver can detect heart rate variability of a patient and if the heart variability decreases, which is an indicator of the onset sepsis, the rate of acquiring vital signs data is increased. The '844 application incorporates by reference U.S. Provisional Patent Application No. 62/798,124, filed Jan. 29, 2019, for its disclosure of monitoring devices that use radar signals. Thus, U.S. Provisional Patent Application No. 62/798,124, filed Jan. 29, 2019, is hereby incorporated by reference herein, as well, in its entirety for the same purpose.

Further according to the '844 application, a fundus imaging system including a camera is used to capture images of the fundus (e.g., the retina, optic nerve, macula, vitreous, choroid and posterior pole) of a patient during a full cardiac cycle. The images are analyzed to determine whether the patient has microvascular dysregulation which is another indicator of the onset or existence of sepsis in the patient. The fundus imaging system can also be configured to measure the patient's flicker response by exposing the patient's retina to a flashing light and then measuring the reactivity of the retinal blood vessels which is diminished in septic patients due to neurovascular decoupling. Still further, the fundus imaging system can be configured to measure local oxygenation of the retina in connection with determining whether the patient has sepsis. The fundus imaging system can also be configured to measure blood flow velocity changes to detect that the patient is septic because blood vessel walls become "sticky" and blood cells become rigid causing sluggish blood flow in septic patients. The fundus imaging system further may be configured to measure blood vessel diameters and lumen to wall thickness ratios which change in response to dysregulated vasomotor reactions in septic patients. Based on the foregoing, therefore, it should be appreciated that the present disclosure contemplates that analytics engine 20 processes and analyzes image data from a fundus imaging system to make sepsis determinations in some embodiments.

Still further according to the '844 application, screening a patient for sepsis involves the use of PPG measurements, bio-impedance measurements, skin perfusion measurements, or temperature measurements at the patient's skin. During early onset of sepsis, vasodilation occurs at the endothelial level and stimuli applied at the patient's skin to produce these measurements causes less of a differential in vasodilation of septic patients than in non-septic patients. The '844 application discloses a temperature induction device that applies a range of temperatures to the patient's skin using a Peltier heater and cooler that heats or cools, respectively, the patient's skin based on a direction of current (e.g., a polarity of voltage applied) through the Peltier heater and cooler. A PPG sensor measures the patient's microvascular response to the changing temperatures. The PPG sensor includes infrared (IR) red and green light emitting diodes (LED's) in some embodiments.

The '844 application also discloses an impedance sensor including electrodes attached to the patient's skin surface through which a low voltage (up to 10 Volts) sinusoidal signal is applied via the patient's skin. The impedance of the patient's skin between the electrodes is determined after heating and cooling the skin with the temperature induction device. The measured electrical impedance is then used to determine the microvascular response. In another aspect of the '844 application, a portion of a patient support apparatus, such as a hospital bed, is moved to raise a patient's extremity and to determine whether a septic patient is responding to fluid resuscitation treatment. In some embodiments, a head section or leg section of a hospital bed is raised to determine the patient's macrovascular response which is done by using vital signs measurements to determine a response to the fluid shift away from the raised extremity and toward the patient's heart.

In addition to the risk factors or data elements of Tables 1-10 above, the present disclosure contemplates that any one or more of the data elements in Table 11 below can be used to calculate risk scores or to make risk determinations, including calculating the patient falls score, pressure injury score, and sepsis score discussed herein (some of the data elements being risk factors including the same risk factors as listed in Table 1):

TABLE 11

| Number | Data Element |
|---|---|
| 1 | BED DATA |
| 2 | Connection State |
| 3 | Connectivity Protocol |
| 4 | LastKnownBedConnect |
| 5 | BedPosition (height) |
| 6 | HeadRailsPosition |
| 7 | FootRailsPosition |
| 8 | HeadAngleInDegrees |
| 9 | HeadAngleAlarmMode |
| 10 | HeadAngleAlarmAudibleMode |
| 11 | HeadAngleAlarmStatus |
| 12 | NurseCallIndicatorState |
| 13 | NurseAnswerIndicatorState |
| 14 | NaviCareAlertsIndicatorState |
| 15 | BedCleanedIndicatorState |
| 16 | BedOnlineWithServerIndicatorState |
| 17 | HeadAngleMotorLockoutState |
| 18 | KneeAngleMotorLockoutState |
| 19 | BedHeightMotorLockoutState |
| 20 | TiltAngleMotorLockoutState |
| 21 | AllMotorsLockoutState |
| 22 | BedModelName |
| 23 | SidecomSerialNumber |
| 24 | SidecomSoftwareRevision |
| 25 | PatientEnvironmentLastCommand |
| 26 | PatientHistoryLastCommand |
| 27 | ACPowerStatus |
| 28 | BatteryPowerStatus |
| 29 | PatientPositioningAlarmMode |
| 30 | PatientPositioningAlarmStatus |
| 31 | PatientMovementMagnitude |
| 32 | PatientMovementDirection |
| 33 | SafeViewMode |
| 34 | SafeViewIndicatorStatus |
| 35 | ScaleLastCommand |
| 36 | CapturePatientWeightInKg |
| 37 | CapturedPatientWeightInLbs |
| 38 | LivePatientWeightInKg |
| 39 | LivePatientWeightInLbs |
| 40 | ServiceRequiredStatus |
| 41 | SurfaceMode |
| 42 | NurseCallSwitchState |
| 43 | NaviCareAlertsSwitchState |
| 44 | CPRSwitchState |
| 45 | BedCleanedSwitchState |
| 46 | RotationTherapyStatus |
| 47 | PercussionTherapyStatus |
| 48 | VibrationTherapyStatus |
| 49 | BrakeSwitchState |
| 50 | BedServiceCode |
| 51 | FrameSerialNumber |
| 52 | PatientDetected |
| 53 | SafeViewLoLo |
| 54 | SafeViewSideRail |
| 55 | SafeViewPatientPosition |
| 56 | HeadAngleLimitEnabled |
| 57 | PatientPositionChairMode |
| 58 | SafeViewIncontinence |
| 59 | IncontinenceDetected |
| 60 | DeteriorationDetected |
| 61 | MacAddress |
| 62 | IPAddress |
| 63 | SignalStrengthInDBm |
| 64 | Load cell data |
| 65 | Log files |
| 66 | VITALS (EWS inputs) |
| 67 | Respiratory rate |
| 68 | Heart Rate |
| 69 | Pulse Rate |
| 70 | SpO2/SaO2 |
| 71 | SBP |
| 72 | DBP |
| 73 | MAP |
| 74 | Temperature |
| 75 | PaO2/FiO2 |
| 76 | EtCO2 |
| 77 | Vitals Trend |
| 78 | Pain Score |
| 79 | Urine Output |
| 80 | LABS |
| 81 | Abnormal Labs |
| 82 | POC Blood Glucose |
| 83 | New Lab Results Received |
| 84 | Complete Blood Count (CBC) (panel) |
| 85 | White Blood Cell Count |
| 86 | Red Blood Cell Count |
| 87 | Hemoglobin (Hgb) |
| 88 | Hematocrit (Hct) or Packed Cell Volume (PCV) |
| 89 | Mean Corpuscular Volume (MCV) |
| 90 | Platelet Count (Plt) |
| 91 | Mean Corpuscular Hemoglobin(MCH) |
| 92 | Mean Corpuscular Hemoglobin Concentration (MCHC) |
| 93 | Red Cell Distribution Width (RDW) |
| 94 | Platelet Distribution Width (PDW) |
| 95 | Mean Platelet Volume (MPV) |
| 96 | Reticulocyte Count |
| 97 | Basic Metabolic Panel (BMP) |
| 98 | Glucose |
| 99 | Calcium |
| 100 | Sodium |
| 101 | Potassium |
| 102 | Carbon Dioxide (aka Bicarbonate) |
| 103 | Chloride |
| 104 | Blood Urea Nitrogen (BUN) |
| 105 | Creatinine |
| 106 | When Next Labs Due |
| 107 | Normal Lab Results Ranges |
| 108 | International Normalized Ratio (INR) |
| 109 | Blood Gases |
| 110 | Partial Thromboplastin Time (PTT) |
| 111 | Activated Partial Thromboplastin Time (aPTT) |
| 112 | Prothrombin Time (PT) |
| 113 | Arterial Blood Gas (panel) |
| 114 | pH |
| 115 | PaO2 |
| 116 | PaCO2 |
| 117 | SaO2 |
| 118 | Oxygen Content |
| 119 | Bicarbonate |
| 120 | Base Excess (BE) |
| 121 | Blood Glucose |
| 122 | Urinalysis (panel) |
| 123 | pH |
| 124 | Concentration (aka Specific Gravity) |
| 125 | Protein |
| 126 | Glucose |
| 127 | Ketones |
| 128 | Bilirubin |
| 129 | Evidence of Injection |
| 130 | Evidence of Blood |
| 131 | White Blood Cell Count |
| 132 | Red Blood Cell Count |
| 133 | Bacteria and/or yeasts |
| 134 | Casts |
| 135 | Crystals |
| 136 | Lactate |
| 137 | Platelets |
| 138 | Creatinine |
| 139 | Suspected or present Infection |
| 140 | WBC Count |
| 141 | Neutrophils/Bands |
| 142 | Bilirubin |
| 143 | INTERVENTIONS |
| 144 | Supplemental O2 |
| 145 | Mechanical ventilation |
| 146 | Quarter-hourly nebulizers |
| 147 | PATIENT STATUS |

TABLE 11-continued

| Number | Data Element |
|---|---|
| 148 | Allergies |
| 149 | Do Not Resuscitate (DNR) |
| 150 | NPO (Nothing by the mouth) |
| 151 | Precautions (isolation, violent, elopement, psych) |
| 152 | General (language, blind/deaf, amputee, pacemaker, DVT, cardiac abnormalities, etc) |
| 153 | Dietary status |
| 154 | Capillary Refill Time |
| 155 | Color (pink/pale/gray/gray and mottled) |
| 156 | Respiratory flow rate |
| 157 | Intercostal retractions |
| 158 | Hypotension/Pressor Use |
| 159 | Ambulatory aid (none/bedrest/nurse assist/crutches/cane/walker/furniture |
| 160 | Gait (normal/bedrest/immobile/weak/unsteady/impaired) |
| 161 | Visual impairment affecting everyday function |
| 162 | Vertigo/orthostatic hypotension/weakness |
| 163 | Transfer from bed to chair (unable/needs major help/needs minor help/independent) |
| 164 | Rising from a seated position (in single movement/pushes up in one attempt/successful after multiple attempts/requires assistance) |
| 165 | Mobility (immobile/independent with wheelchair/walking aid or person assisting/independent) |
| 166 | IV/Heparin lock |
| 167 | Incontinence |
| 168 | Urgency or frequency of urination |
| 169 | Urinary catheter/ostomy |
| 170 | Elimination with assistance |
| 171 | Nocturia |
| 172 | Sedated procedure |
| 173 | Tethered patient care equipment (e.g. IV, chest tube, indwelling catheter, SCDs, etc) |
| 174 | Response to Surgery/Sedation/Anesthesia (within 24 hours/within 48 hours/more than 48 hours or none) |
| 175 | Persistent vomiting after surgery |
| 176 | Consciousness (AVPU) |
| 177 | Consciousness (GCS) |
| 178 | Mental status (oriented to own ability/forgets limitations/fully alert/agitation or anxiety/intermittently confused, confusion or disorientation) |
| 179 | Cognition (altered awareness of physical environment/impulsive/forgets limitations) |
| 180 | Behavior (playing or appropriate/sleeping/irritable/lethargic or confused or reduced pain response) |
| 181 | DEMOGRAPHICS |
| 182 | Current chronological age (observable entity) |
| 183 | Age (qualifier value) |
| 184 | Aging (finding) |
| 185 | Premature aging (finding) |
| 186 | Old-age (finding) |
| 187 | Senile debility (finding) |
| 188 | Senility (finding) |
| 189 | Extreme old age (over 100 years) (finding) |
| 190 | Senile exhaustion (finding) |
| 191 | Senile asthenia (finding) |
| 192 | Old age (qualifier value) |
| 193 | Entire life (qualifier value) |
| 194 | Old-age (finding) |
| 195 | Senile debility (finding) |
| 196 | Senility (finding) |
| 197 | Extreme old age (over 100 years) (finding) |
| 198 | Senile exhaustion (finding) |
| 199 | Senile asthenia (finding) |
| 200 | Gender (observable entity) |
| 201 | MEDICATIONS |
| 202 | Current Medications |
| 203 | Aminoglycoside (substance) |
| 204 | Analgesic (substance) |
| 205 | Medicinal product acting as analgesic agent (product) |
| 206 | Substance with opioid receptor agonist mechanism of action (substance) |
| 207 | Antiarrhythmic agent (substance) |
| 208 | Medicinal product acting as antiarrhythmic agent (product) |
| 209 | Quaternary ammonium compound with anticholinergic mechanism of action (substance) |
| 210 | Vasodilator (substance) |
| 211 | Hypotensive agent (substance) |
| 212 | Hypotensive agent (product) |
| 213 | Anti-psychotic agent (substance) |
| 214 | Medicinal product acting as antipsychotic agent (product) |
| 215 | Diuretic (substance) |
| 216 | Medicinal product acting as diuretic (product) |
| 217 | Loop diuretic (substance) |
| 218 | Loop diuretic overdose (disorder) |
| 219 | Psychoactive substance (substance) |
| 220 | Antidepressant (substance) |
| 221 | Medicinal product acting as antidepressant agent (product) |
| 222 | Anti-psychotic agent (substance) |
| 223 | Medicinal product acting as antipsychotic agent (product) |
| 224 | Benzodiazepine (substance) |
| 225 | Psychoactive substance (substance) |
| 226 | Nicotine cyclodextrin complex (substance) |
| 227 | Cannabinoid (substance) |
| 228 | Psychotropic agent (substance) |
| 229 | Nicotine polacrilex (substance) |
| 230 | Nicotine (substance) |
| 231 | Trichloroethylene (substance) |
| 232 | Central depressant (substance) |
| 233 | Nicotine resin complex (substance) |
| 234 | Medication Dosage |
| 235 | When Meds are Due |
| 236 | When Meds Last Received |
| 237 | Medication Route |
| 238 | Medication Form (liquid, pill, etc) |
| 239 | PRN (as needed medications) |
| 240 | Drug Class Type (beta blockers, barbiturates, etc) |
| 241 | DIAGNOSES/COMORBIDITIES |
| 242 | Anemia (disorder) |
| 243 | Anemia due to metabolic disorder (disorder) |
| 244 | Central nervous system calcification, deafness, tubular acidosis, anemia syndrome (disorder) |
| 245 | Fetal anemia (disorder) |
| 246 | Anemia caused by substance (disorder) |
| 247 | Anemia associated with acquired immunodeficiency syndrome (disorder) |
| 248 | Anemia due to blood loss (disorder) |
| 249 | Refractory anemia with excess blasts (disorder) |
| 250 | Sports anemia (disorder) |
| 251 | Perinatal anemia (disorder) |
| 252 | Anemia due to intrinsic red cell abnormality (disorder) |
| 253 | Normocytic anemia (disorder) |
| 254 | Deficiency anemias (disorder) |
| 255 | Neonatal anemia (disorder) |
| 256 | Microcytic anemia (disorder) |
| 257 | Anemia of renal disease (disorder) |
| 258 | Anemia of chronic disorder (disorder) |
| 259 | Dilutional anemia (disorder) |
| 260 | Chronic anemia (disorder) |
| 261 | Anemia in neoplastic disease (disorder) |
| 262 | Anemia due to disorders of nucleotide metabolism (disorder) |
| 263 | On examination - profoundly anemic (disorder) |
| 264 | On examination - clinically anemic (disorder) |
| 265 | On examination - equivocally anemic (disorder) |
| 266 | Regenerative anemia (disorder) |
| 267 | Anemia caused by physical agent (disorder) |
| 268 | Refractory anemia with excess blasts in transformation (disorder) |
| 269 | Myelodysplastic syndrome: Refractory anemia, without ringed sideroblasts, without excess blasts (disorder) |
| 270 | Anemia related to disturbed deoxyribonucleic acid synthesis (disorder) |
| 271 | Aregenerative anemia (disorder) |
| 272 | Non megaloblastic anemia due to alcoholism (disorder) |
| 273 | Macrocytic anemia (disorder) |
| 274 | Anemia due to unknown mechanism (disorder) |
| 275 | Nutritional anemia (disorder) |
| 276 | Congenital anemia (disorder) |
| 277 | Hemolytic anemia (disorder) |
| 278 | Anemia due to decreased red cell production (disorder) |
| 279 | Normocytic normochromic anemia (disorder) |
| 280 | Anemia in mother complicating pregnancy, childbirth AND/OR puerperium (disorder) |
| 281 | Anemia due to multiple mechanisms (disorder) |
| 282 | Normocytic hypochromic anemia (disorder) |
| 283 | Sideroblastic anemia (disorder) |

TABLE 11-continued

| Number | Data Element |
|---|---|
| 284 | Anemia due to disturbance of proliferation AND/OR differentiation of erythroid precursor cells (disorder) |
| 285 | Anemia of endocrine disorder (disorder) |
| 286 | Acquired Heinz body anemia (disorder) |
| 287 | Anemia due to disturbance of hemoglobin synthesis (disorder) |
| 288 | Relative anemia (disorder) |
| 289 | Myelophthisic anemia (disorder) |
| 290 | Cardiac arrhythmia (disorder) |
| 291 | Cardiac arrhythmia in mother complicating childbirth (disorder) |
| 292 | Arrhythmia during surgery (disorder) |
| 293 | Arrhythmia due to and following acute myocardial infarction (disorder) |
| 294 | Heart-hand syndrome type 2 (disorder) |
| 295 | Cardiac channelopathy (disorder) |
| 296 | Cardiac arrhythmia associated with genetic disorder (disorder) |
| 297 | Arrhythmia due to vegetation of infective endocarditis (disorder) |
| 298 | Bundle branch reentrant ventricular tachycardia (disorder) |
| 299 | Bradyarrhythmia (disorder) |
| 300 | Cardiac arrest (disorder) |
| 301 | Neonatal dysrhythmia (disorder) |
| 302 | Fetal dysrhythmia (disorder) |
| 303 | Atrial escape complex (disorder) |
| 304 | Ventricular escape complex (disorder) |
| 305 | Aberrantly conducted complex (disorder) |
| 306 | Aberrant premature complexes (disorder) |
| 307 | Pacemaker twiddler's syndrome (disorder) |
| 308 | Supraventricular arrhythmia (disorder) |
| 309 | Nodal rhythm disorder (disorder) |
| 310 | Atrioventricular dissociation (disorder) |
| 311 | Tic-tac rhythm (disorder) |
| 312 | Conduction disorder of the heart (disorder) |
| 313 | Ventricular arrhythmia (disorder) |
| 314 | Fibrillation (disorder) |
| 315 | Ectopic beats (disorder) |
| 316 | Premature beats (disorder) |
| 317 | Ectopic rhythm (disorder) |
| 318 | Holt-Oram syndrome (disorder) |
| 319 | Anomalous atrioventricular excitation (disorder) |
| 320 | Accelerated atrioventricular conduction (disorder) |
| 321 | Tachyarrhythmia (disorder) |
| 322 | Withdrawal arrhythmia (disorder) |
| 323 | Carotid sinus syncope (disorder) |
| 324 | Chronic obstructive lung disease (disorder) |
| 325 | Asthma-chronic obstructive pulmonary disease overlap syndrome (disorder) |
| 326 | Chronic obstructive lung disease co-occurrent with acute bronchitis (disorder) |
| 327 | Severe chronic obstructive pulmonary disease (disorder) |
| 328 | Moderate chronic obstructive pulmonary disease (disorder) |
| 329 | Mild chronic obstructive pulmonary disease (disorder) |
| 330 | Chronic obstructive pulmonary disease with acute lower respiratory infection (disorder) |
| 331 | Acute exacerbation of chronic obstructive airways disease (disorder) |
| 332 | End stage chronic obstructive airways disease (disorder) |
| 333 | Pulmonary emphysema (disorder) |
| 334 | Chronic obliterative bronchiolitis (disorder) |
| 335 | Dehydration (disorder) |
| 336 | Dehydration due to radiation (disorder) |
| 337 | Mild dehydration (disorder) |
| 338 | Moderate dehydration (disorder) |
| 339 | Dehydration following exertion (disorder) |
| 340 | Severe dehydration (disorder) |
| 341 | Hypernatremic dehydration (disorder) |
| 342 | Deprivation of water (disorder) |
| 343 | Isonatremic dehydration (disorder) |
| 344 | On examination - dehydrated (disorder) |
| 345 | Neonatal dehydration (disorder) |
| 346 | Pneumonia (disorder) |
| 347 | Pneumonia caused by *Bordetella parapertussis* (disorder) |
| 348 | Chronic pneumonia (disorder) |
| 349 | Idiopathic eosinophilic pneumonia (disorder) |
| 350 | Recurrent pneumonia (disorder) |
| 351 | Cavitary pneumonia (disorder) |
| 352 | Ventilator-acquired pneumonia (disorder) |
| 353 | Aspiration pneumonia (disorder) |
| 354 | Pneumonia associated with acquired immunodeficiency syndrome (disorder) |
| 355 | Bilateral pneumonia (disorder) |
| 356 | Bronchopneumonia (disorder) |
| 357 | Community acquired pneumonia (disorder) |
| 358 | Postobstructive pneumonia (disorder) |
| 359 | Postoperative pneumonia (disorder) |
| 360 | Infective pneumonia (disorder) |
| 361 | Lobar pneumonia (disorder) |
| 362 | Neonatal pneumonia (disorder) |
| 363 | Hemorrhagic pneumonia (disorder) |
| 364 | Abscess of lung with pneumonia (disorder) |
| 365 | Pneumonia and influenza (disorder) |
| 366 | Post measles pneumonia (disorder) |
| 367 | Confluent pneumonia (disorder) |
| 368 | Focal pneumonia (disorder) |
| 369 | Non-infectious pneumonia (disorder) |
| 370 | Hypostatic pneumonia (disorder) |
| 371 | Congenital pneumonia (disorder) |
| 372 | Granulomatous pneumonia (disorder) |
| 373 | Organized pneumonia (disorder) |
| 374 | Interstitial pneumonia (disorder) |
| 375 | Unresolved pneumonia (disorder) |
| 376 | Catarrhal pneumonia (disorder) |
| 377 | Gangrenous pneumonia (disorder) |
| 378 | Sepsis (disorder) |
| 379 | Sepsis due to incomplete miscarriage (disorder) |
| 380 | Sepsis due to ectopic pregnancy (disorder) |
| 381 | Sepsis without acute organ dysfunction (disorder) |
| 382 | Line sepsis associated with dialysis catheter (disorder) |
| 383 | Sepsis caused by virus (disorder) |
| 384 | Sepsis due to urinary tract infection (disorder) |
| 385 | Perinatal sepsis (disorder) |
| 386 | Sepsis due to oral infection (disorder) |
| 387 | Sepsis with cutaneous manifestations (disorder) |
| 388 | Sepsis caused by fungus (disorder) |
| 389 | Sepsis associated with acquired immunodeficiency syndrome (disorder) |
| 390 | Sepsis in asplenic subject (disorder) |
| 391 | Postoperative sepsis (disorder) |
| 392 | Induced termination of pregnancy complicated by sepsis (disorder) |
| 393 | Sepsis caused by herpes simplex (disorder) |
| 394 | Neutropenic sepsis (disorder) |
| 395 | Transient respiratory distress with sepsis (disorder) |
| 396 | Umbilical sepsis (disorder) |
| 397 | Sepsis of the newborn (disorder) |
| 398 | Miscarriage with sepsis (disorder) |
| 399 | Sepsis following infusion, injection, transfusion AND/OR vaccination (disorder) |
| 400 | Sepsis following molar AND/OR ectopic pregnancy (disorder) |
| 401 | Pyemia (disorder) |
| 402 | Tracheostomy sepsis (disorder) |
| 403 | Failed attempted abortion with sepsis (disorder) |
| 404 | Acute tubulointerstitial nephritis associated with systemic infection (disorder) |
| 405 | Bacterial sepsis (disorder) |
| 406 | Brazilian purpuric fever (disorder) |
| 407 | Gas gangrene septicemia (disorder) |
| 408 | Puerperal sepsis (disorder) |
| 409 | Intrauterine sepsis of fetus (disorder) |
| 410 | Diabetes mellitus (disorder) |
| 411 | Atypical diabetes mellitus (disorder) |
| 412 | Diabetes mellitus due to pancreatic injury (disorder) |
| 413 | Erectile dysfunction co-occurrent and due to diabetes mellitus (disorder) |
| 414 | Acute complication co-occurrent and due to diabetes mellitus (disorder) |
| 415 | Metabolic acidosis co-occurrent and due to diabetes mellitus (disorder) |
| 416 | Lactic acidosis co-occurrent and due to diabetes mellitus (disorder) |
| 417 | Alaninuria, microcephaly, dwarfism, enamel hypoplasia, diabetes mellitus syndrome (disorder) |
| 418 | Diabetic mastopathy (disorder) |

TABLE 11-continued

| Number | Data Element |
|---|---|
| 419 | Pancreatic hypoplasia, diabetes mellitus, congenital heart disease syndrome (disorder) |
| 420 | Gingival disease co-occurrent with diabetes mellitus (disorder) |
| 421 | Diabetes mellitus in remission (disorder) |
| 422 | Diabetes mellitus due to genetic defect in insulin action (disorder) |
| 423 | Diabetes mellitus due to genetic defect in beta cell function (disorder) |
| 424 | Disorder of nervous system co-occurrent and due to diabetes mellitus (disorder) |
| 425 | Peripheral vascular disorder co-occurrent and due to diabetes mellitus (disorder) |
| 426 | Disorder of soft tissue co-occurrent and due to diabetes mellitus (disorder) |
| 427 | Diabetes mellitus during pregnancy, childbirth and the puerperium (disorder) |
| 428 | Disorder of kidney co-occurrent and due to diabetes mellitus (disorder) |
| 429 | Houssay's syndrome (disorder) |
| 430 | Diabetes mellitus without complication (disorder) |
| 431 | Diabetes mellitus type 1 (disorder) |
| 432 | Diabetes mellitus type 2 (disorder) |
| 433 | Disorder of eye co-occurrent and due to diabetes mellitus (disorder) |
| 434 | Secondary diabetes mellitus (disorder) |
| 435 | Disorder of thyroid gland (disorder) |
| 436 | Nodular thyroid disease (disorder) |
| 437 | Thyrocerebrorenal syndrome (disorder) |
| 438 | Hypoplasia of thyroid (disorder) |
| 439 | Thyroid infection (disorder) |
| 440 | Perinatal thyroid disorder (disorder) |
| 441 | Thyroid dysfunction (disorder) |
| 442 | Injury of thyroid gland (disorder) |
| 443 | Iodine deficiency syndrome (disorder) |
| 444 | Thyroid hormone binding abnormality (disorder) |
| 445 | Sick-euthyroid syndrome (disorder) |
| 446 | Thyroid atrophy (disorder) |
| 447 | Disorder of thyrocalcitonin secretion (disorder) |
| 448 | Neoplasm of thyroid gland (disorder) |
| 449 | Complex thyroid endocrine disorder (disorder) |
| 450 | Abscess of thyroid (disorder) |
| 451 | Thyroiditis (disorder) |
| 452 | Cyst of thyroid (disorder) |
| 453 | Transient decreased production of thyroid hormone (disorder) |
| 454 | Multiple endocrine neoplasia, type 3 (disorder) |
| 455 | Thyroid disease in mother complicating pregnancy, childbirth AND/OR puerperium (disorder) |
| 456 | Hypothyroidism (disorder) |
| 457 | Inherited disorder of thyroid metabolism (disorder) |
| 458 | Hyperthyroidism (disorder) |
| 459 | Congenital anomaly of the thyroid gland (disorder) |
| 460 | Ascher's syndrome (disorder) |
| 461 | Hurthle cell metaplasia of thyroid gland (disorder) |
| 462 | Infarction of thyroid (disorder) |
| 463 | Goiter (disorder) |
| 464 | Hemorrhage of thyroid (disorder) |
| 465 | Hypersecretion of calcitonin (disorder) |
| 466 | Hypoglycemia (disorder) |
| 467 | Post gastrointestinal tract surgery hypoglycemia (disorder) |
| 468 | Neonatal hypoglycemia (disorder) |
| 469 | Diabetic hyperosmolar non-ketotic state (disorder) |
| 470 | Hyperosmolar hyperglycemic coma due to diabetes mellitus without ketoacidosis (disorder) |
| 471 | Hyperosmolar non-ketotic state in type 2 diabetes mellitus (disorder) |
| 472 | Orthostatic hypotension (disorder) |
| 473 | Postural hypotension following exercise (disorder) |
| 474 | Orthostatic hypotension co-occurrent and due to Parkinson's disease (disorder) |
| 475 | Postural orthostatic tachycardia syndrome (disorder) |
| 476 | Sympathotonic orthostatic hypotension (disorder) |
| 477 | Chronic orthostatic hypotension (disorder) |
| 478 | Hypoadrenergic postural hypotension (disorder) |
| 479 | Hyperadrenergic postural hypotension (disorder) |
| 480 | Congestive heart failure due to valvular disease (disorder) |
| 481 | Delirium (disorder) |
| 482 | Delirium following surgical procedure (disorder) |
| 483 | Delirium co-occurrent with dementia (disorder) |
| 484 | Delirium due to multiple etiological factors (disorder) |
| 485 | Delirium caused by substance or medication (disorder) |
| 486 | Delirium in remission (disorder) |
| 487 | Chronic confusional state (disorder) |
| 488 | Psychosis associated with intensive care (disorder) |
| 489 | Delirium of mixed origin (disorder) |
| 490 | Toxic confusional state (disorder) |
| 491 | Subacute delirium (disorder) |
| 492 | Acute confusional state, of cerebrovascular origin (disorder) |
| 493 | Acute confusional state, of metabolic origin (disorder) |
| 494 | Acute confusional state, of endocrine origin (disorder) |
| 495 | Acute confusional state, of infective origin (disorder) |
| 496 | Acute confusional state, post-traumatic (disorder) |
| 497 | Drug-induced delirium (disorder) |
| 498 | Acute non-psychotic brain syndrome (disorder) |
| 499 | Postseizure delirium (disorder) |
| 500 | Multi-infarct dementia with delirium (disorder) |
| 501 | Dementia (disorder) |
| 502 | Primary degenerative dementia (disorder) |
| 503 | Dementia with behavioral disturbance (disorder) |
| 504 | Protein kinase cAMP-dependent type I regulatory subunit beta-related neurodegenerative dementia with intermediate filaments (disorder) |
| 505 | Subcortical dementia (disorder) |
| 506 | Dementia following injury caused by exposure to ionizing radiation (disorder) |
| 507 | Dementia caused by heavy metal exposure (disorder) |
| 508 | Delirium co-occurrent with dementia (disorder) |
| 509 | Rapidly progressive dementia (disorder) |
| 510 | Dementia caused by toxin (disorder) |
| 511 | Parkinsonism co-occurrent with dementia of Guadeloupe (disorder) |
| 512 | Dementia co-occurrent with human immunodeficiency virus infection (disorder) |
| 513 | Dementia in remission (disorder) |
| 514 | Dementia of frontal lobe type (disorder) |
| 515 | Senile and presenile organic psychotic conditions (disorder) |
| 516 | Patchy dementia (disorder) |
| 517 | Semantic dementia (disorder) |
| 518 | Dementia associated with another disease (disorder) |
| 519 | Drug-induced dementia (disorder) |
| 520 | Parkinson-dementia complex of Guam (disorder) |
| 521 | General paresis - neurosyphilis (disorder) |
| 522 | Alzheimer's disease (disorder) |
| 523 | Senile dementia (disorder) |
| 524 | Presenile dementia (disorder) |
| 525 | Dialysis dementia (disorder) |
| 526 | Cerebrovascular accident (disorder) |
| 527 | Cerebellar stroke (disorder) |
| 528 | Cerebrovascular accident due to stenosis of left carotid artery (disorder) |
| 529 | Cerebrovascular accident due to stenosis of right carotid artery (disorder) |
| 530 | Cerebrovascular accident due to occlusion of right cerebellar artery (disorder) |
| 531 | Cerebrovascular accident due to occlusion of left cerebellar artery (disorder) |
| 532 | Cerebrovascular accident due to occlusion of left carotid artery (disorder) |
| 533 | Cerebrovascular accident due to occlusion of right pontine artery (disorder) |
| 534 | Cerebrovascular accident due to occlusion of left pontine artery (disorder) |
| 535 | Cerebrovascular accident due to occlusion of right carotid artery (disorder) |
| 536 | Cerebrovascular accident due to occlusion of left vertebral artery (disorder) |
| 537 | Cerebrovascular accident due to occlusion of right vertebral artery (disorder) |
| 538 | Cerebrovascular accident due to stenosis of left vertebral artery (disorder) |
| 539 | Cerebrovascular accident due to stenosis of right vertebral artery (disorder) |
| 540 | Occlusion of cerebral artery with stroke (disorder) |
| 541 | Stroke co-occurrent with migraine (disorder) |
| 542 | Silent cerebral infarct (disorder) |
| 543 | Cerebrovascular accident during surgery (disorder) |

TABLE 11-continued

| Number | Data Element |
|---|---|
| 544 | Ischemic stroke (disorder) |
| 545 | Infarction of basal ganglia (disorder) |
| 546 | Neonatal stroke (disorder) |
| 547 | Embolic stroke (disorder) |
| 548 | Thrombotic stroke (disorder) |
| 549 | Extension of cerebrovascular accident (disorder) |
| 550 | Stroke in the puerperium (disorder) |
| 551 | Ruptured cerebral aneurysm (disorder) |
| 552 | Stroke of uncertain pathology (disorder) |
| 553 | Cerebrovascular accident due to occlusion of cerebral artery (disorder) |
| 554 | Right sided cerebral hemisphere cerebrovascular accident (disorder) |
| 555 | Left sided cerebral hemisphere cerebrovascular accident (disorder) |
| 556 | Brainstem stroke syndrome (disorder) |
| 557 | Paralytic stroke (disorder) |
| 558 | Nonparalytic stroke (disorder) |
| 559 | Intracranial sinus thrombosis, embolism AND/OR inflammation (disorder) |
| 560 | Progressing stroke (disorder) |
| 561 | Juvenile myopathy, encephalopathy, lactic acidosis AND stroke (disorder) |
| 562 | Completed stroke (disorder) |
| 563 | Anterior choroidal artery syndrome (disorder) |
| 564 | Arthritis (disorder) |
| 565 | Arthritis of right sternoclavicular joint (disorder) |
| 566 | Arthritis of left sternoclavicular joint (disorder) |
| 567 | Primary chronic gout without tophus of shoulder (disorder) |
| 568 | Gout of shoulder caused by drug (disorder) |
| 569 | Transient arthritis (disorder) |
| 570 | Arthritis of wrist (disorder) |
| 571 | Interstitial granulomatous dermatitis with arthritis (disorder) |
| 572 | Immune dysregulation, inflammatory bowel disease, arthritis, recurrent infection syndrome (disorder) |
| 573 | Monoarthritis (disorder) |
| 574 | Inflammation of joint of hand (disorder) |
| 575 | Inflammation of joint of shoulder region (disorder) |
| 576 | Arthritis of elbow (disorder) |
| 577 | Arthritis of acromioclavicular joint (disorder) |
| 578 | Inflammatory polyarthropathy (disorder) |
| 579 | Undifferentiated inflammatory arthritis (disorder) |
| 580 | Synovitis (disorder) |
| 581 | Seronegative arthritis (disorder) |
| 582 | Infective arthritis (disorder) |
| 583 | Suppurative arthritis (disorder) |
| 584 | Arthritis of spine (disorder) |
| 585 | Cricoarytenoid joint arthritis (disorder) |
| 586 | Lower limb joint arthritis (disorder) |
| 587 | Small and large joint arthritis (disorder) |
| 588 | Large joint arthritis (disorder) |
| 589 | Small joint arthritis (disorder) |
| 590 | Asymmetrical arthritis (disorder) |
| 591 | Symmetrical arthritis (disorder) |
| 592 | Cholesterol-related arthritis and periarthritis (disorder) |
| 593 | Oxalate-related arthritis and periarthritis (disorder) |
| 594 | Idiopathic pyrophosphate arthritis (disorder) |
| 595 | Chronic infantile neurological, cutaneous and articular syndrome (disorder) |
| 596 | Arthritis following intestinal bypass (disorder) |
| 597 | Post-immunization arthritis (disorder) |
| 598 | Palindromic rheumatism of the pelvic region and thigh (disorder) |
| 599 | Palindromic rheumatism of the shoulder region (disorder) |
| 600 | Generalized arthritis (disorder) |
| 601 | Erosive osteoarthrosis (disorder) |
| 602 | Arthropathy in Crohn's disease (disorder) |
| 603 | Systemic lupus erythematosus arthritis (disorder) |
| 604 | Arthritis of temporomandibular joint (disorder) |
| 605 | Climacteric arthritis (disorder) |
| 606 | Osteochondritis (disorder) |
| 607 | Rheumatoid arthritis (disorder) |
| 608 | Subacute arthritis (disorder) |
| 609 | Chronic arthritis (disorder) |
| 610 | Acute arthritis (disorder) |
| 611 | Arthritis associated with another disorder (disorder) |
| 612 | Deformity of foot (finding) |
| 613 | Acquired overriding toes of left foot (disorder) |
| 614 | Acquired overriding toes of right foot (disorder) |
| 615 | Deformity of foot due to rheumatoid arthritis (finding) |
| 616 | Putter foot (finding) |
| 617 | Pronation deformity of the foot (finding) |
| 618 | Supination deformity of the foot (finding) |
| 619 | Pronated forefoot (finding) |
| 620 | Supinated forefoot (finding) |
| 621 | Adductus deformity of foot (finding) |
| 622 | Plantarflexion deformity of foot (finding) |
| 623 | Abduction deformity of the foot (finding) |
| 624 | Acquired curly toe (disorder) |
| 625 | Dorsiflexion deformity of foot (finding) |
| 626 | Acquired valgus heel (disorder) |
| 627 | Overriding fifth toe (disorder) |
| 628 | Overriding toe (disorder) |
| 629 | Muscle weakness (finding) |
| 630 | Muscle weakness of limb (finding) |
| 631 | Spastic paresis (finding) |
| 632 | Hand muscle weakness (finding) |
| 633 | Pyramidal type muscle weakness (finding) |
| 634 | Distal muscle weakness (finding) |
| 635 | Proximal muscle weakness (finding) |
| 636 | Truncal muscle weakness (finding) |
| 637 | Weakness of sternomastoid (finding) |
| 638 | Weakness of jaw muscles (finding) |
| 639 | On examination - muscle power reduced (finding) |
| 640 | On examination - paresis (weakness) (finding) |
| 641 | Weakness present (finding) |
| 642 | Pseudoparalysis (finding) |
| 643 | Palatal paresis (finding) |
| 644 | Laryngeal paresis (finding) |
| 645 | Pharyngeal paresis (finding) |
| 646 | Bilateral paresis (finding) |
| 647 | Subjective muscle weakness (finding) |
| 648 | Paresis of lower extremity (finding) |
| 649 | Weakness of face muscles (finding) |
| 650 | Diaphragmatic paresis (finding) |
| 651 | Neurological muscle weakness (finding) |
| 652 | Spinal paraparesis (finding) |
| 653 | Spinal hemiparesis (finding) |
| 654 | Inherited spastic paresis (disorder) |
| 655 | Cerebellar degeneration (disorder) |
| 656 | Acute cerebellar syndrome (disorder) |
| 657 | Secondary cerebellar degeneration (disorder) |
| 658 | Cerebellar deficiency syndrome (disorder) |
| 659 | Posthemiplegic ataxia (disorder) |
| 660 | Primary progressive cerebellar degeneration (disorder) |
| 661 | Juvenile cerebellar degeneration AND myoclonus (disorder) |
| 662 | Olivopontocerebellar degeneration (disorder) |
| 663 | Paramyoclonus multiplex (disorder) |
| 664 | Bailey-Cushing syndrome (disorder) |
| 665 | Jervis' syndrome (disorder) |
| 666 | Roussy-Lévy syndrome (disorder) |
| 667 | Corticostriatal-spinal degeneration (disorder) |
| 668 | Hereditary cerebellar degeneration (disorder) |
| 669 | Primary cerebellar degeneration (disorder) |
| 670 | Sporadic cerebellar degeneration (disorder) |
| 671 | Friedreich's ataxia (disorder) |
| 672 | Athetosis with spastic paraplegia (disorder) |
| 673 | Cervical myelopathy (disorder) |
| 674 | Myelopathy co-occurrent and due to spinal stenosis of cervical region (disorder) |
| 675 | Parkinsonism (disorder) |
| 676 | X-linked parkinsonism with spasticity syndrome (disorder) |
| 677 | Hemiparkinsonism hemiatrophy syndrome (disorder) |
| 678 | Autosomal dominant striatal neurodegeneration (disorder) |
| 679 | Functional parkinsonism (disorder) |
| 680 | Parkinsonism due to mass lesion of brain (disorder) |
| 681 | Infection causing parkinsonism (disorder) |
| 682 | Kufor Rakeb syndrome (disorder) |
| 683 | Atypical Parkinsonism (disorder) |
| 684 | Infantile dystonia parkinsonism (disorder) |
| 685 | Adult-onset dystonia parkinsonism (disorder) |
| 686 | Psychosis co-occurrent and due to Parkinson's disease (disorder) |
| 687 | Parkinsonism co-occurrent with dementia of Guadeloupe (disorder) |
| 688 | Rapid onset dystonia parkinsonism (disorder) |

TABLE 11-continued

| Number | Data Element |
|---|---|
| 689 | Perry syndrome (disorder) |
| 690 | X-linked dystonia parkinsonism (disorder) |
| 691 | On - off phenomenon (disorder) |
| 692 | Symptomatic parkinsonism (disorder) |
| 693 | Secondary parkinsonism (disorder) |
| 694 | Parkinsonian syndrome associated with idiopathic orthostatic hypotension (disorder) |
| 695 | Parkinson-dementia complex of Guam (disorder) |
| 696 | Parkinson's disease (disorder) |
| 697 | Striatonigral degeneration (disorder) |
| 698 | Peripheral nerve disease (disorder) |
| 699 | Paraneoplastic peripheral neuropathy (disorder) |
| 700 | Primary CD59 deficiency (disorder) |
| 701 | Peripheral neuropathy due to and following chemotherapy (disorder) |
| 702 | Morvan syndrome (disorder) |
| 703 | Acquired hypoganglionosis of large intestine (disorder) |
| 704 | Deafness, small bowel diverticulosis, neuropathy syndrome (disorder) |
| 705 | Peripheral neuropathy due to hypervitaminosis B6 (disorder) |
| 706 | Length-dependent peripheral neuropathy (disorder) |
| 707 | Autosomal dominant optic atrophy and peripheral neuropathy syndrome (disorder) |
| 708 | Peripheral neuropathy due to metabolic disorder (disorder) |
| 709 | Small fiber neuropathy (disorder) |
| 710 | Peripheral neuropathy due to inflammation (disorder) |
| 711 | Peripheral neuropathy caused by toxin (disorder) |
| 712 | Neuropathy of lower limb (disorder) |
| 713 | Neuropathy of upper limb (disorder) |
| 714 | Ependymal cyst of spinal nerve (disorder) |
| 715 | Peripheral nerve disorder associated with repair of hernia (disorder) |
| 716 | Facial nerve disorder (disorder) |
| 717 | Abducens nerve disorder (disorder) |
| 718 | Pudendal nerve neuropathy (disorder) |
| 719 | Neuromyotonia (disorder) |
| 720 | Thoracoabdominal neuropathy (disorder) |
| 721 | Long thoracic nerve lesion (disorder) |
| 722 | Disorder of peripheral nerve graft (disorder) |
| 723 | Peripheral nerve decompression injury (disorder) |
| 724 | Intercostal neuropathy (disorder) |
| 725 | Compression neuropathy of trunk (disorder) |
| 726 | Ischemic neuropathy (disorder) |
| 727 | Leprosy neuropathy (disorder) |
| 728 | Peripheral axonal neuropathy (disorder) |
| 729 | Phrenic nerve disorder (disorder) |
| 730 | Peripheral neuritis (disorder) |
| 731 | Mononeuropathy (disorder) |
| 732 | Neoplasm of peripheral nerve (disorder) |
| 733 | Celiac plexus syndrome (disorder) |
| 734 | Perineurial cyst (disorder) |
| 735 | Disorder of glossopharyngeal nerve (disorder) |
| 736 | Disorder of acoustic nerve (disorder) |
| 737 | Brachial plexus neuralgia (disorder) |
| 738 | Disorder of vagus nerve (disorder) |
| 739 | Peripheral nerve injury (disorder) |
| 740 | Nerve root disorder (disorder) |
| 741 | Trigeminal nerve disorder (disorder) |
| 742 | Third cranial nerve disease (disorder) |
| 743 | Polyneuropathy (disorder) |
| 744 | Disorder of hypoglossal nerve (disorder) |
| 745 | Congenital anomaly of peripheral nerve (disorder) |
| 746 | Peripheral demyelinating neuropathy (disorder) |
| 747 | Familial visceral neuropathy (disorder) |
| 748 | Fourth nerve palsy (disorder) |
| 749 | Cerebrovascular accident (disorder) |
| 750 | Cerebellar stroke (disorder) |
| 751 | Cerebrovascular accident due to stenosis of left carotid artery (disorder) |
| 752 | Cerebrovascular accident due to stenosis of right carotid artery (disorder) |
| 753 | Cerebrovascular accident due to occlusion of right cerebellar artery (disorder) |
| 754 | Cerebrovascular accident due to occlusion of left cerebellar artery (disorder) |
| 755 | Cerebrovascular accident due to occlusion of left carotid artery (disorder) |
| 756 | Cerebrovascular accident due to occlusion of right pontine artery (disorder) |
| 757 | Cerebrovascular accident due to occlusion of left pontine artery (disorder) |
| 758 | Cerebrovascular accident due to occlusion of right carotid artery (disorder) |
| 759 | Cerebrovascular accident due to occlusion of left vertebral artery (disorder) |
| 760 | Cerebrovascular accident due to occlusion of right vertebral artery (disorder) |
| 761 | Cerebrovascular accident due to stenosis of left vertebral artery (disorder) |
| 762 | Cerebrovascular accident due to stenosis of right vertebral artery (disorder) |
| 763 | Occlusion of cerebral artery with stroke (disorder) |
| 764 | Stroke co-occurrent with migraine (disorder) |
| 765 | Silent cerebral infarct (disorder) |
| 766 | Cerebrovascular accident during surgery (disorder) |
| 767 | Ischemic stroke (disorder) |
| 768 | Infarction of basal ganglia (disorder) |
| 769 | Neonatal stroke (disorder) |
| 770 | Embolic stroke (disorder) |
| 771 | Thrombotic stroke (disorder) |
| 772 | Extension of cerebrovascular accident (disorder) |
| 773 | Stroke in the puerperium (disorder) |
| 774 | Ruptured cerebral aneurysm (disorder) |
| 775 | Stroke of uncertain pathology (disorder) |
| 776 | Cerebrovascular accident due to occlusion of cerebral artery (disorder) |
| 777 | Right sided cerebral hemisphere cerebrovascular accident (disorder) |
| 778 | Left sided cerebral hemisphere cerebrovascular accident (disorder) |
| 779 | Brainstem stroke syndrome (disorder) |
| 780 | Paralytic stroke (disorder) |
| 781 | Nonparalytic stroke (disorder) |
| 782 | Intracranial sinus thrombosis, embolism AND/OR inflammation (disorder) |
| 783 | Progressing stroke (disorder) |
| 784 | Juvenile myopathy, encephalopathy, lactic acidosis AND stroke (disorder) |
| 785 | Completed stroke (disorder) |
| 786 | Anterior choroidal artery syndrome (disorder) |
| 787 | Basilar artery syndrome (disorder) |
| 788 | Peripheral neuropathy co-occurrent and due to diabetes mellitus (disorder) |
| 789 | Peripheral neuropathy co-occurrent and due to type 1 diabetes mellitus (disorder) |
| 790 | Peripheral neuropathy co-occurrent and due to type 2 diabetes mellitus (disorder) |
| 791 | Ophthalmoplegia co-occurrent and due to diabetes mellitus (disorder) |
| 792 | Mononeuropathy co-occurrent and due to diabetes mellitus (disorder) |
| 793 | Asymmetric proximal motor neuropathy co-occurrent and due to diabetes mellitus (disorder) |
| 794 | Polyneuropathy co-occurrent and due to diabetes mellitus (disorder) |
| 795 | Radiculoplexus neuropathy co-occurrent and due to diabetes mellitus (disorder) |
| 796 | Symmetric proximal motor neuropathy co-occurrent and due to diabetes mellitus (disorder) |
| 797 | Pseudotabes co-occurrent and due to diabetes mellitus (disorder) |
| 798 | Cobalamin deficiency (disorder) |
| 799 | Fetal or neonatal vitamin B12 deficiency due to maternal vitamin B12 deficiency (disorder) |
| 800 | Vitamin B12 deficiency (non anemic) (disorder) |
| 801 | Acute mastoiditis with labyrinthitis (disorder) |
| 802 | Benign paroxysmal positional vertigo (disorder) |
| 803 | Benign paroxysmal positional vertigo or nystagmus (disorder) |
| 804 | Benign paroxysmal vertigo of childhood (disorder) |
| 805 | Hearing loss (disorder) |
| 806 | Mild to moderate hearing loss (disorder) |
| 807 | Severe hearing loss (disorder) |
| 808 | Aphonia, deafness, retinal dystrophy, bifid halluces, intellectual disability syndrome (disorder) |
| 809 | Acquired hearing loss (disorder) |

TABLE 11-continued

| Number | Data Element |
|---|---|
| 810 | Oro-facial digital syndrome type 11 (disorder) |
| 811 | Deafness craniofacial syndrome (disorder) |
| 812 | Microcephaly with deafness and intellectual disability syndrome (disorder) |
| 813 | Hearing loss of left ear (disorder) |
| 814 | Hearing loss of right ear (disorder) |
| 815 | Combined visual and hearing impairment (disorder) |
| 816 | Asymmetrical hearing loss (disorder) |
| 817 | Partial deafness (disorder) |
| 818 | On examination - deaf (disorder) |
| 819 | Deafness symptom (disorder) |
| 820 | Chronic deafness (disorder) |
| 821 | On examination - significantly deaf (disorder) |
| 822 | Bilateral deafness (disorder) |
| 823 | Birth trauma deafness (disorder) |
| 824 | Congenital anomaly of ear with impairment of hearing (disorder) |
| 825 | Neonatal hearing loss (disorder) |
| 826 | Bilateral hearing loss (disorder) |
| 827 | Traumatic deafness (disorder) |
| 828 | Sudden hearing loss (disorder) |
| 829 | Noise-induced hearing loss (disorder) |
| 830 | Deaf mutism (disorder) |
| 831 | Sensorineural hearing loss (disorder) |
| 832 | Tone deafness (disorder) |
| 833 | Upper frequency deafness (disorder) |
| 834 | Conductive hearing loss (disorder) |
| 835 | Paradoxic hearing loss (disorder) |
| 836 | Toxic deafness (disorder) |
| 837 | Psychogenic deafness (disorder) |
| 838 | Robinson nail dystrophy-deafness syndrome (disorder) |
| 839 | Complete deafness (disorder) |
| 840 | Ménière's disease (disorder) |
| 841 | Meniere's disease of right inner ear (disorder) |
| 842 | Meniere's disease of left inner ear (disorder) |
| 843 | Familial Ménière disease (disorder) |
| 844 | Vestibular Ménière syndrome (disorder) |
| 845 | Cochlear Ménière syndrome (disorder) |
| 846 | Inactive Ménière's disease (disorder) |
| 847 | Active Ménière's disease (disorder) |
| 848 | Cataract (disorder) |
| 849 | Infantile and/or juvenile cataract (disorder) |
| 850 | Microcornea, rod-cone dystrophy, cataract, posterior staphyloma syndrome (disorder) |
| 851 | Cataract due to pseudohypoparathyroidism (disorder) |
| 852 | Cataract due to idiopathic hypoparathyroidism (disorder) |
| 853 | Cochleosaccular degeneration and cataract syndrome (disorder) |
| 854 | Hyperferritinemia cataract syndrome (disorder) |
| 855 | Immature cataract (disorder) |
| 856 | Presenile cataract (disorder) |
| 857 | Nonsenile cataract (disorder) |
| 858 | Suture tip cataract (disorder) |
| 859 | Mixed type cataract (disorder) |
| 860 | Hypermature cataract (disorder) |
| 861 | Rubella cataract (disorder) |
| 862 | Cataract in systemic disorders (disorder) |
| 863 | Capsular cataract (disorder) |
| 864 | Drug-induced cataract (disorder) |
| 865 | Lamellar zonular cataract (disorder) |
| 866 | Cortical cataract (disorder) |
| 867 | Infantile, juvenile and presenile cataracts (disorder) |
| 868 | On examination - lens - early opacity (disorder) |
| 869 | Partial cataract (disorder) |
| 870 | Adherent cataract (disorder) |
| 871 | Stationary cataract (disorder) |
| 872 | Axial cataract (disorder) |
| 873 | Subcapsular cataract (disorder) |
| 874 | Bilateral cataracts (disorder) |
| 875 | Congenital cataract (disorder) |
| 876 | Cataract with neovascularization (disorder) |
| 877 | Cataract associated with radiation (disorder) |
| 878 | Postoperative cataract syndrome (disorder) |
| 879 | Nuclear cataract (disorder) |
| 880 | Incipient cataract (disorder) |
| 881 | Localized traumatic opacity (disorder) |
| 882 | Punctate cataract (disorder) |
| 883 | Age-related cataract (disorder) |
| 884 | Toxic cataract (disorder) |
| 885 | Traumatic cataract (disorder) |
| 886 | Cataract in inflammatory disorder (disorder) |
| 887 | Coronary cataract (disorder) |
| 888 | Calcified cataract (disorder) |
| 889 | Atopic cataract (disorder) |
| 890 | Mature cataract (disorder) |
| 891 | Glaucoma (disorder) |
| 892 | Glaucoma and sleep apnea syndrome (disorder) |
| 893 | Angle-closure glaucoma (disorder) |
| 894 | Acute-on-chronic glaucoma (disorder) |
| 895 | Glaucoma with intraocular hemorrhage (disorder) |
| 896 | Iatrogenic glaucoma (disorder) |
| 897 | Congenital glaucoma (disorder) |
| 898 | Borderline glaucoma (disorder) |
| 899 | Secondary glaucoma (disorder) |
| 900 | Glaucoma due to combination of mechanisms (disorder) |
| 901 | Open-angle glaucoma (disorder) |
| 902 | Glaucoma of childhood (disorder) |
| 903 | Glaucoma associated with ocular disorder (disorder) |
| 904 | Glaucoma associated with systemic syndromes (disorder) |
| 905 | Low tension glaucoma (disorder) |
| 906 | Anatomical narrow angle glaucoma (disorder) |
| 907 | Hypersecretion glaucoma (disorder) |
| 908 | Glaucoma associated with tumors AND/OR cysts (disorder) |
| 909 | Absolute glaucoma (disorder) |
| 910 | Aphakic glaucoma (disorder) |
| 911 | Glaucomatous atrophy of optic disc (disorder) |
| 912 | Age-related macular degeneration (disorder) |
| 913 | Nonexudative age-related macular degeneration (disorder) |
| 914 | Exudative age-related macular degeneration (disorder) |
| 915 | Drusen plus pigment change stage macular degeneration (disorder) |
| 916 | Fibrovascular macular scar (disorder) |
| 917 | Drusen stage macular degeneration (disorder) |
| 918 | Muscle weakness (finding) |
| 919 | Muscle weakness of limb (finding) |
| 920 | Spastic paresis (finding) |
| 921 | Hand muscle weakness (finding) |
| 922 | Pyramidal type muscle weakness (finding) |
| 923 | Distal muscle weakness (finding) |
| 924 | Proximal muscle weakness (finding) |
| 925 | Truncal muscle weakness (finding) |
| 926 | Weakness of sternomastoid (finding) |
| 927 | Weakness of jaw muscles (finding) |
| 928 | On examination - muscle power reduced (finding) |
| 929 | On examination - paresis (weakness) (finding) |
| 930 | Weakness present (finding) |
| 931 | Pseudoparalysis (finding) |
| 932 | Palatal paresis (finding) |
| 933 | Laryngeal paresis (finding) |
| 934 | Pharyngeal paresis (finding) |
| 935 | Bilateral paresis (finding) |
| 936 | Subjective muscle weakness (finding) |
| 937 | Paresis of lower extremity (finding) |
| 938 | Weakness of face muscles (finding) |
| 939 | Diaphragmatic paresis (finding) |
| 940 | Neurological muscle weakness (finding) |
| 941 | Spinal paraparesis (finding) |
| 942 | Spinal hemiparesis (finding) |
| 943 | Inherited spastic paresis (disorder) |
| 944 | Abnormal gait due to impairment of balance (finding) |
| 945 | Impairment of balance (finding) |
| 946 | Difficulty balancing (finding) |
| 947 | Does not balance (finding) |
| 948 | Unable to balance (finding) |
| 949 | General unsteadiness (finding) |
| 950 | Equilibration disorder, vestibular nerve (disorder) |
| 951 | Unsteady when turning (finding) |
| 952 | Unsteady when standing (finding) |
| 953 | Poor balance (finding) |
| 954 | Keeps losing balance (finding) |
| 955 | Feels as though will fall (finding) |
| 956 | Romberg test positive and direction of fall affected by head turn (finding) |
| 957 | Romberg test evokes stiff fall backward (finding) |
| 958 | Loss of equilibrium (finding) |
| 959 | Visual impairment (disorder) |

TABLE 11-continued

| Number | Data Element |
|---|---|
| 960 | Bilateral visual impairment (disorder) |
| 961 | Visual impairment co-occurrent with human immunodeficiency virus infection (disorder) |
| 962 | Drug related visual impairment (disorder) |
| 963 | Combined visual and hearing impairment (disorder) |
| 964 | Multiple disability visual impairment (disorder) |
| 965 | Mild visual impairment (disorder) |
| 966 | Moderate visual impairment (disorder) |
| 967 | Severe visual impairment (disorder) |
| 968 | Orthostatic hypotension (disorder) |
| 969 | Postural hypotension following exercise (disorder) |
| 970 | Orthostatic hypotension co-occurrent and due to Parkinson's disease (disorder) |
| 971 | Postural orthostatic tachycardia syndrome (disorder) |
| 972 | Sympathotonic orthostatic hypotension (disorder) |
| 973 | Chronic orthostatic hypotension (disorder) |
| 974 | Hypoadrenergic postural hypotension (disorder) |
| 975 | Hyperadrenergic postural hypotension (disorder) |
| 976 | Arthritis (disorder) |
| 977 | Arthritis of right sternoclavicular joint (disorder) |
| 978 | Arthritis of left sternoclavicular joint (disorder) |
| 979 | Primary chronic gout without tophus of shoulder (disorder) |
| 980 | Gout of shoulder caused by drug (disorder) |
| 981 | Transient arthritis (disorder) |
| 982 | Arthritis of wrist (disorder) |
| 983 | Interstitial granulomatous dermatitis with arthritis (disorder) |
| 984 | Immune dysregulation, inflammatory bowel disease, arthritis, recurrent infection syndrome (disorder) |
| 985 | Monoarthritis (disorder) |
| 986 | Inflammation of joint of hand (disorder) |
| 987 | Inflammation of joint of shoulder region (disorder) |
| 988 | Arthritis of elbow (disorder) |
| 989 | Arthritis of acromioclavicular joint (disorder) |
| 990 | Inflammatory polyarthropathy (disorder) |
| 991 | Undifferentiated inflammatory arthritis (disorder) |
| 992 | Synovitis (disorder) |
| 993 | Seronegative arthritis (disorder) |
| 994 | Infective arthritis (disorder) |
| 995 | Suppurative arthritis (disorder) |
| 996 | Arthritis of spine (disorder) |
| 997 | Cricoarytenoid joint arthritis (disorder) |
| 998 | Lower limb joint arthritis (disorder) |
| 999 | Small and large joint arthritis (disorder) |
| 1000 | Large joint arthritis (disorder) |
| 1001 | Small joint arthritis (disorder) |
| 1002 | Asymmetrical arthritis (disorder) |
| 1003 | Symmetrical arthritis (disorder) |
| 1004 | Cholesterol-related arthritis and periarthritis (disorder) |
| 1005 | Oxalate-related arthritis and periarthritis (disorder) |
| 1006 | Idiopathic pyrophosphate arthritis (disorder) |
| 1007 | Chronic infantile neurological, cutaneous and articular syndrome (disorder) |
| 1008 | Arthritis following intestinal bypass (disorder) |
| 1009 | Post-immunization arthritis (disorder) |
| 1010 | Palindromic rheumatism of the pelvic region and thigh (disorder) |
| 1011 | Palindromic rheumatism of the shoulder region (disorder) |
| 1012 | Generalized arthritis (disorder) |
| 1013 | Erosive osteoarthrosis (disorder) |
| 1014 | Arthropathy in Crohn's disease (disorder) |
| 1015 | Systemic lupus erythematosus arthritis (disorder) |
| 1016 | Arthritis of temporomandibular joint (disorder) |
| 1017 | Climacteric arthritis (disorder) |
| 1018 | Osteochondritis (disorder) |
| 1019 | Rheumatoid arthritis (disorder) |
| 1020 | Subacute arthritis (disorder) |
| 1021 | Chronic arthritis (disorder) |
| 1022 | Acute arthritis (disorder) |
| 1023 | Arthritis associated with another disorder (disorder) |
| 1024 | Cerebrovascular accident (disorder) |
| 1025 | Cerebellar stroke (disorder) |
| 1026 | Cerebrovascular accident due to stenosis of left carotid artery (disorder) |
| 1027 | Cerebrovascular accident due to stenosis of right carotid artery (disorder) |
| 1028 | Cerebrovascular accident due to occlusion of right cerebellar artery (disorder) |
| 1029 | Cerebrovascular accident due to occlusion of left cerebellar artery (disorder) |
| 1030 | Cerebrovascular accident due to occlusion of left carotid artery (disorder) |
| 1031 | Cerebrovascular accident due to occlusion of right pontine artery (disorder) |
| 1032 | Cerebrovascular accident due to occlusion of left pontine artery (disorder) |
| 1033 | Cerebrovascular accident due to occlusion of right carotid artery (disorder) |
| 1034 | Cerebrovascular accident due to occlusion of left vertebral artery (disorder) |
| 1035 | Cerebrovascular accident due to occlusion of right vertebral artery (disorder) |
| 1036 | Cerebrovascular accident due to stenosis of left vertebral artery (disorder) |
| 1037 | Cerebrovascular accident due to stenosis of right vertebral artery (disorder) |
| 1038 | Occlusion of cerebral artery with stroke (disorder) |
| 1039 | Stroke co-occurrent with migraine (disorder) |
| 1040 | Silent cerebral infarct (disorder) |
| 1041 | Cerebrovascular accident during surgery (disorder) |
| 1042 | Ischemic stroke (disorder) |
| 1043 | Infarction of basal ganglia (disorder) |
| 1044 | Neonatal stroke (disorder) |
| 1045 | Embolic stroke (disorder) |
| 1046 | Thrombotic stroke (disorder) |
| 1047 | Extension of cerebrovascular accident (disorder) |
| 1048 | Stroke in the puerperium (disorder) |
| 1049 | Ruptured cerebral aneurysm (disorder) |
| 1050 | Stroke of uncertain pathology (disorder) |
| 1051 | Cerebrovascular accident due to occlusion of cerebral artery (disorder) |
| 1052 | Right sided cerebral hemisphere cerebrovascular accident (disorder) |
| 1053 | Left sided cerebral hemisphere cerebrovascular accident (disorder) |
| 1054 | Brainstem stroke syndrome (disorder) |
| 1055 | Paralytic stroke (disorder) |
| 1056 | Nonparalytic stroke (disorder) |
| 1057 | Intracranial sinus thrombosis, embolism AND/OR inflammation (disorder) |
| 1058 | Progressing stroke (disorder) |
| 1059 | Juvenile myopathy, encephalopathy, lactic acidosis AND stroke (disorder) |
| 1060 | Completed stroke (disorder) |
| 1061 | Anterior choroidal artery syndrome (disorder) |
| 1062 | Urinary incontinence (finding) |
| 1063 | Urinary incontinence due to benign prostatic hypertrophy (finding) |
| 1064 | Urinary incontinence co-occurrent and due to prolapse of female genital organ (finding) |
| 1065 | Intermittent urinary incontinence (finding) |
| 1066 | Urinary incontinence due to urethral sphincter incompetence (finding) |
| 1067 | Total urinary incontinence (finding) |
| 1068 | Double incontinence (finding) |
| 1069 | Urinary incontinence of non-organic origin (finding) |
| 1070 | Parkinson's disease (disorder) |
| 1071 | Sporadic Parkinson disease (disorder) |
| 1072 | Orthostatic hypotension co-occurrent and due to Parkinson's disease (disorder) |
| 1073 | Autosomal dominant late onset Parkinson disease (disorder) |
| 1074 | Young onset Parkinson disease (disorder) |
| 1075 | Juvenile Parkinson's disease (disorder) |
| 1076 | Dementia (disorder) |
| 1077 | Primary degenerative dementia (disorder) |
| 1078 | Dementia with behavioral disturbance (disorder) |
| 1079 | Protein kinase cAMP-dependent type I regulatory subunit beta-related neurodegenerative dementia with intermediate filaments (disorder) |
| 1080 | Subcortical dementia (disorder) |
| 1081 | Dementia following injury caused by exposure to ionizing radiation (disorder) |
| 1082 | Dementia caused by heavy metal exposure (disorder) |
| 1083 | Delirium co-occurrent with dementia (disorder) |
| 1084 | Rapidly progressive dementia (disorder) |
| 1085 | Dementia caused by toxin (disorder) |

TABLE 11-continued

| Number | Data Element |
|---|---|
| 1086 | Parkinsonism co-occurrent with dementia of Guadeloupe (disorder) |
| 1087 | Dementia co-occurrent with human immunodeficiency virus infection (disorder) |
| 1088 | Dementia in remission (disorder) |
| 1089 | Dementia of frontal lobe type (disorder) |
| 1090 | Senile and presenile organic psychotic conditions (disorder) |
| 1091 | Patchy dementia (disorder) |
| 1092 | Semantic dementia (disorder) |
| 1093 | Dementia associated with another disease (disorder) |
| 1094 | Drug-induced dementia (disorder) |
| 1095 | Parkinson-dementia complex of Guam (disorder) |
| 1096 | General paresis - neurosyphilis (disorder) |
| 1097 | Alzheimer's disease (disorder) |
| 1098 | Senile dementia (disorder) |
| 1099 | Presenile dementia (disorder) |
| 1100 | Dialysis dementia (disorder) |
| 1101 | Impaired cognition (finding) |
| 1102 | Behavioral disturbance co-occurrent and due to late onset Alzheimer dementia (disorder) |
| 1103 | Cognitive impairment co-occurrent and due to human immunodeficiency virus infection (disorder) |
| 1104 | Cognitive deficit in attention (finding) |
| 1105 | Depressed mood in Alzheimer's disease (disorder) |
| 1106 | Delusions in Alzheimer's disease (disorder) |
| 1107 | Cognitive changes due to organic disorder (finding) |
| 1108 | Early onset Alzheimer's disease with behavioral disturbance (disorder) |
| 1109 | Altered behavior in Alzheimer's disease (disorder) |
| 1110 | Dementia due to multiple sclerosis with altered behavior (disorder) |
| 1111 | Altered behavior in dementia due to Huntington chorea (disorder) |
| 1112 | Hallucinations co-occurrent and due to late onset dementia (disorder) |
| 1113 | Cognitive impairment due to toxicity of substance (disorder) |
| 1114 | Impaired executive functioning (finding) |
| 1115 | Dissociative neurological symptom disorder co-occurrent with cognitive symptoms (disorder) |
| 1116 | Cognitive impairment co-occurrent and due to primary psychotic disorder (disorder) |
| 1117 | Severe cognitive impairment (finding) |
| 1118 | Moderate cognitive impairment (finding) |
| 1119 | Memory impairment (finding) |
| 1120 | Impaired environmental interpretation syndrome (finding) |
| 1121 | Disturbance of cognitive learning (finding) |
| 1122 | Lack of thinking ability (finding) |
| 1123 | Minimal cognitive impairment (finding) |
| 1124 | Age-related cognitive decline (finding) |
| 1125 | Diabetes mellitus (disorder) |
| 1126 | Atypical diabetes mellitus (disorder) |
| 1127 | Diabetes mellitus due to pancreatic injury (disorder) |
| 1128 | Erectile dysfunction co-occurrent and due to diabetes mellitus (disorder) |
| 1129 | Acute complication co-occurrent and due to diabetes mellitus (disorder) |
| 1130 | Metabolic acidosis co-occurrent and due to diabetes mellitus (disorder) |
| 1131 | Lactic acidosis co-occurrent and due to diabetes mellitus (disorder) |
| 1132 | Alaninuria, microcephaly, dwarfism, enamel hypoplasia, diabetes mellitus syndrome (disorder) |
| 1133 | Diabetic mastopathy (disorder) |
| 1134 | Pancreatic hypoplasia, diabetes mellitus, congenital heart disease syndrome (disorder) |
| 1135 | Gingival disease co-occurrent with diabetes mellitus (disorder) |
| 1136 | Diabetes mellitus in remission (disorder) |
| 1137 | Diabetes mellitus due to genetic defect in insulin action (disorder) |
| 1138 | Diabetes mellitus due to genetic defect in beta cell function (disorder) |
| 1139 | Disorder of nervous system co-occurrent and due to diabetes mellitus (disorder) |
| 1140 | Peripheral vascular disorder co-occurrent and due to diabetes mellitus (disorder) |
| 1141 | Disorder of soft tissue co-occurrent and due to diabetes mellitus (disorder) |
| 1142 | Diabetes mellitus during pregnancy, childbirth and the puerperium (disorder) |
| 1143 | Disorder of kidney co-occurrent and due to diabetes mellitus (disorder) |
| 1144 | Houssay's syndrome (disorder) |
| 1145 | Diabetes mellitus without complication (disorder) |
| 1146 | Diabetes mellitus type 1 (disorder) |
| 1147 | Diabetes mellitus type 2 (disorder) |
| 1148 | Disorder of eye co-occurrent and due to diabetes mellitus (disorder) |
| 1149 | Secondary diabetes mellitus (disorder) |
| 1150 | Diabetes insipidus (disorder) |
| 1151 | Partial diabetes insipidus (disorder) |
| 1152 | Hypohidrosis-diabetes insipidus syndrome (disorder) |
| 1153 | Nephrogenic diabetes insipidus (disorder) |
| 1154 | Dipsogenic diabetes insipidus (disorder) |
| 1155 | Idiopathic diabetes insipidus (disorder) |
| 1156 | Diabetes mellitus AND insipidus with optic atrophy AND deafness (disorder) |
| 1157 | Neurohypophyseal diabetes insipidus (disorder) |
| 1158 | Familial diabetes insipidus (disorder) |
| 1159 | Polypharmacy (finding) |
| 1160 | Nutraceutical polypharmacy (finding) |
| 1161 | On four or more medications (finding) |
| 1162 | Patient on numerous drugs (finding) |
| 1163 | Loop diuretic overdose (disorder) |
| 1164 | Aminoglycoside (substance) |
| 1165 | Analgesic (substance) |
| 1166 | Medicinal product acting as analgesic agent (product) |
| 1167 | Substance with opioid receptor agonist mechanism of action (substance) |
| 1168 | Antiarrhythmic agent (substance) |
| 1169 | Medicinal product acting as antiarrhythmic agent (product) |
| 1170 | Quaternary ammonium compound with anticholinergic mechanism of action (substance) |
| 1171 | Vasodilator (substance) |
| 1172 | Hypotensive agent (substance) |
| 1173 | Hypotensive agent (product) |
| 1174 | Anti-psychotic agent (substance) |
| 1175 | Medicinal product acting as antipsychotic agent (product) |
| 1176 | Diuretic (substance) |
| 1177 | Medicinal product acting as diuretic (product) |
| 1178 | Loop diuretic (substance) |
| 1179 | Psychoactive substance (substance) |
| 1180 | Antidepressant (substance) |
| 1181 | Medicinal product acting as antidepressant agent (product) |
| 1182 | Anti-psychotic agent (substance) |
| 1183 | Medicinal product acting as antipsychotic agent (product) |
| 1184 | Benzodiazepine (substance) |
| 1185 | History of Falling |
| 1186 | Fall (event) |
| 1187 | Fall into water (event) |
| 1188 | Fall on soft surface (event) |
| 1189 | Fall on hard surface (event) |
| 1190 | Jump from burning structure (event) |
| 1191 | Accidental fall (event) |
| 1192 | Fall in, on, or from train (event) |
| 1193 | Engaged in falling (event) |
| 1194 | Fall on snow (event) |
| 1195 | Falls (finding) |
| 1196 | Falls caused by medication (finding) |
| 1197 | Elderly fall (finding) |
| 1198 | At risk for falls (finding) |
| 1199 | At high risk for fall (finding) |
| 1200 | At moderate risk for fall (finding) |
| 1201 | At low risk for fall (finding) |
| 1202 | Secondary Diagnosis |
| 1203 | Diagnosis (observable entity) |
| 1204 | Fetal diagnosis (observable entity) |
| 1205 | New diagnosis (observable entity) |
| 1206 | Ambulatory aid |
| 1207 | Ability to walk (observable entity) |
| 1208 | Ability to walk on uneven surface (observable entity) |
| 1209 | Ability to walk backward pulling large toy (observable entity) |
| 1210 | Ability to walk carrying large toy (observable entity) |
| 1211 | Ability to walk heel to toe (observable entity) |

TABLE 11-continued

| Number | Data Element |
|---|---|
| 1212 | Ability to walk on a narrow line (observable entity) |
| 1213 | Ability to start and stop walking spontaneously (observable entity) |
| 1214 | Ability to stop walking (observable entity) |
| 1215 | Ability to initiate walking (observable entity) |
| 1216 | Ability to walk down hill (observable entity) |
| 1217 | Ability to walk up hill (observable entity) |
| 1218 | Ability to walk down a slope (observable entity) |
| 1219 | Ability to walk up a slope (observable entity) |
| 1220 | Ability to walk on the flat (observable entity) |
| 1221 | Finding of walking aid use (finding) |
| 1222 | Uses two walking sticks (finding) |
| 1223 | Uses two crutches for walking (finding) |
| 1224 | Uses single crutch for walking (finding) |
| 1225 | Uses single walking stick (finding) |
| 1226 | Uses zimmer frame (finding) |
| 1227 | Tripod/quadrupod: walking (finding) |
| 1228 | Stick only for walking (finding) |
| 1229 | No aid for walking (finding) |
| 1230 | Dependence on walking stick (finding) |
| 1231 | Cane, device (physical object) |
| 1232 | Long cane (physical object) |
| 1233 | Wheelchair crutch/walking stick holder (physical object) |
| 1234 | Gait |
| 1235 | Gait normal (finding) |
| 1236 | On examination - gait normal (finding) |
| 1237 | Mental Status |
| 1238 | Orientated (finding) |
| 1239 | Oriented to person (finding) |
| 1240 | Oriented to place (finding) |
| 1241 | Oriented to time (finding) |
| 1242 | Oriented to person, time and place (finding) |
| 1243 | Disorientated (finding) |
| 1244 | On examination - disorientated (finding) |
| 1245 | Impaired environmental interpretation syndrome (finding) |
| 1246 | Spatial disorientation (finding) |
| 1247 | Disorientated in place (finding) |
| 1248 | Disorientation as to self (finding) |
| 1249 | Disorientation for person (finding) |
| 1250 | Disorientation as to people, time and place (finding) |
| 1251 | Disorientated in time (finding) |
| 1252 | Right-left disorientation (finding) |
| 1253 | Impaired cognition (finding) |
| 1254 | Behavioral disturbance co-occurrent and due to late onset Alzheimer dementia (disorder) |
| 1255 | Cognitive impairment co-occurrent and due to human immunodeficiency virus infection (disorder) |
| 1256 | Cognitive deficit in attention (finding) |
| 1257 | Depressed mood in Alzheimer's disease (disorder) |
| 1258 | Delusions in Alzheimer's disease (disorder) |
| 1259 | Cognitive changes due to organic disorder (finding) |
| 1260 | Early onset Alzheimer's disease with behavioral disturbance (disorder) |
| 1261 | Altered behavior in Alzheimer's disease (disorder) |
| 1262 | Dementia due to multiple sclerosis with altered behavior (disorder) |
| 1263 | Altered behavior in dementia due to Huntington chorea (disorder) |
| 1264 | Hallucinations co-occurrent and due to late onset dementia (disorder) |
| 1265 | Cognitive impairment due to toxicity of substance (disorder) |
| 1266 | Impaired executive functioning (finding) |
| 1267 | Dissociative neurological symptom disorder co-occurrent with cognitive symptoms (disorder) |
| 1268 | Cognitive impairment co-occurrent and due to primary psychotic disorder (disorder) |
| 1269 | Severe cognitive impairment (finding) |
| 1270 | Moderate cognitive impairment (finding) |
| 1271 | Memory impairment (finding) |
| 1272 | Impaired environmental interpretation syndrome (finding) |
| 1273 | Disturbance of cognitive learning (finding) |
| 1274 | Lack of thinking ability (finding) |
| 1275 | Minimal cognitive impairment (finding) |
| 1276 | Age-related cognitive decline (finding) |
| 1277 | At risk for cognitive impairment (finding) |
| 1278 | At risk of confusion (finding) |
| 1279 | At risk for delirium (finding) |
| 1280 | Wheelchair bound (finding) |
| 1281 | Dependent on helper pushing wheelchair (finding) |
| 1282 | Minimal help in wheelchair (finding) |
| 1283 | Independent in wheelchair (finding) |
| 1284 | Elimination, Bowel and Urine |
| 1285 | Incontinence (finding) |
| 1286 | Incontinence without sensory awareness (finding) |
| 1287 | Incontinence due to detrusor instability (finding) |
| 1288 | Neurogenic incontinence (finding) |
| 1289 | Urinary incontinence (finding) |
| 1290 | Incontinence of feces (finding) |
| 1291 | Micturition finding (finding) |
| 1292 | Abnormal urination (finding) |
| 1293 | Vesicovaginal fistula with involvement of urinary continence mechanism following termination of pregnancy procedure (disorder) |
| 1294 | Vesicovaginal fistula with involvement of urinary continence mechanism following obstetric delivery procedure (disorder) |
| 1295 | Vesicovaginal fistula with involvement of urinary continence mechanism due to and following obstructed labor (disorder) |
| 1296 | Vesicovaginal fistula with involvement of urinary continence mechanism following normal delivery (disorder) |
| 1297 | Finding of bladder control (finding) |
| 1298 | Finding of flow of urine (finding) |
| 1299 | Finding related to ability to pass urine (finding) |
| 1300 | Lower urinary tract symptoms (finding) |
| 1301 | Finding of measures of urination (finding) |
| 1302 | Finding of desire for urination (finding) |
| 1303 | Finding of pattern of urination (finding) |
| 1304 | Dysfunctional voiding of urine (finding) |
| 1305 | Incomplete urination (finding) |
| 1306 | On examination - micturition reflex (finding) |
| 1307 | Control of micturition normal (finding) |
| 1308 | Normal micturition (finding) |
| 1309 | Micturition feature (observable entity) |
| 1310 | Urinary elimination status (observable entity) |
| 1311 | Ability to collect and discharge urine (observable entity) |
| 1312 | Ability to maintain urinary continence (observable entity) |
| 1313 | Measure of urination (observable entity) |
| 1314 | Characteristic of desire for urination (observable entity) |
| 1315 | Pattern of urination (observable entity) |
| 1316 | Urinary flow pattern (observable entity) |
| 1317 | Ability to pass urine (observable entity) |
| 1318 | Flow of urine (observable entity) |
| 1319 | Bowel finding (finding) |
| 1320 | Intestinal anastomosis present (finding) |
| 1321 | Bowel problem (finding) |
| 1322 | Aware of passing feces (finding) |
| 1323 | Desire for stool finding (finding) |
| 1324 | Finding of measures of defecation (finding) |
| 1325 | Finding of passage of meconium (finding) |
| 1326 | Finding of quantity of defecation (finding) |
| 1327 | Finding of frequency of defecation (finding) |
| 1328 | Finding of speed of defecation (finding) |
| 1329 | Tympanitic bowel sound (finding) |
| 1330 | Bowel assessment observations (finding) |
| 1331 | Bowel sounds continuous (finding) |
| 1332 | Bowel sounds intermittent (finding) |
| 1333 | Bowel sounds loud (finding) |
| 1334 | Bowel sounds quiet (finding) |
| 1335 | Bowel control - child (finding) |
| 1336 | Bowel sounds tinkling (finding) |
| 1337 | Bowel spasm (finding) |
| 1338 | Unaware of passing feces (finding) |
| 1339 | Constipation alternates with diarrhea (finding) |
| 1340 | Sensation as if diarrhea will start (finding) |
| 1341 | Sensation as if bowel still full (finding) |
| 1342 | Intestinal hurry (finding) |
| 1343 | Finding of large intestine (finding) |
| 1344 | Finding of small intestine (finding) |
| 1345 | Disorder of intestine (disorder) |
| 1346 | Double incontinence (finding) |
| 1347 | Urgent desire for stool (finding) |
| 1348 | Multiple diverticula of intestine (finding) |
| 1349 | Abdominal wind pain (finding) |
| 1350 | Passes stool completely (finding) |
| 1351 | Finding of defecation (finding) |
| 1352 | Defecation reflex finding (finding) |
| 1353 | Finding related to awareness of bowel function (finding) |

TABLE 11-continued

| Number | Data Element |
|---|---|
| 1354 | Finding of bowel action (finding) |
| 1355 | Finding of bowel continence (finding) |
| 1356 | Soiling (finding) |
| 1357 | Defecation observable (observable entity) |
| 1358 | St. Mark's incontinence score (observable entity) |
| 1359 | Time of last bowel movement (observable entity) |
| 1360 | Bowel elimination status (observable entity) |
| 1361 | Awareness of bowel function (observable entity) |
| 1362 | Feces/motions - symptoms (observable entity) |
| 1363 | Bowel action (observable entity) |
| 1364 | Requires supervision to perform wheelchair transfer (finding) |
| 1365 | Unsteady gait (finding) |
| 1366 | Visual impairment (disorder) |
| 1367 | Bilateral visual impairment (disorder) |
| 1368 | Visual impairment co-occurrent with human immunodeficiency virus infection (disorder) |
| 1369 | Drug related visual impairment (disorder) |
| 1370 | Combined visual and hearing impairment (disorder) |
| 1371 | Multiple disability visual impairment (disorder) |
| 1372 | Mild visual impairment (disorder) |
| 1373 | Moderate visual impairment (disorder) |
| 1374 | Severe visual impairment (disorder) |
| 1375 | Disorder of auditory system (disorder) |
| 1376 | Weissenbacher-Zweymuller syndrome (disorder) |
| 1377 | Cogan's syndrome (disorder) |
| 1378 | Auditory system hereditary disorder (disorder) |
| 1379 | Auditory system complication of procedure (disorder) |
| 1380 | Auditory dysfunction (disorder) |
| 1381 | Olivary heterotopia (disorder) |
| 1382 | Olive dysplasia (disorder) |
| 1383 | Hearing disorder (disorder) |
| 1384 | Disorder of ear (disorder) |
| 1385 | Non-awareness of common dangers (finding) |
| 1386 | Not aware of danger from deep water (finding) |
| 1387 | Lack of common sense about danger (finding) |
| 1388 | Not aware of danger from strangers (finding) |
| 1389 | Not aware of danger from traffic (finding) |
| 1390 | Not aware of danger from falling from heights (finding) |
| 1391 | Not aware of danger from sharp objects (finding) |
| 1392 | Not aware of danger from hot objects (finding) |
| 1393 | Lack of self awareness (finding) |
| 1394 | Poor awareness of safety at work (finding) |
| 1395 | Impulsive character (finding) |
| 1396 | Making impulsive remarks (finding) |
| 1397 | On examination - impulsive behavior (finding) |
| 1398 | Explosive personality disorder (disorder) |
| 1399 | Isolated explosive disorder (disorder) |
| 1400 | Cognitive seizure (disorder) |
| 1401 | Cognitive disorder (disorder) |
| 1402 | Neurocognitive disorder (disorder) |
| 1403 | Cognitive disorder in remission (disorder) |
| 1404 | Cognitive developmental delay (disorder) |
| 1405 | Mild cognitive disorder (disorder) |
| 1406 | Language-related cognitive disorder (disorder) |
| 1407 | Age-associated memory impairment (disorder) |
| 1408 | Cognitive dysfunction following surgical procedure (disorder) |
| 1409 | Impaired cognition (finding) |
| 1410 | Behavioral disturbance co-occurrent and due to late onset Alzheimer dementia (disorder) |
| 1411 | Cognitive impairment co-occurrent and due to human immunodeficiency virus infection (disorder) |
| 1412 | Cognitive deficit in attention (finding) |
| 1413 | Depressed mood in Alzheimer's disease (disorder) |
| 1414 | Delusions in Alzheimer's disease (disorder) |
| 1415 | Cognitive changes due to organic disorder (finding) |
| 1416 | Early onset Alzheimer's disease with behavioral disturbance (disorder) |
| 1417 | Altered behavior in Alzheimer's disease (disorder) |
| 1418 | Dementia due to multiple sclerosis with altered behavior (disorder) |
| 1419 | Altered behavior in dementia due to Huntington chorea (disorder) |
| 1420 | Hallucinations co-occurrent and due to late onset dementia (disorder) |
| 1421 | Cognitive impairment due to toxicity of substance (disorder) |
| 1422 | Impaired executive functioning (finding) |
| 1423 | Dissociative neurological symptom disorder co-occurrent with cognitive symptoms (disorder) |
| 1424 | Cognitive impairment co-occurrent and due to primary psychotic disorder (disorder) |
| 1425 | Severe cognitive impairment (finding) |
| 1426 | Moderate cognitive impairment (finding) |
| 1427 | Memory impairment (finding) |
| 1428 | Impaired environmental interpretation syndrome (finding) |
| 1429 | Disturbance of cognitive learning (finding) |
| 1430 | Lack of thinking ability (finding) |
| 1431 | Minimal cognitive impairment (finding) |
| 1432 | Age-related cognitive decline (finding) |
| 1433 | At risk for cognitive impairment (finding) |
| 1434 | At risk of confusion (finding) |
| 1435 | At risk for delirium (finding) |
| 1436 | PROCEDURES/THERAPIES/PHYSICAL OBJECTS |
| 1437 | Analgesic technique (procedure) |
| 1438 | Administration of intravenous antiarrhythmic drug (procedure) |
| 1439 | Diuretic therapy (procedure) |
| 1440 | Antidepressant therapy (procedure) |
| 1441 | Antipsychotic drug therapy (procedure) |
| 1442 | Benzodiazepine therapy (procedure) |
| 1443 | Analgesic technique (procedure) |
| 1444 | Administration of intravenous antiarrhythmic drug (procedure) |
| 1445 | Diuretic therapy (procedure) |
| 1446 | Antidepressant therapy (procedure) |
| 1447 | Antipsychotic drug therapy (procedure) |
| 1448 | Benzodiazepine therapy (procedure) |
| 1449 | Bedrest care (regime/therapy) |
| 1450 | Bedrest (regime/therapy) |
| 1451 | Primary bedrest stabilization of spinal fracture (procedure) |
| 1452 | Primary open reduction spinal fracture and bedrest stabilization (procedure) |
| 1453 | Revision to bedrest stabilization of spinal fracture (procedure) |
| 1454 | Primary closed reduction spinal fracture and bedrest stabilization (procedure) |
| 1455 | Revision to open reduction spinal fracture and bedrest stabilization (procedure) |
| 1456 | Revision to closed reduction spinal fracture and bedrest stabilization (procedure) |
| 1457 | Assistance with mobility (procedure) |
| 1458 | Assistance with mobility in bed (procedure) |
| 1459 | Walking aid (physical object) |
| 1460 | Stick, walking device (physical object) |
| 1461 | Crutches (physical object) |
| 1462 | Walking frame (physical object) |
| 1463 | Tripod (physical object) |
| 1464 | Cane, device (physical object) |
| 1465 | Crutch, device (physical object) |
| 1466 | Cane, device (physical object) |
| 1467 | Long cane (physical object) |
| 1468 | Walking assistive device (physical object) |
| 1469 | Walking stick/Crutches (physical object) |
| 1470 | Walker/Walking frame (physical object) |
| 1471 | Walking aid ice grip (physical object) |
| 1472 | Walking stick holder (physical object) |
| 1473 | Walking aid handgrip (physical object) |
| 1474 | Walking aid tip (physical object) |
| 1475 | Walker (physical object) |
| 1476 | Gait rehabilitation electronic walker (physical object) |
| 1477 | Walking chair, non-foldable (physical object) |
| 1478 | Walking table (physical object) |
| 1479 | Basic walker, non-foldable (physical object) |
| 1480 | Walking chair, foldable (physical object) |
| 1481 | Basic walker, foldable (physical object) |
| 1482 | Bariatric walker, non-foldable (physical object) |
| 1483 | Bariatric walker, foldable (physical object) |
| 1484 | Patient/medical device walker, home-use (physical object) |
| 1485 | Patient/medical device walker (physical object) |
| 1486 | Intravenous therapy/heparin lock |
| 1487 | Heparin lock flush syringe, single-use (physical object) |
| 1488 | Heparin lock flush syringe, reprocessed (physical object) |
| 1489 | Intravenous therapy (regime/therapy) |
| 1490 | Checking intravenous tubing for air bubbles (regime/therapy) |
| 1491 | Changing intravenous infusion line (regime/therapy) |
| 1492 | Administration of sedative (procedure) |

TABLE 11-continued

| Number | Data Element |
|---|---|
| 1493 | Benzodiazepine therapy (procedure) |
| 1494 | Administration of sedative via rectal route (procedure) |
| 1495 | Induction of minimal sedation (procedure) |
| 1496 | Induction of deep sedation (procedure) |
| 1497 | Induction of conscious sedation (procedure) |
| 1498 | Oral sedation (procedure) |
| 1499 | Sedation with analgesic adjunct (procedure) |
| 1500 | Inhalational sedation (procedure) |
| 1501 | Intramuscular sedation (procedure) |
| 1502 | Intravenous sedation (procedure) |
| 1503 | Induction of sedation (procedure) |
| 1504 | Premedication for anesthetic procedure (procedure) |
| 1505 | Intravenous infusion (procedure) |
| 1506 | Intravenous radionuclide therapy (procedure) |
| 1507 | Infusion of drug or medicament via intravenous route (procedure) |
| 1508 | Resuscitation using intravenous fluid (procedure) |
| 1509 | Diabetes mellitus insulin-glucose infusion in acute myocardial infarction (procedure) |
| 1510 | Continuous infusion of dextrose saline (procedure) |
| 1511 | Continuous infusion of normal saline (procedure) |
| 1512 | Intravenous blood transfusion (procedure) |
| 1513 | Intravenous blood transfusion of platelets (procedure) |
| 1514 | Insertion of pleural tube drain (procedure) |
| 1515 | Opening of chest and insertion of pleural tube drain (procedure) |
| 1516 | Insertion of drainage tube into pleural cavity using ultrasound guidance (procedure) |
| 1517 | Insertion of pleural tube using computed tomography guidance (procedure) |
| 1518 | Thoracentesis with insertion of pleural tube (procedure) |
| 1519 | Insertion of underwater seal chest drain (procedure) |
| 1520 | Tube thoracostomy with water seal (procedure) |
| 1521 | Injection of indwelling catheter (procedure) |
| 1522 | Hickman line injection (procedure) |
| 1523 | Portocath injection (procedure) |
| 1524 | Replacement of indwelling catheter of urinary bladder (procedure) |
| 1525 | Deflating indwelling urethral catheter balloon (procedure) |
| 1526 | Catheterization of bladder by indwelling suprapubic catheter (procedure) |
| 1527 | Therapeutic drainage of amniotic fluid by indwelling catheter (procedure) |
| 1528 | Insertion of tunneled indwelling catheter with cuff into pleura (procedure) |
| 1529 | Insertion of indwelling tunneled catheter with cuff by percutaneous approach using radiologic guidance (procedure) |
| 1530 | Insertion of indwelling catheter into urinary bladder (procedure) |
| 1531 | Indwelling catheter removed (situation) |
| 1532 | Indwelling catheter inserted (situation) |
| 1533 | Intermittent pneumatic compression stockings (physical object) |
| 1534 | Assistance with mobility (procedure) |
| 1535 | Assistance with mobility in bed (procedure) |
| 1536 | Self-care assistance: transfer (procedure) |
| 1537 | Able to transfer location with assistance (finding) |
| 1538 | Ambulation training (procedure) |
| 1539 | Gait training procedure (procedure) |
| 1540 | Ambulation therapy (regime/therapy) |
| 1541 | OTHER |
| 1542 | Diagnoses/Comorbidities |
| 1543 | Fluids |
| 1544 | Orders |
| 1545 | Family History |
| 1546 | Prior Bed Exits |
| 1547 | # of Nurse Calls |
| 1548 | Length of Stay |
| 1549 | Rounding Compliance |
| 1550 | Hospital Unit |
| 1551 | RISK INDICATORS |
| 1552 | Falls |
| 1553 | Pulmonary |
| 1554 | Skin |
| 1555 | Mobility Score |
| 1556 | Braden Score |
| 1557 | **RISK SCORES (* = Falls, ** = EWS)** |
| 1558 | Morse* |
| 1559 | Johns Hopkins (JHFRAT)* |
| 1560 | Hendrich* |
| 1561 | Humpty Dumpty* |
| 1562 | STRATIFY* |
| 1563 | MEWS** |
| 1564 | NEWS** |
| 1565 | PEWS** |
| 1566 | MEOWS** |
| 1567 | SIRS** |
| 1568 | SOFA** |
| 1569 | RISK STRATIFICATIONS (High, Medium, Low) |
| 1570 | Missing Risk Score/Risk Stratification Parameters |
| 1571 | RESPONSES (NOTIFICATIONS AND ACTIONS) |
| 1572 | RISK CONTEXT (for Patient Deterioration sub-vectors) |
| 1573 | Respiratory Distress |
| 1574 | age >= 70 |
| 1575 | 60 <= age <= 70 |
| 1576 | prior hospitalization within 90 days |
| 1577 | COPD |
| 1578 | morbid obesity |
| 1579 | weight >= 250 lbs & gender = F |
| 1580 | weight >= 300 lbs & gender = M |
| 1581 | abdominal aortic aneurysm surgery |
| 1582 | pneumonia |
| 1583 | albumin < 40 |
| 1584 | blood urea nitrogen > 40 |
| 1585 | respiratory rate > 30 |
| 1586 | respiratory rate < 10 |
| 1587 | spo2 < 95 |
| 1588 | peripheral edema |
| 1589 | current opioids |
| 1590 | pulmonary consult |
| 1591 | blood transfusion |
| 1592 | decreased loc |
| 1593 | restlessness |
| 1594 | Sepsis |
| 1595 | Acute Kidney Injury |
| 1596 | Hemorrhage |
| 1597 | Congestive Heart Failure |
| 1598 | Respiratory Distress |

In Table 11, the bolded entries in the data elements column are headings or data elements categories and the data elements listed beneath the bolded heading line are the data elements within the bolded category.

According to this disclosure, phrases of the form "at least one of A and B" and "at least one of the following: A and B" and similar such phrases, mean "A, or B, or both A and B." Phrases of the form "at least one of A or B" and "at least one of the following: A or B" and similar such phrases, also mean "A, or B, or both A and B."

Although certain illustrative embodiments have been described in detail above, many embodiments, variations and modifications are possible that are still within the scope and spirit of this disclosure as described herein and as defined in the following claims.

The invention claimed is:

1. A system for use in a healthcare facility, the system comprising
an analytics engine,
a plurality of equipment providing data to the analytics engine, the data pertaining to a patient in the healthcare facility, the plurality of equipment including at least one of the following: a patient support apparatus, a nurse call computer, a physiological monitor, a patient lift, a locating computer of a locating system, or an incontinence detection pad, wherein the analytics engine analyzes the data from the plurality of equipment to determine in substantially real time each of the following: a first score relating to a risk of the patient developing sepsis, a second score relating to a risk of the patient falling, and a third score relating to a risk of the patient developing a pressure injury, a computer coupled to the analytics engine and coordinating a caregiver rounding interval at which at least one caregiver assigned to the patient is required to check in on the patient, wherein when the analytics engine determines the first score, in response to the first score increasing from a first value to a second value, the analytics engine automatically activates an infusion pump for the delivery of IV antibiotics and the computer automatically decreases the caregiver rounding interval;

when the analytics engine determines the second score, in response to the second score increasing from a first value to a second value, the analytics engine automatically activates a bed exit or patient position monitoring system and the computer automatically decreases the caregiver rounding interval; and when the analytics engine determines the third score, in response to the third score increasing from a first value to a second value, the analytics engine automatically activates an alternating pressure function of a mattress and the computer automatically decreases the caregiver rounding interval; and wherein the computer automatically increases the caregiver rounding interval in response to the at least one of the first, second, or third scores decreasing from the second value to the first value, and a mobile device of a caregiver assigned to the patient and configured to receive wireless communications initiated by the analytics engine, the mobile device being configured to generate a screen on a display of the mobile device, the screen including:

a first window having a scoring section that includes a modified early warning score (MEWS) calculated by the analytics engine and one or more vital signs that contribute to the calculation of the MEWS score;

a second window indicating the risk of the patient developing sepsis by displaying the first score calculated by the analytics engine; and a third window indicating the risk of the patient falling by displaying the second score calculated by the analytics engine, wherein the screen further includes respective arrow icons that appear adjacent the MEWS, the first score, and the second score to indicate whether the MEWS, the first score, and the second score, respectively, have increased or decreased from a prior reading.

2. The system of claim 1, further comprising a plurality of additional displays communicatively coupled to the analytics engine and operable to display the first, second, and third scores, the plurality of displays comprising at least two of the following: a status board display located at a master nurse station, an in-room display provided by a room station of a nurse call system, and an electronic medical records (EMR) display of an EMR computer.

3. The system of claim 1, wherein the plurality of equipment includes at least three of the following: the patient support apparatus, the nurse call computer, the physiological monitor, the patient lift, the locating computer, and the incontinence detection pad.

4. The system of claim 1, wherein the plurality of equipment includes at least four of the following: the patient support apparatus, the nurse call computer, the physiological monitor, the patient lift, the locating computer, and the incontinence detection pad.

5. The system of claim 1, wherein the plurality of equipment includes at least five of the following: the patient support apparatus, the nurse call computer, the physiological monitor, the patient lift, the locating computer, and the incontinence detection pad.

6. The system of claim 1, wherein the plurality of equipment includes all six of the following: the patient support apparatus, the nurse call computer, the physiological monitor, the patient lift, the locating computer, and the incontinence detection pad.

7. The system of claim 1, wherein each of the first, second, and third scores is normalized by the analytics engine so as to have a minimum value and a maximum value that is common to each of the other first, second, and third scores.

8. The system of claim 7, wherein the minimum value is 0 for each of the first, second, and third scores.

9. The system of claim 7, wherein the minimum value is 1 for each of the first, second, and third scores.

10. The system of claim 7, wherein the maximum value is 5 for each of the first, second, and third scores.

11. The system of claim 1, wherein the analytics engine also receives additional data from an international pressure ulcer prevalence (IPUP) survey for the patient and analyzes the additional data in connection with determining at least one of the first, second, and third scores.

12. The system of claim 1, wherein the analytics engine communicates at least two of the first, second, and third scores to at least one piece of equipment of the plurality of equipment.

13. The system of claim 1, wherein the at least one piece of equipment of the plurality of equipment includes a device display and wherein steps for lowering at least one of the first, second, and third scores is displayed on the device display.

14. The system of claim 1, wherein the plurality of equipment includes the patient support apparatus and wherein data from the patient support apparatus includes at least one patient vital sign sensed by at least one vital sign sensor integrated into the patient support apparatus.

15. The system of claim 14, wherein the at least one patient vital sign sensed by the at least one vital sign sensor includes heart rate or respiration rate.

16. The system of claim 14, wherein data from the patient support apparatus further includes patient weight.

17. The system of claim 1, wherein the plurality of equipment includes the patient support apparatus and wherein data from the patient support apparatus includes patient weight and a position of the patient on the patient support apparatus.

18. The system of claim 17, wherein data from the patient support apparatus further includes data indicative of an amount of motion by the patient while supported on the patient support apparatus.

19. The system of claim 1, wherein the plurality of equipment includes the physiological monitor and wherein data from the physiological monitor includes one or more of the following: heart rate data, electrocardiograph (EKG) data, respiration rate data, patient temperature data, pulse oximetry data, and blood pressure data.

20. The system of claim 1, wherein the first score is at or near a maximum value if the following criteria exist: i) the patient's temperature is greater than about 38.3° Celsius (C) (about 101° Fahrenheit (F)) or less than about 35.6° C. (about 96° F.), ii) the patient's heart rate is greater than 90 beats per minute; and iii) the patient's respiration rate is greater than 20 respirations per minute.

21. The system of claim 1, wherein the analytics engine initiates a message to the mobile device of the caregiver assigned to the patient if the first, second, or third score increases from a previous value.

22. The system of claim 1, wherein the analytics engine initiates a message to the mobile device of the caregiver assigned to the patient if the first, second, or third score reaches a threshold value.

23. The system of claim 1, wherein the analytics engine also receives additional data relating to at least one wound of the patient and analyzes the additional data in connection with determining at least one of the first, second, and third scores.

24. The system of claim 23, wherein the additional data relating to the at least one wound includes an image of the at least one wound.

25. The system of claim 1, wherein the plurality of equipment includes the patient support apparatus and wherein the patient support apparatus comprises a patient bed or a stretcher.

26. The system of claim 1, wherein the analytics engine also receives additional data relating to at least one of the following: fluid input and output, cardiac output, comorbidities, and bloodwork, and wherein the analytics engine analyzes the additional data in connection with determining at least one of the first, second, and third scores.

27. The system of claim 1, wherein the plurality of equipment includes the physiological monitor and wherein the physiological monitor comprises at least one of the following: a wireless patch sensor attached to the patient, an ambulatory cardiac monitor, an EKG, a respiration rate monitor, a blood pressure monitor, a pulse oximeter, and a thermometer.

28. The system of claim 1, wherein the plurality of equipment further comprises a chair monitor to monitor patient movement while the patient is seated on a chair.

29. The system of claim 1, wherein the plurality of equipment further comprises a toilet monitor to monitor patient movement while the patient is seated on a toilet.

30. The system of claim 1, wherein the analytics engine is configured to receive patient demographics data of the patient including at least one of age, race, and weight;
wherein the analytics engine is configured to receive comorbidity data of the patient including data indicating that the patient has at least one of the following medical conditions: acquired immunodeficiency syndrome (AIDS), anemia, chronic congestive heart failure, asthma, cancer, chronic obstructive pulmonary disease (COPD), coronary artery disease, cystic fibrosis, dementia, emphysema, alcohol or drug abuse, stroke, pulmonary emboli, a history of sepsis, type 1 diabetes, morbid obesity, neuromuscular disease, prior intubation, scoliosis, smoker, delirium, asplenic, bone marrow transplant, cirrhosis, dialysis, diverticulosis, heart valve disorders, inflammatory bowel disease, joint replacement, leukopenia, malignancy, neoplasm, organ transplant, peripheral vascular disease, renal disease, pressure injury, recent abortion, recent childbirth, seizures, sickle cell anemia, or terminal illness;
wherein the plurality of equipment includes the physiological monitor and wherein the analytics engine is configured to receive physiological data measured by the physiological monitor having at least one sensor coupled to, or in communication with, the patient, the physiological data being dynamic and changing over time while the patient is being monitored by the physiological monitor; and
wherein the analytics engine is configured to calculate a risk score of the patient in substantially real time based on the patient demographics data, the comorbidity data, and the physiological data.

31. The system of claim 1, wherein the analytics engine is configured to:
receive dynamic clinical variables and vital signs information of the patient,
use the vital signs information to develop prior vital signs patterns and current vital signs patterns,
compare the prior vital signs patterns with the current vital signs patterns,
receive one or more of the following: static variables of the patient, subjective complaints of the patient, prior healthcare utilization patterns of the patient, or social determinants of health data of the patient, and
use the dynamic clinical variables, the vital signs information, the results of the comparison of the prior vital signs patterns with the current vital signs patterns, and the one or more of the static variables, the subjective complaints, the healthcare utilization patterns, or the social determinants of health data in an algorithm to detect or predict that the patient has sepsis or is likely to develop sepsis.

32. The system of claim 1, wherein a risk determination is made or one or more of the first, second, or third scores is calculated based on one or more of the data elements listed in Table 11.

* * * * *